United States Patent
Wang et al.

(10) Patent No.: US 10,155,722 B2
(45) Date of Patent: Dec. 18, 2018

(54) ANTITUMOR COMPOUND TARGETING IDH2 MUTATION AND METHOD OF USE THEREOF

(71) Applicants: CHIA TAI TIANQING PHARMACEUTICAL GROUP CO., LTD., Lianyungang, Jiangsu Province (CN); LIANYUNGANG RUNZHONG PHARMACEUTICAL CO., LTD., Lianyungang, Jiangsu Province (CN); CENTAURUS BIOPHARMA CO., LTD., Beijing (CN)

(72) Inventors: Shulong Wang, Beijing (CN); Na Zhao, Beijing (CN); Xijie Liu, Beijing (CN); Yuandong Hu, Beijing (CN); Hui Zhang, Beijing (CN); Hong Luo, Beijing (CN); Yong Peng, Beijing (CN); Dengming Xiao, Beijing (CN); Yongxin Han, Beijing (CN); Xiquan Zhang, Lianyungang (CN); Xin Tian, Lianyungang (CN)

(73) Assignees: Chia Tai Tianqing Pharmaceutical Group Co., Ltd., Lianyungang, Jiangsum (CN); Lianyungang Runzhong Pharmaceutical Co., Ltd., Lianyungang, Jiangsu (CN); Centaurus Biopharma Co., Ltd., Beijing (CN)

( * ) Notice: Subject to any disclaimer, the term of this patent is extended or adjusted under 35 U.S.C. 154(b) by 0 days.

(21) Appl. No.: 15/748,488

(22) PCT Filed: Jul. 29, 2016

(86) PCT No.: PCT/CN2016/092375
§ 371 (c)(1),
(2) Date: Jan. 29, 2018

(87) PCT Pub. No.: WO2017/016523
PCT Pub. Date: Feb. 2, 2017

(65) Prior Publication Data
US 2018/0222853 A1   Aug. 9, 2018

(30) Foreign Application Priority Data

Jul. 30, 2015 (CN) .......................... 2015 1 0461130

(51) Int. Cl.
*C07C 275/42* (2006.01)
*C07D 231/12* (2006.01)
(Continued)

(52) U.S. Cl.
CPC ............ *C07C 275/42* (2013.01); *A61P 35/02* (2018.01); *C07D 213/56* (2013.01);
(Continued)

(58) Field of Classification Search
CPC .................................................. C07C 275/42
(Continued)

(56) References Cited

FOREIGN PATENT DOCUMENTS

WO    2014/062511 A1    4/2014

OTHER PUBLICATIONS

International Search Report in PCT/CN2016/092375, dated Nov. 3, 2016, 3 pages.

*Primary Examiner* — Taofiq A Solola
(74) *Attorney, Agent, or Firm* — Kilpatrick Townsend & Stockton LLP

(57) ABSTRACT

The present application relates to compounds represented by general formula (I), general formula (II) or general formula (III), and pharmaceutically acceptable salts or hydrates thereof, preparation methods thereof, and pharmaceutical compositions thereof. The compounds represented by general formula (I), general formula (II) or general formula (III) have inhibitory activities against isocitrate dehydrogenase 2 (IDH2), thereby being capable of treating IDH2 mutation-induced cancers.

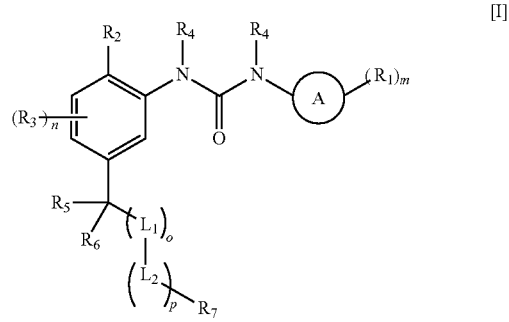

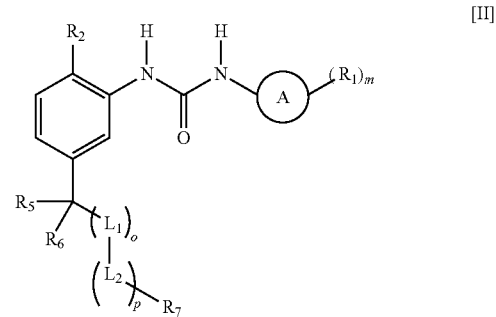

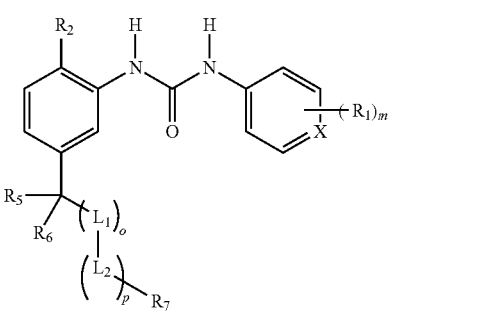

20 Claims, No Drawings

(51) Int. Cl.
*C07D 333/20* (2006.01)
*C07D 333/24* (2006.01)
*C07D 409/10* (2006.01)
*C07D 409/12* (2006.01)
*C07D 213/56* (2006.01)
*A61P 35/02* (2006.01)

(52) U.S. Cl.
CPC ......... *C07D 231/12* (2013.01); *C07D 333/20* (2013.01); *C07D 333/24* (2013.01); *C07D 409/10* (2013.01); *C07D 409/12* (2013.01)

(58) Field of Classification Search
USPC ....................................................... 514/438
See application file for complete search history.

ANTITUMOR COMPOUND TARGETING IDH2 MUTATION AND METHOD OF USE THEREOF

CROSS-REFERENCE TO RELATED APPLICATIONS

This application claims the benefit of Chinese Invention Patent Application No. 201510461130.X filed at the State Intellectual Property Office of the People's Republic of China on Jul. 30, 2015, the entire content of which is incorporated herein by reference.

TECHNICAL FIELD

The present application relates to the pharmaceutical field, and more specifically to an active compound for treating an IDH2 mutation-induced cancer and a method of using the same.

BACKGROUND

As the most important key enzyme in intracellular tricarboxylic acid cycle, IDH (full name: isocitrate dehydrogenase) can catalyze oxidative decarboxylation of isocitric acid to 2-oxoglutarate (i.e., α-ketoglutaric acid). Researches have shown that many tumors (such as, glioma, sarcoma, and acute myelocytic leukemia) have an IDH mutation at arginine residue in a catalytic center (IDH1/R132H, IDH/R140Q, and IDH2/R172K). The mutated IDH acquires a new ability to catalyze the conversion of α-ketoglutaric acid (α-KG) to 2-hydroxyglutaric acid (2-HG). Researches have shown that the structure of α-ketoglutaric acid is similar to that of 2-hydroxyglutaric acid, and 2-HG competes with α-KG, thereby reducing the activity of α-KG-dependent enzymes, and resulting in a high methylation of chromatin. Such supermethylation is considered to interfere with a normal cell differentiation, and lead to an excessive proliferation of immature cells, thereby resulting in cancers.

In 2013, Agios Pharmaceuticals reported an IDH2/R140Q inhibitor AGI-6780 (Science. 2013, 340, 622-626) and an IDH1/R132H inhibitor AGI-5198 (Science. 2013, 340, 626-630), and WO2015017821 disclosed another IDH2/R140Q inhibitor AG-221. AGI-6780 and AGI-5198 can inhibit the generation of 2-HG in cells carrying the most common IDH2 mutant and the most common IDH1 mutant, respectively. These molecules not only inhibit the generation of 2-HG, but also induce the differentiation of abnormally proliferated human cancer cells in a culture. The treatment of leukemia cells carrying the IDH2 mutant with AGI-6780, and the treatment of glioma cells carrying the IDH1 mutant with AGI-5198 both result in an enhanced expression of mature markers in these cells. Moreover, researchers have found that AGI-5198 can inhibit the growth rate of the glioma cells either by the treatment of cell cultures with AGI-5198 or by oral administration of AGI-5198 to mice with a transplanted tumour.

SUMMARY

In an aspect, the present application provides a compound of formula I:

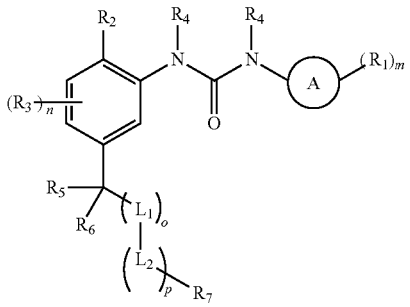

wherein:

Ring A is selected from a benzene ring or a 5- or 6-membered heteroaromatic ring containing 1 or 2 heteroatoms selected from the group consisting of N, O and S;

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ hetero alicyclic group; or two adjacent $R_1$ groups, together with the atoms of the Ring A to which they are attached, may form a 5- to 7-membered cycloalkyl ring or a 5- to 7-membered heteroalicyclic ring, and a methylene of the 5- to 7-membered cycloalkyl ring or a methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

each $R_3$ is independently selected from the group consisting of hydrogen, halogen, $C_{1-3}$haloalkyl, hydroxy, amino and $C_{1-6}$ alkyl;

each $R_4$ is independently selected from hydrogen or $C_{1-6}$ alkyl;

$R_5$ and $R_6$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or one of $R_5$ and $R_6$ is an oxygen atom of a carbonyl, and the other is absent; or $R_5$ and $R_6$, together with the carbon atom to which they are attached, form a 3- to 7-membered cycloalkyl ring or a 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

$L_1$ and $L_2$ are each independently selected from the group consisting of —C(O)—, —N($R_4$)— and —S(O)$_2$—, and $L_1$ is different from $L_2$;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl;

m and n are each independently 1, 2 or 3; and o and p are each independently selected from 0 or 1, but cannot both be 0;

or a pharmaceutically acceptable salt or hydrate thereof.

In an aspect, the present application provides a compound of formula II:

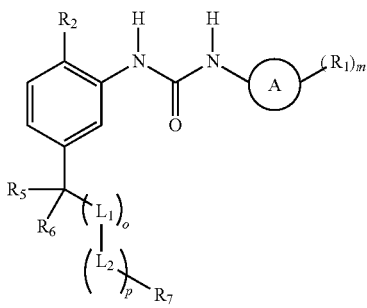

wherein:

Ring A is selected from a benzene ring or a 5- or 6-membered heteroaromatic ring containing 1 or 2 N atoms;

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of the Ring A to which they are attached, form a 5- to 7-membered cycloalkyl ring or a 5- to 7-membered heteroalicyclic ring, and a methylene of the 5- to 7-membered cycloalkyl ring or a methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

$R_5$ and $R_6$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or one of $R_5$ and $R_6$ is an oxygen atom of carbonyl, and the other is absent; or $R_5$ and $R_6$, together with the carbon atom to which they are attached, form a 3- to 7-membered cycloalkyl ring or a 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

$L_1$ and $L_2$ are each independently selected from the group consisting of —C(O)—; —N($R_4$)— and —S(O)$_2$—, wherein $L_1$ is different from $L_2$, and $R_4$ is selected from hydrogen or $C_{1-6}$ alkyl;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl;

m is 1, 2 or 3; and o and p are each independently selected from 0 or 1, but cannot both be 0;

or a pharmaceutically acceptable salt or hydrate thereof.

In an aspect, the present application provides a compound of formula III:

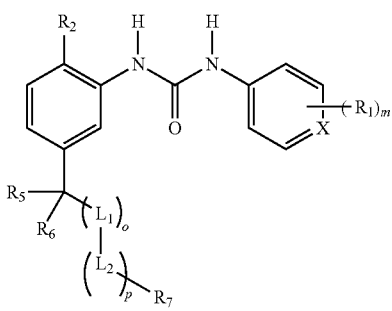

wherein:

X is selected from CH or N;

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of benzene ring or the atoms of pyridine ring to which they are attached, form a 5- to 7-membered cycloalkyl ring or a 5- to 7-membered heteroalicyclic ring, and a methylene of the 5- to 7-membered cycloalkyl ring or a methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

$R_5$ and $R_6$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or one of $R_5$ and $R_6$ is an oxygen atom of carbonyl, and the other is absent; or $R_5$ and $R_6$, together with the carbon atom to which they are attached, form a 3- to 7-membered cycloalkyl ring or a 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

$L_1$ and $L_2$ are each independently selected from the group consisting of —C(O)—; —N($R_4$)— and —S(O)$_2$—, wherein $L_1$ is different from $L_2$, and $R_4$ is selected from hydrogen or $C_{1-6}$ alkyl;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl;

m is 1, 2 or 3; and o and p are each independently selected from 0 or 1, but cannot both be 0;

or a pharmaceutically acceptable salt or hydrate thereof.

In an another aspect, the present application provides a pharmaceutical composition, comprising a compound of formula I, a compound of formula II, or a compound of formula III, or a pharmaceutically acceptable salt or hydrate thereof, and one or more pharmaceutically acceptable carriers or excipients.

In yet another aspect, the present application provides a method for treating IDH2 mutation-induced cancers, comprising administering to a subject in need thereof a compound of formula I, a compound of formula II or a compound of formula III, or a pharmaceutically acceptable salt or hydrate thereof, or a pharmaceutical composition thereof.

In yet another aspect, the present application provides a use of a compound of formula I, a compound of formula II, or a compound of formula III, or a pharmaceutically acceptable salt or hydrate thereof, or a pharmaceutical composition thereof, in the preparation of a medicament for treating IDH2 mutation-induced cancers.

In yet another aspect, the present application provides a compound of formula I, a compound of formula II, or a compound of formula III, or a pharmaceutically acceptable salt or hydrate thereof, or a pharmaceutical composition thereof, for treating IDH2 mutation-induced cancers.

In some embodiments of the present application, the IDH2 mutation is an IDH2/R140Q mutation or an IDH2/R172K mutation.

In some embodiments of the present application, the IDH2 mutation-induced cancers are selected from the group consisting of glioblastoma, myelodysplastic syndrome, myeloproliferative neoplasm, acute myelogenous leukemia, sarcoma, melanoma, non-small cell lung cancer, chondrosarcoma, bile duct cancer, and angioimmunoblastic non-Hodgkin's lymphoma.

DETAILED DESCRIPTION

In the following description, certain specific details are included to provide a thorough understanding of various disclosed embodiments. However, those skilled in the relevant art will recognize that the embodiments may be practiced without one or more of these specific details, or with other methods, components, materials, and the like.

Unless the context requires otherwise, throughout the specification and claims which follow, the term "comprise" and English variations thereof, such as "comprises" and "comprising", are to be construed in an open and inclusive sense, that is as, "including, but not limited to".

Reference throughout this specification to "one embodiment", or "an embodiment", or "another embodiment", or "some embodiments" means that a particular referent element, structure, or characteristics described in connection with the embodiment is included in at least one embodiment. Accordingly, the appearances of the phase "in one embodiment", or "in an embodiment", or "in another embodiment", or "in some embodiments" in various places throughout this specification are not necessarily all referring to the same embodiment. In addition, the particular elements, structures, or characteristics may be combined in any suitable manner in one or more embodiments.

It should be noted that, as used in this specification and the appended claims, the singular forms "a", "an" and "the" include plural referents unless the content clearly dictates otherwise. Thus, for example, reference to a reaction in which "a catalyst" is involved includes a single catalyst, or two or more catalysts. Unless otherwise explicitly specified herein, it should also be noted that the term "or" is generally employed in its sense including "and/or" unless the content clearly dictates otherwise.

Definitions

Unless stated otherwise, the following terms and phrases used herein have the following meanings. A specific term or phrase shall not be considered as unclear or indefinite when it is not specially defined. It should be understood according to its general meaning. A trade name used herein refers to a corresponding product or an active ingredient thereof.

The term "optional" or "optionally" means that the subsequently described event or circumstance may or may not occur, and that the description includes instances where said event or circumstance occurs and instances where said event or circumstance does not occurs. For example, the expression that ethyl is "optionally" substituted with halogen means that the ethyl may be unsubstituted ($CH_2CH_3$), monosubstituted (such as, $CH_2CH_2F$), poly-substituted (such as, $CHFCH_2F$, $CH_2CHF_2$, and so on) or fully substituted ($CF_2CF_3$). A person skilled in the art will understand that in respect to any group containing one or more substituents, any substitution or substitution mode that is spatially impossible and/or not synthesizable will not be introduced.

The expression $C_{m-n}$ used herein means that this moiety has m-n carbon atoms. For example, "$C_{3-10}$ cycloalkyl" means that said cycloalkyl has 3 to 10 carbon atoms. "$C_{0-6}$ alkylene" means that said alkylene has 0 to 6 carbon atoms, and the alkylene is a chemical bond when the group has 0 carbon atom.

A numerical range herein refers to each of the integers within this given range. For example, "$C_{1-10}$" means that a group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms or 10 carbon atoms.

The term "substituted" means that one or more hydrogen atoms on a given atom are replaced with a substituent, provided that the given atom has a normal valence state and the compound after substitution is stable. When the substituent is a keto (i.e., =O), which means that two hydrogen atoms are replaced, the keto substitution will not occur on an aromatic group.

When any variant (such as, R) occurs more than one times at the composition or structure of a compound, it is defined independently in each case. Therefore, for example, if a group is substituted with 0 to 2 R, then the group may be optionally substituted with at most two R, and R has an independent option in each case. Furthermore, a combination of substituents and/or variants thereof is allowed only if such combination will result in a stable compound.

Unless stated otherwise, the term "hetero" means a heteroatom or a heteroatom group (i.e., a group containing a heteroatom), i.e., atoms except for carbon and hydrogen atoms or an atom group containing such atoms. A heteroatom is independently selected from the group consisting of oxygen, nitrogen, sulfur, phosphorus, silicon, germanium, aluminum and boron. In an embodiment where two or more heteroatoms are involved, the two or more heteroatoms may be identical, or parts or all of the two or more heteroatoms may be different.

The term "halogen" or "halo" refers to any group of fluoro, chloro, bromo and iodo.

The term "hydroxy" refers to —OH.

The term "carboxy" refers to —COOH.

The term "cyano" refers to —CN.

The term "amino" refers to —$NH_2$, —NH(alkyl) and —N(alkyl)$_2$, and specific examples of an amino include, but are not limited to, —$NH_2$, —$NHCH_3$, —$NHCH(CH_3)_2$, —$N(CH_3)_2$, —$NHC_2H_5$, —$N(CH_3)C_2H_5$, and the like.

The term "alkyl" refers to a straight or branched chain saturated aliphatic hydrocarbon group consisting of carbon atoms and hydrogen atoms, such as, methyl, ethyl, propyl, butyl, pentyl, hexyl, heptyl, octyl, nonyl, and decyl. The specific alkyl includes all isomers thereof. For example, propyl includes —$CH_2CH_2CH_3$ and —$CH(CH_3)_2$. For example, butyl includes —$CH_2CH_2CH_2CH_3$, —$CH(CH_3)(CH_2CH_3)$, —$C(CH_3)_3$ and —$CH_2CH(CH_3)_2$. The term "$C_{1-8}$ alkyl" refers to an alkyl having 1 to 8 carbon atoms. The term "$C_{1-6}$ alkyl" refers to an alkyl having 1 to 6 carbon atoms. The term "$C_{1-4}$ alkyl" refers to an alkyl having 1 to 4 carbon atoms. The term "$C_{1-3}$ alkyl" refers to an alkyl having 1 to 3 carbon atoms. The "alkyl", "$C_{1-8}$ alkyl", "$C_{1-6}$ alkyl", "$C_{1-4}$ alkyl" and "$C_{1-3}$ alkyl" may be unsubstituted or substituted with one or more substituents selected from the group consisting of hydroxy, halogen and amino.

The term "alkenyl" refers to a straight or branched chain aliphatic hydrocarbon group containing 2 to 12 carbon atoms and having one or more double bonds. Examples of the alkenyl include, but are not limited to, ethenyl, allyl, propenyl, 2-butenyl and 3-hexenyl. One of the double-bonded carbon atoms may be optionally an attachment site of an alkenyl substituent.

The term "cycloalkyl ring" refers to a monocyclic saturated aliphatic hydrocarbon ring consisting solely of carbon atoms and hydrogen atoms.

The term "cycloalkyl" refers to a monocyclic saturated aliphatic hydrocarbon group consisting solely of carbon atoms and hydrogen atoms, such as, $C_{3-20}$ cycloalkyl, preferably $C_{3-6}$cycloalkyl, such as, cyclopropyl, cyclobutyl, cyclopentyl and cyclohexyl. The cycloalkyl may be unsubstituted or substituted, and the substituent includes, but is not limited to, alkyl, alkoxy, cyano, carboxy, aryl, heteroaryl, amino, halogen, sulfonyl, sulfinyl, phosphoryl, hydroxy, and the like.

The term "heteroaromatic ring" refers to a monocyclic or fused ring having 5 to 12 ring atoms, such as, 5, 6, 7, 8, 9, 10, 11 or 12 ring atoms, wherein 1, 2, 3 or 4 ring atoms are selected from the group consisting of N, O and S, and the rest of ring atom(s) is(are) carbon atom(s), and the ring has a fully conjugated pi-electron system.

The term "heteroaryl" refers to a remaining group after one hydrogen atom is removed from a "heteroaramatic ring" molecule. The heteroaryl may be unsubstituted or substituted, and the substituent includes, but is not limited to, alkyl, alkoxy, aryl, aralkyl, amino, halogen, hydroxy, cyano, nitro, carbonyl, heteroalicyclyl, and the like. Non-limiting examples of unsubstituted heteroaryl include, but are not limited to, pyrrolyl, furyl, thienyl, imidazolyl, oxazolyl, isoxazolyl, thiazolyl, isothiazolyl, oxadiazolyl, thiadiazolyl, indolyl, benzofuryl, benzothienyl, benzoxazolyl, benzothiazolyl, benzoimidazolyl, pyrazolyl, pyridyl, pyrimidyl, pyrazinyl, pyridazinyl, quinolyl, isoquinolyl, triazolyl, tetrazolyl, triazinyl, pteridinyl, etc.

The term "heteroalicyclic ring" refers to a monocyclic or fused ring having 3-12 ring atoms, for example, 3, 4, 5, 6, 7, 8, 9, 10, 11 or 12 ring atoms, among which 1 or 2 ring atoms are heteroatoms independently selected from the group consisting of N, O, and $(S)_n$ (wherein n is 0, 1 or 2), and the rest of ring atom(s) is(are) C. Such a ring may be saturated or unsaturated (e.g., having one or more double bonds), but it does not have a completely conjugated π-electron system. Examples of 3-membered saturated heteroalicyclic ring include, but are not limited to,

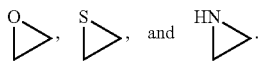

Examples of 4-membered saturated heteroalicyclic ring include, but are not limited to,

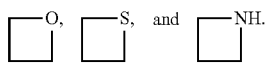

Examples of 5-membered saturated heteroalicyclic ring include, but are not limited to,

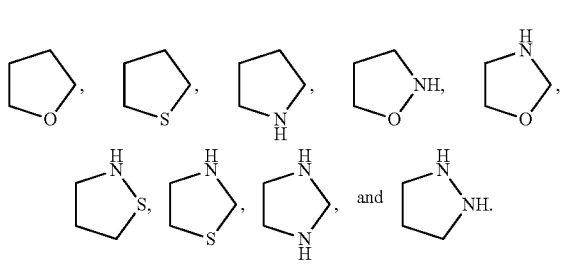

Examples of 6-membered saturated heteroalicyclic ring include, but are not limited to,

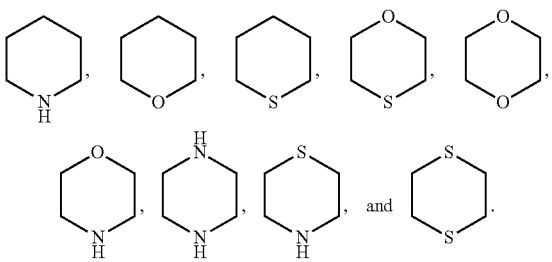

Examples of 7-membered saturated heteroalicyclic ring include, but are not limited to,

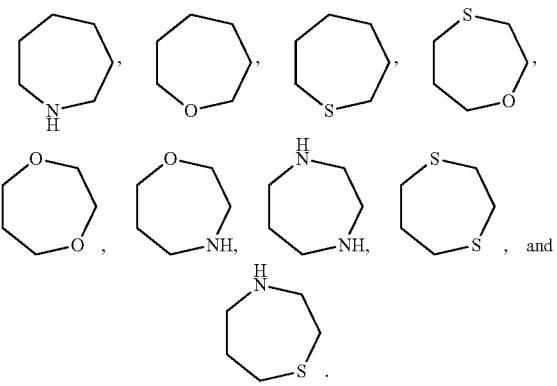

Examples of 5-membered unsaturated heteroalicyclic ring include, not are not limited to,

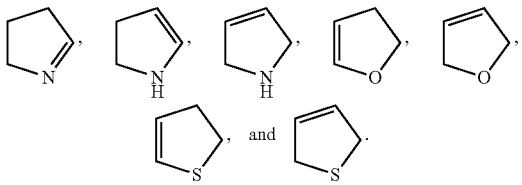

Example of 6-membered unsaturated heteroalicyclic ring include, but are not limited to,

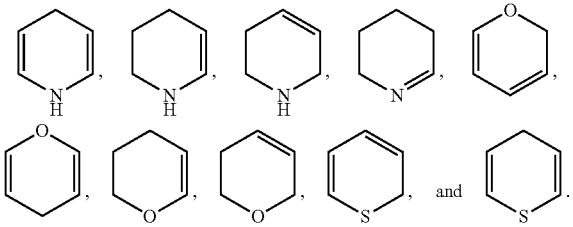

The term "heteroalicyclyl" refers to the remaining group after one hydrogen atom is removed from a "heteroalicyclic ring" molecule. Heteroalicyclyl may be unsubstituted or a hydrogen atom of heteroalicyclyl may be substituted with a substituent including, but not limited to, alkyl, alkoxy, =O, aryl, arylalkyl, —COOH, —CN, amino, halogen or hydroxy.

The term "pharmaceutically acceptable" refers to a compound, material, composition and/or dosage form that is applicable to the contact with human and animal tissues without an excessive toxicity, irritation, allergic reaction or other problems or complications in the scope of reliable medical judgment, and is commensurate with an acceptable benefits/risk ratio.

The term "pharmaceutical acceptable carrier" refers to those carriers which do not cause significant stimulation to an organism, and will not impair the bioactivity and properties of an active compound. The "pharmaceutical acceptable carrier" also refers to an inert substance which is administered together with an active ingredient and is beneficial to the administration thereof, including, but not limited to, any glidants, sweetening agents, diluents, preservatives, dyes/colorants, flavoring agents, surfactants, wetting agents, dispersants, disintegrants, suspending agents, stabilizers, isotonic agents, solvents and emulsifiers, which have been approved by the States Food and Drug Administration as being acceptable for use in humans or animals (such as livestock). Non-limiting examples of a carrier include calcium carbonate, calcium phosphate, various sugars and starches, cellulose derivatives, gelatine, vegetable oils and polyethylene glycols. Other information about the carrier may be found in Remington: The Science and Practice of Pharmacy, 21st Ed., Lippincott, Williams & Wilkins (2005), the contents of which are incorporated herein by reference.

The term "excipient" generally refers to a carrier, a diluent and/or a medium used to formulate an effective pharmaceutical composition.

As for a medicament or pharmacologically active agent, the term "effective amount" or "therapeutically effective amount" refers to the amount of a medicament or agent that is not toxic but sufficient to achieve a desired effect. For an oral dosage form in the present application, the "effective amount" of an active substance in a pharmaceutical composition refers to the amount that is required to achieve a desired effect in combination with another active substance in the composition. The effective amount may be determined individually, depending on the age and general condition of a subject as well as a specific active substance. An appropriate effective amount in a specific case may be determined by a person skilled in the art through a routine test.

The term "active ingredient", "therapeutic agent", "active substance" or "active agent" refers to a chemical entity that can effectively treat target disorders, diseases or conditions.

The term "patient" or "subject" includes a human and an animal, such as a mammal (such as a primate, cow, horse, pig, dog, cat, mouse, rat, rabbit, goat, sheep, poultry, and so on).

Compounds of General Formulae

In an aspect, the present application provides a compound of formula I:

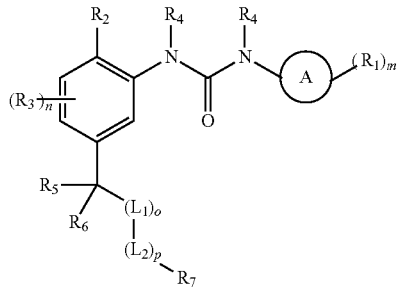

I wherein:

Ring A is selected from a benzene ring or a 5- or 6-membered heteroaromatic ring containing 1 or 2 heteroatoms selected from the group consisting of N, O and S;

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of the Ring A to which they are attached, form a 5- to 7-membered cycloalkyl ring or a 5- to 7-membered heteroalicyclic ring, and a methylene of the 5- to 7-membered cycloalkyl ring or a methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

each $R_3$ is independently selected from the group consisting of hydrogen, halogen, $C_{1-3}$haloalkyl, hydroxy, amino and $C_{1-6}$ alkyl;

each $R_4$ is independently selected from hydrogen or $C_{1-6}$ alkyl;

$R_5$ and $R_6$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or one of $R_5$ and $R_6$ is an oxygen atom of carbonyl, and the other is absent; or $R_5$ and $R_6$, together with the carbon atom to which they are attached, form a 3- to 7-membered cycloalkyl ring or a 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

$L_1$ and $L_2$ are each independently selected from the group consisting of —C(O)—; —N($R_4$)— and —S(O)$_2$—, and $L_1$ is different from $L_2$;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl;

m and n are each independently 1, 2 or 3; and o and p are each independently selected from 0 or 1, but cannot both be 0;

or a pharmaceutically acceptable salt or hydrate thereof.

In an another aspect, the present application provides a compound of formula II:

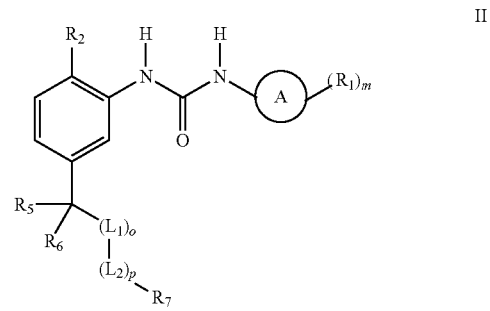

II wherein:

Ring A is selected from a benzene ring or a 5- or 6-membered heteroaromatic ring containing 1 or 2 N atoms;

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of the Ring A to which they are attached, form a 5- to 7-membered cycloalkyl ring or a 5- to 7-membered heteroalicyclic ring, and a methylene of the 5- to 7-membered cycloalkyl ring or a methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

$R_5$ and $R_5$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or one of $R_5$ and $R_6$ is an oxygen atom of carbonyl, and the other is absent; or $R_5$ and $R_6$, together with the carbon atom to which they are attached, form a 3- to 7-membered cycloalkyl ring or a 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

$L_1$ and $L_2$ are each independently selected from the group consisting of —C(O)—; —N($R_4$)— and —S(O)$_2$—, wherein $L_1$ is different from $L_2$, and $R_4$ is selected from hydrogen or $C_{1-6}$ alkyl;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl;

m is 1, 2 or 3; and o and p are each independently selected from 0 or 1, but cannot both be 0;

or a pharmaceutically acceptable salt or hydrate thereof.

In an another aspect, the present application provides a compound of formula III:

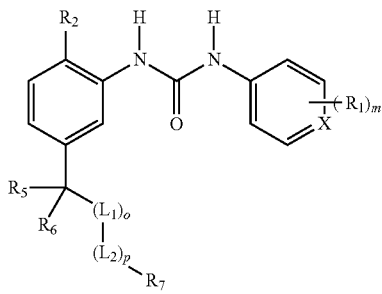

wherein:

X is selected from CH or N;

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of benzene ring or the atoms of pyridine ring to which they are attached, form a 5- to 7-membered cycloalkyl ring or a 5- to 7-membered heteroalicyclic ring, and a methylene of the 5- to 7-membered cycloalkyl ring or a methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

$R_5$ and $R_5$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or one of $R_5$ and $R_6$ is an oxygen atom of carbonyl, and the other is absent; or $R_5$ and $R_6$, together with the carbon atom to which they are attached, form a 3- to 7-membered cycloalkyl ring or a 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

$L_1$ and $L_2$ are each independently selected from the group consisting of —C(O)—; —N($R_4$)— and —S(O)$_2$—, wherein $L_1$ is different from $L_2$, and $R_4$ is selected from hydrogen or $C_{1-6}$ alkyl;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl;

m is 1, 2 or 3; and o and p are each independently selected from 0 or 1, but cannot both be 0;

or a pharmaceutically acceptable salt or hydrate thereof.

In an embodiment of the present application, the compound of formula III or the pharmaceutically acceptable salt or hydrate thereof is preferable, wherein:

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of benzene ring or the atoms of pyridine ring to which they are attached, form a 5- to 7-membered cycloalkyl ring or a 5- to 7-membered heteroalicyclic ring, and a methylene of the 5- to 7-membered cycloalkyl ring or a methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

$R_5$ and $R_5$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or one of $R_5$ and $R_6$ is an oxygen atom of carbonyl, and the other is absent; or $R_5$ and $R_5$, together with the carbon atom to which they are attached, form a 3- to 7-membered cycloalkyl ring or a 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

-($L_1$)$_o$-($L_2$)$_p$- is —C(O)—N($R_4$)—, —N($R_4$)—C(O)—, —S(O)$_2$—N($R_4$)—, —N($R_4$)—S(O)$_2$—, or —N($R_4$)—, wherein each $R_4$ is selected from hydrogen or $C_{1-6}$ alkyl;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl; and m is 1, 2 or 3.

In an embodiment of the present application, the compound of formula III or the pharmaceutically acceptable salt or hydrate thereof is preferable, wherein:

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of benzene ring or the atoms of pyridine ring to which they are attached, form a 5- to 7-membered cycloalkyl ring or a 5- to 7-membered heteroalicyclic ring, and a methylene of the 5- to 7-membered cycloalkyl ring or a methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

$R_5$ and $R_6$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or $R_5$ and $R_6$, together with the carbon atom to which they are attached, form a 3- to 7-membered cycloalkyl ring or a 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

-$(L_1)_o$-$(L_2)_p$- is —C(O)—N($R_4$)—, —N($R_4$)—C(O)—, or —N($R_4$)—, wherein each $R_4$ is selected from hydrogen or $C_{1-6}$ alkyl;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl; and m is 1, 2 or 3.

In an embodiment of the present application, the compound of formula III or the pharmaceutically acceptable salt or hydrate thereof is preferable, wherein:

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of benzene ring or the atoms of pyridine ring to which they are attached, form a 5- to 7-membered cycloalkyl ring or a 5- to 7-membered heteroalicyclic ring, and a methylene of the 5- to 7-membered cycloalkyl ring or a methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

$R_5$ and $R_5$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or $R_5$ and $R_5$, together with the carbon atom to which they are attached, form a 3- to 7-membered cycloalkyl ring or a 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

-$(L_1)_o$-$(L_2)_p$- is —C(O)—N($R_4$)—, or —N($R_4$)—C(O)—, wherein each $R_4$ is selected from hydrogen or $C_{1-6}$ alkyl;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl; and m is 1, 2 or 3.

In an embodiment of the present application, the compound of formula III or the pharmaceutically acceptable salt or hydrate thereof is preferable, wherein m is 1 or 2; each $R_1$ is independently selected from the group consisting of halogen, monofluoromethyl, difluoromethyl, trifluoromethyl, monofluoroethyl, difluoroethyl, trifluoroethyl, tetrafluorethyl, pentafluorethyl, monochloromethyl, dichloromethyl and trichloromethyl; or two adjacent $R_1$ groups, together with the atoms of benzene ring or the atoms of pyridine ring to which they are attached, form a 5- to 7-membered heteroalicyclic ring, and a methylene of the 5- to 7-membered heteroalicyclic ring may optionally further form one carbonyl; and more preferably, m is 1 or 2; each $R_1$ is independently selected from fluoro or trifluoromethyl; or two adjacent $R_1$ groups, together with the atoms of the benzene ring or the atoms of the pyridine ring to which they are attached, form a 5-membered nitrogen-containing heteroalicyclic ring, and a methylene of the 5-membered nitrogen-containing heteroalicyclic ring may optionally form one carbonyl.

In an embodiment of the present application, the compound of formula III or the pharmaceutically acceptable salt or hydrate thereof is preferable, wherein $R_2$ is selected from the group consisting of phenyl, furyl, thienyl, pyrrolyl, pyrazolyl, imidazolyl, pyridyl, pyrimidyl, pyridazinyl, pyrazinyl, thiazolyl, isothiazolyl, oxazolyl, isoxazolyl, tetrazolyl and triazinyl, and may be optionally substituted with one or more $R_8$; each $R_8$ is independently selected from $C_{1-3}$ haloalkyl or $C_{1-6}$ alkyl; and more preferably, $R_2$ is selected from the group consisting of phenyl, thienyl, pyrazolyl and pyridinyl, and may be optionally substituted with one or more $R_8$; and each $R_8$ is independently selected from trifluoromethyl or methyl.

In an embodiment of the present application, the compound of formula III or the pharmaceutically acceptable salt or hydrate thereof is preferable, wherein $R_5$ and $R_6$ are each independently selected from the group consisting of hydrogen, fluoro, chloro, bromo, amino, methyl, ethyl, propyl and isopropyl, or $R_5$ and $R_6$, together with the carbon atom to which they are attached, form cyclopropane, cyclobutane, cyclopentane, cyclohexane, piperidine or pyrrolidine; and more preferably, $R_5$ and $R_6$ are each independently selected from the group consisting of hydrogen, fluoro, amino, methyl and ethyl, or $R_5$ and $R_6$, together with the carbon atom to which they are attached, form cyclopropane, cyclobutane or piperidine.

In an embodiment of the present application, the compound of formula III or the pharmaceutically acceptable salt or hydrate thereof is preferable, wherein -$(L_1)_o$-$(L_2)_p$- is —C(O)—NH—, or —NH—C(O)—.

In an embodiment of the present application, the compound of formula III or the pharmaceutically acceptable salt or hydrate thereof is preferable, wherein $R_7$ is selected from the group consisting of methyl, ethyl, propyl, butyl, pentyl, cyclopropyl, cyclobutyl, cyclopentyl, cyclohexyl and $C_{3-6}$ heteroalicyclyl containing one heteroatom selected from O or N, and may be optionally substituted with one or more $R_9$; each $R_9$ is independently selected from the group consisting of halogen, hydroxy, cyano and $C_{1-6}$ alkyl; and more preferably, $R_7$ is selected from the group consisting of ethyl, propyl, butyl, pentyl, cyclopropyl, cyclobutyl, oxetanyl and azetidinyl, and may be optionally substituted with 1 to 3 $R_9$; and each $R_9$ is independently selected from the group consisting of fluoro, hydroxy, cyano and methyl.

In an embodiment of the present application, the following compounds:

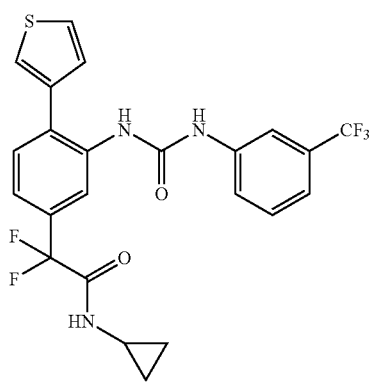 [SMILES: O=C(Nc1cccc(C(F)(F)F)c1)Nc1cc(C(F)(F)C(=O)NC2CC2)ccc1-c1ccsc1]
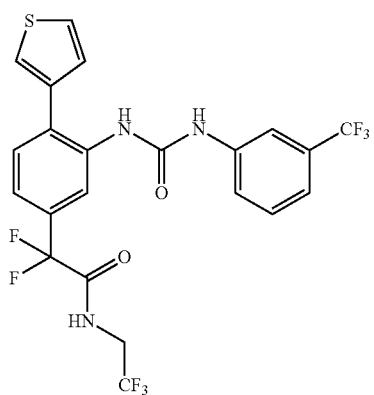 [SMILES: O=C(Nc1cccc(C(F)(F)F)c1)Nc1cc(C(F)(F)C(=O)NCC(F)(F)F)ccc1-c1ccsc1]
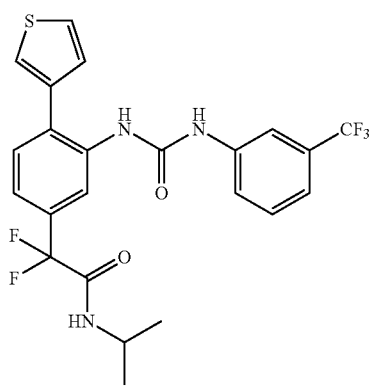 [SMILES: CC(C)NC(=O)C(F)(F)c1ccc(-c2ccsc2)c(NC(=O)Nc2cccc(C(F)(F)F)c2)c1]
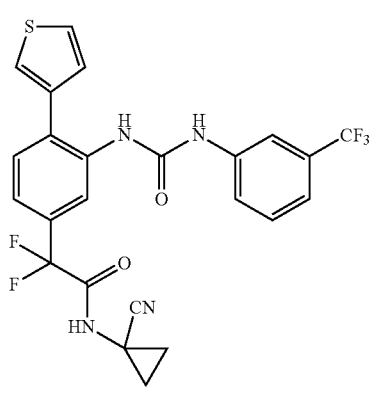
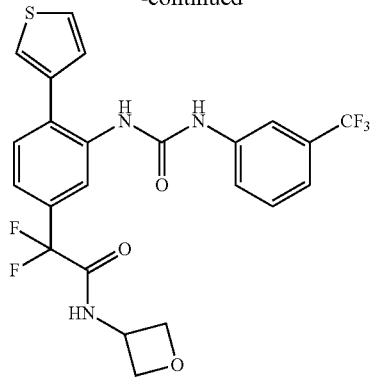
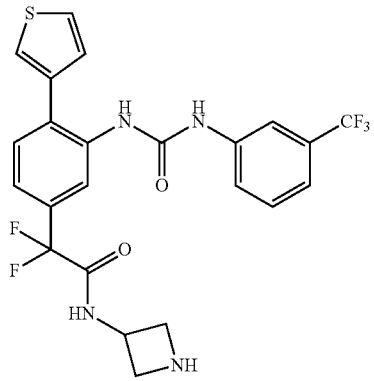
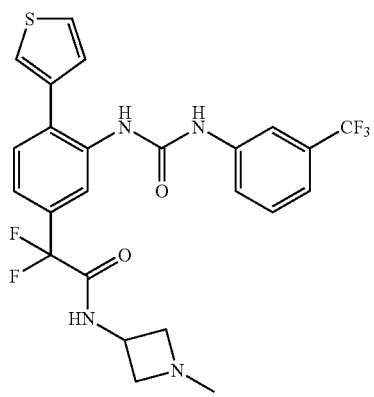
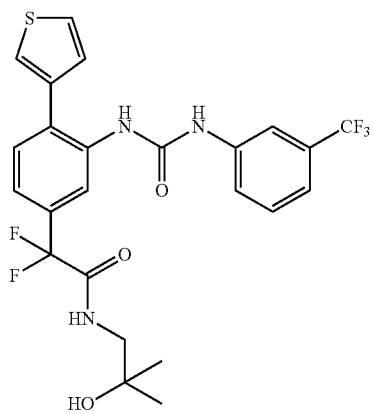

-continued
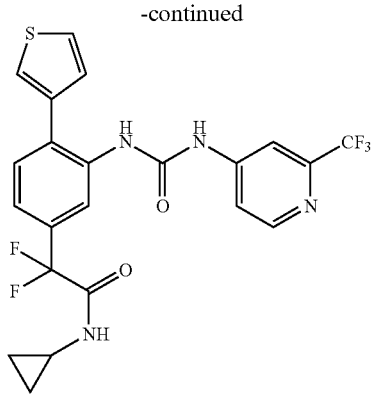
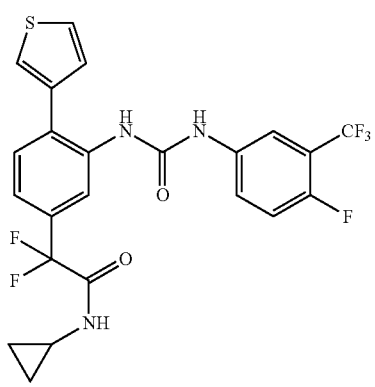
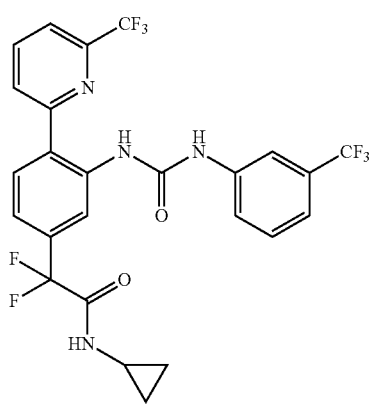
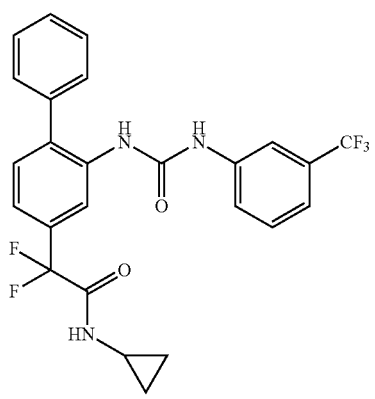
-continued
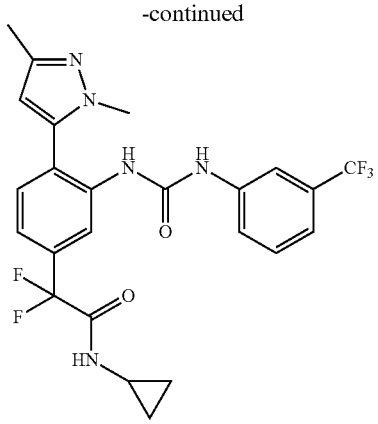
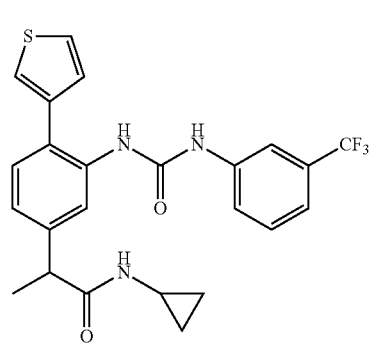
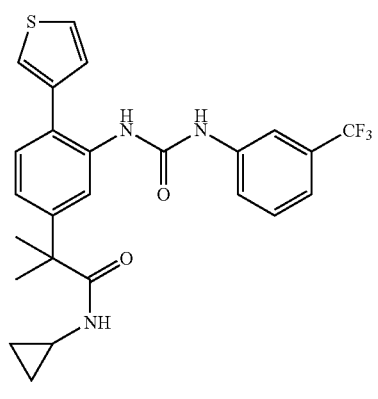
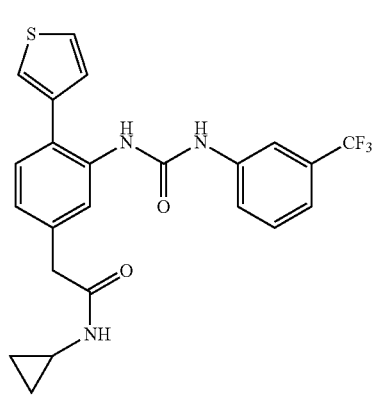

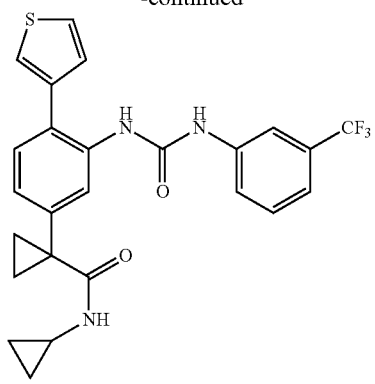
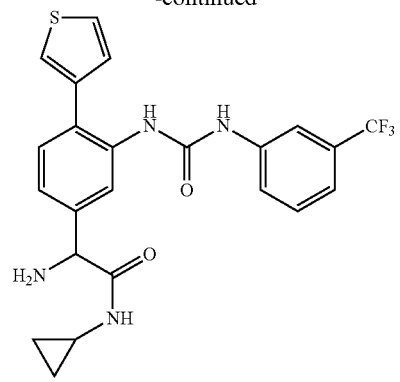
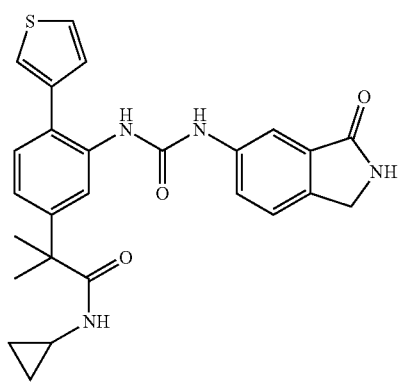
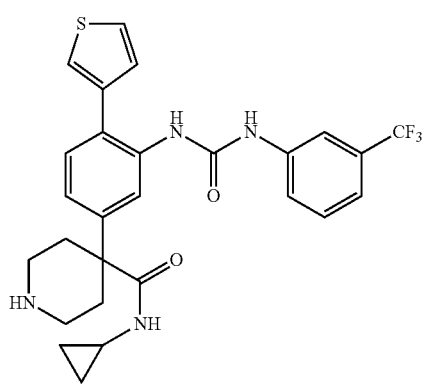
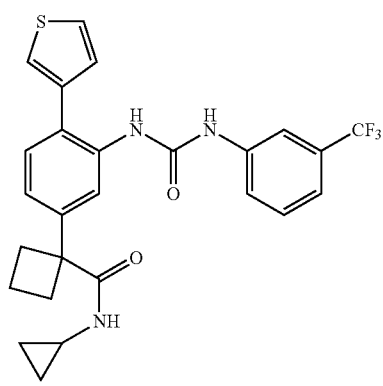
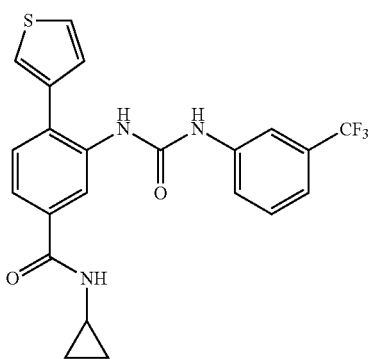
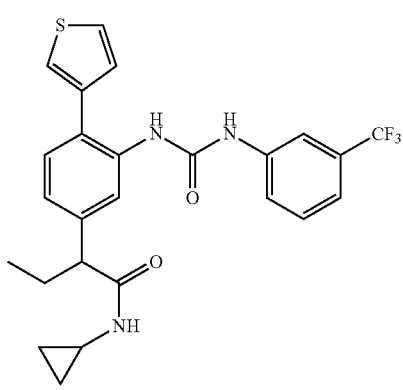
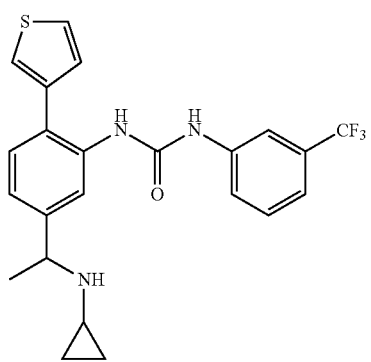

-continued

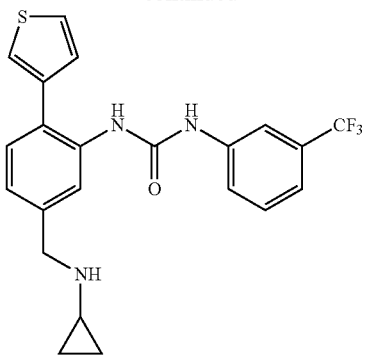

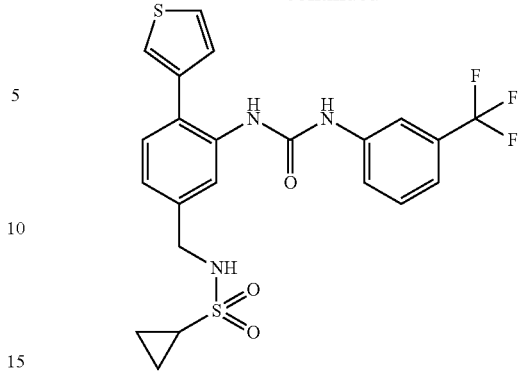

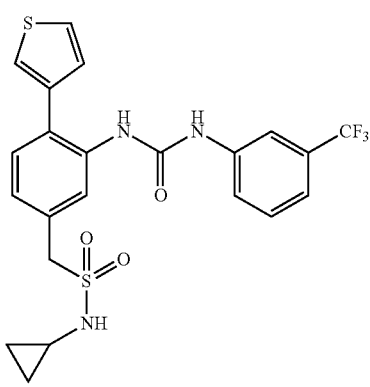

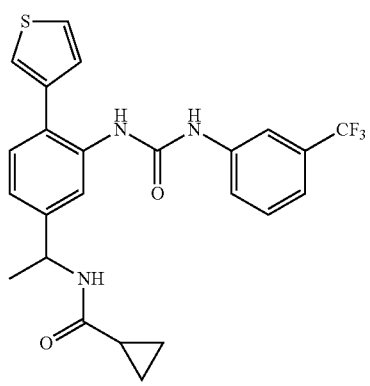

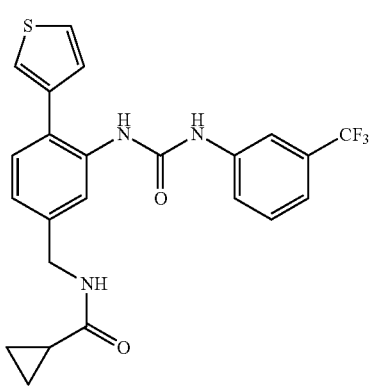

or pharmaceutically acceptable salts or hydrates thereof are preferable.

Pharmaceutically acceptable salts of the compound of formula I, the compound of formula II, or the compound of formula III may refer to, for example, metal salts, ammonium salts, salts formed with organic bases, salts formed with inorganic acids, salts formed with organic acids, salts formed with basic or acidic amino acids, and the like. Non-limiting examples of the metal salts include, but are not limited to, alkaline metal salts, such as, sodium salts, potassium salts, and so on; alkaline earth metal salts, such as, calcium salts, magnesium salts and barium salts; aluminium salts, and the like. Non-limiting examples of the salts formed with organic bases include, but are not limited to, salts formed with trimethylamine, triethylamine, pyridine, methylpyridine, 2,6-dimethylpyridine, ethanolamine, diethanolamine, triethanolamine, cyclohexylamine, dicyclohexylamine, and the like. Non-limiting examples of the salts formed with inorganic acids include, but are not limited to, salts formed with hydrochloric acid, hydrobromic acid, nitric acid, sulfuric acid, phosphoric acid, and the like. Non-limiting examples of the salts formed with organic acids include, but are not limited to, salts formed with formic acid, acetic acid, trifluoroacetic acid, fumaric acid, oxalic acid, malic acid, maleic acid, tartaric acid, citric acid, succinic acid, methanesulfonic acid, benzenesulfonic acid, p-toluene sulfonic acid, and the like. Non-limiting examples of the salts formed with basic amino acids include, but are not limited to, salts formed with arginine, lysine, ornithine, and the like. Non-limiting examples of the salts formed with acidic amino acids include, but are not limited to, salts formed with aspartic acid, glutamic acid, and the like.

The pharmaceutically acceptable salts of the present application may be prepared from a parent compound containing an acidic or basic group through a conventional chemical method. In general, such salts may be prepared through the reaction of a compound in the form of a free acid or a free base with a stoichiometric appropriate base or acid in water, an organic solvent or a mixture of the both. Generally, a non-aqueous medium, such as, ether, ethyl acetate, ethanol, isopropanol, acetonitrile, and the like, is preferable.

The compound of formula I, the compound of formula II, or the compound of formula III of the present application may exist in a non-solvated or solvated form, including a hydrate form. In general, the solvated form is equivalent to the non-solvated form, both of which are encompassed within the scope of the present application. The compound of formula I, the compound of formula II or the compound of formula III of the present application may exist in a polymorphic or amorphous form.

The compound of formula I, the compound of formula II, or the compound of formula III of the present application may have an asymmetric carbon atom (optical center) or a double bond. Racemates, diastereomers, geometric isomers and individual isomers all are encompassed within the scope of the present application.

The graphic representations of racemic, ambiscalemic and scalemic, or enantiomerically pure compounds in the present application are derived from Maehr, *J. Chem. Ed.* 1985, 62: 114-120. Unless stated otherwise, solid and dashed wedges are used to denote the absolute configuration of a stereocenter. When the compound of formula I, the compound of formula II, or the compound of formula III of the present application contains olefinic double bond(s) or other geometric asymmetric center(s), unless stated otherwise, E and Z geometric isomers are also encompassed. Likewise, all the tautomeric forms are also encompassed within the scope of the present application.

The compound of formula I, the compound of formula II, or the compound of formula III of the present application may have special geometric or stereoisomeric forms. Such compounds, including cis- and trans-isomers, (−)- and (+)- enantiomers, (R)- and (S)-enantiomers, diastereomers, (D)- isomers, (L)-isomers, and a racemic mixture and other mixtures thereof, such as, enantiomerically or diastereoisomerically enriched mixtures, can be expected, all of which are encompassed within the scope of the present application. Additional asymmetric carbon atoms may exist in a substituent, such as alkyl and others. All these isomers and mixtures thereof are also encompassed within the scope of the present application.

Optically active (R)- and (S)-isomers and D and L isomers may be prepared by a chiral synthesis, or a chiral reagent, or other conventional techniques. If an enantiomer of a compound in the present application is desired, it may be prepared by an asymmetric synthesis or derivatization with a chiral auxiliary, in which the desired pure enantiomer is prepared by separating the resulting diastereomer mixture, and cleaving the auxiliary group. Alternatively, a molecule containing a basic functional group (such as, amino) or an acidic functional group (such as, carboxy) forms a diastereomeric salt with an appropriate acid or base having an optical activity, and then the diastereomeric resolution is performed with fractional crystallization or chromatography which is well-known to a person skilled in the art so as to recover a pure enantiomer. In addition, separation of enantiomers and diastereomers is usually carried out through chromatography that uses a chiral stationary phase, and is optionally combined with a chemical derivatization method (for example, forming carbamate from an amine).

The compound of formula I, the compound of formula II, or the compound of formula III of the present application may contain an atomic isotope at a non-natural ratio at one or more atoms constituting said compound. For example, the compound may be isotopically labelled with radioisotopes, such as tritium ($^3$H), iodine-125 ($^{125}$I) or carbon-14 ($^{14}$C). All the isotopic variations of the compound of formula I, the compound of formula II, or the compound of formula III of the present application, whether radioactive or not, are encompassed within the scope of the present application.

The compound of formula I, the compound of formula II, or the compound of formula III, or the pharmaceutically acceptable salt or hydrate thereof provided by the present application has very good inhibitory activity against IDH2, a very good metabolism in vivo, and a very long half-life in vivo, and is promising to become a drug applicable to the treatment of IDH2 mutation-reduced cancers.

Pharmaceutical Composition

In an another aspect, the present application provides a pharmaceutical composition, comprising a compound of formula I, a compound of formula II, or a compound of formula III, or a pharmaceutically acceptable salt or hydrate thereof, and one or more pharmaceutically acceptable carriers or excipients. The pharmaceutical composition of the present application may further comprise one or more additional therapeutic agents.

The pharmaceutical composition of the present application may be prepared by combining the compound of formula I, the compound of formula II, or the compound of formula III, or the pharmaceutically acceptable salt or hydrate thereof of the present application, with appropriate pharmaceutically acceptable carriers or excipients. For example, the pharmaceutical composition of the present application may be formulated into solid, semi-solid, liquid or gaseous formulations, such as, tablets, pills, capsules, powders, granules, ointments, emulsions, suspensions, solutions, suppositories, injections, inhalants, gels, microspheres, aerosols, and the like.

Typical routes of the administration of the compound of formula I, the compound of formula II, or the compound of formula III, or the pharmaceutically acceptable salt or hydrate thereof, or the pharmaceutical composition thereof of the present application include, but are not limited to, oral, rectal, transmucosal, enteral, or topical, transdermal, inhalation, parenteral, sublingual, intravaginal, intranasal, intraocular, intraperitoneal, intramuscular, subcutaneous, and intravenous administration.

The pharmaceutical composition of the present application may be manufactured by using a method well-known to a person skilled in the art, such as conventional mixing method, dissolution method, granulation method, dragee manufacture method, grinding method, emulsification method, lyophilization method, and the like.

For oral administration, the pharmaceutical composition may be prepared by mixing the compound of formula I, the compound of formula II, or the compound of formula III, or the pharmaceutically acceptable salt or hydrate thereof, with pharmaceutically acceptable carriers or excipients well-known to a person skilled in the art. Such carriers or excipients enable the compound of formula I, the compound of formula II, or the compound of formula III, or the pharmaceutically acceptable salt or hydrate thereof of the present application, to be formulated into tablets, pills, lozenges, dragees, capsules, liquids, gels, slurries, suspensions, and the like, which are used for oral administration to a patient.

A solid oral pharmaceutical composition may be prepared by a conventional mixing, filling or tabletting method. For example, it may be prepared mixing the compound of formula I, the compound of formula II, or the compound of formula III, or the pharmaceutically acceptable salt or hydrate thereof, with a solid excipient, optionally grinding the resulting mixture, if necessary, adding other appropriate auxiliaries, and then processing the mixture into granules to obtain the cores of a tablet or dragee. Appropriate auxiliaries include, but are not limited to, binders, diluents, disintegrating agents, lubricants, glidants, sweetening agents, flavoring agents, and the like, such as, microcrystalline cellulose, glucose solution, acacia mucilage, gelatin solution, sucrose and starch paste; talc, starch, magnesium stearate, calcium stearate, or stearic acid; lactose, sucrose, starch, mannitol, sorbitol, or dicalcium phosphate; silicon dioxide; cross-linked sodium carboxymethyl cellulose, pregelatinized starch, sodium starch glycollate, alginic acid, corn starch, potato starch, methyl cellulose, agar, carboxymethyl cellulose, cross-linked polyvinylpyrrolidone, and the like. The cores of a dragee may be optionally coated by using a generally well-known method in the pharmaceutical field, especially using an enteric coating.

The pharmaceutical composition of the present application may also be adapted for parenteral administration, such as, a sterile solution, a suspension or a lyophilized product in an appropriate unit dosage form. An appropriate excipient, such as a filler, a buffering agent, or a surfactant, may be used to formulate dosage forms suitable for parenteral administration.

Therapeutic Use

In an another aspect, the present application provides a method for treating IDH2 mutation-induced cancers, comprising administering to a subject in need thereof a compound of formula I, a compound of formula II, or a compound of formula III, or a pharmaceutically acceptable salt or hydrate thereof, or a pharmaceutical composition thereof.

In yet another aspect, the present application provides a use of a compound of formula I, a compound of formula II, or a compound of formula III, or a pharmaceutically acceptable salt or hydrate thereof, or a pharmaceutical composition thereof, in the preparation of a medicament for treating IDH2 mutation-induced cancers.

In yet another aspect, the present application provides a compound of formula I, a compound of formula II, or a compound of formula III, or a pharmaceutically acceptable salt or hydrate thereof, or a pharmaceutical composition thereof, for use in the treatment of IDH2 mutation-induced cancers.

In some embodiments of the present application, the IDH2 mutation is an IDH2/R140Q mutation or an IDH2/R172K mutation.

In some embodiments of the present application, the IDH2 mutation-induced cancers are selected from the group consisting of glioblastoma (neuroglioma), myelodysplastic syndrome (MDS), myeloproliferative neoplasm (MPN), acute myelogenous leukemia (AML), sarcoma, melanoma, non-small cell lung cancer, chondrosarcoma, bile duct cancer and angioimmunoblastic non-Hodgkin's lymphoma (NHL). In preferable embodiments, the cancers to be treated are selected from the group consisting of neuroglioma, myelodysplastic syndrome (MDS), myeloproliferative neoplasm (MPN), acute myelogenous leukemia (AML), melanoma, chondrosarcoma, angioimmunoblastic non-Hodgkin's lymphoma (NHL), and the like, preferably including acute myelogenous leukemia (AML) or sarcoma.

The compound of formula I, the compound of formula II, or the compound of formula III, or the pharmaceutically acceptable salt or hydrate thereof, or the pharmaceutical composition thereof of the present application may be administered through any suitable route and method, for example, through oral administration or parenteral administration (such as, intravenous administration). The compound of formula I, the compound of formula II, or the compound of formula III, or the pharmaceutically acceptable salt or hydrate thereof, or the pharmaceutical composition thereof of the present application may be administered to a subject in need thereof at a therapeutically effective amount. The compound of formula I, the compound of formula II, or the compound of formula III is administered at a dosage of about 0.0001 to 20 mg/kg body weight/day, such as, about 0.001 to 10 mg/kg body weight/day.

The administration frequency of the compound of formula I, the compound of formula II, or the compound of formula III, or the pharmaceutically acceptable salt or hydrate thereof of the present application depends on the requirements of a patient subject, such as, once daily or twice daily, or more times daily. The administration may be intermittent. For example, a patient receives a daily dosage of the compound of formula I, the compound of formula II, or the compound of formula III, or the pharmaceutically acceptable salt or hydrate thereof during a period of several days, but then does not receive a daily dosage of the compound of formula I, the compound of formula II, or the compound of formula III, or the pharmaceutically acceptable salt or hydrate thereof during a period of several or more days.

Preparation

The compound of formula I, the compound of formula II, or the compound of formula III of the present application can be prepared through various synthetic methods well-known to a person skilled in the art, including specific embodiments illustrated below, embodiments formed by a combination of such specific embodiments with other chemical synthetic methods, and equivalents well-known to a person skilled in the art. Preferable embodiments include, but are not limited to, the working Examples in the present application.

A chemical reaction in the specific embodiments of the present application is carried out in an appropriate solvent which should be suitable for the chemical change(s) and required reagent(s) and material(s) in the present application. In order to obtain the compound of formula I, the compound of formula II, or the compound of formula III of the present application, a person skilled in the art sometimes needs to make a modification or selection to synthesis step(s) or reaction procedure(s) on the basis of the existing embodiments.

A compound of formula IV of the present application may be prepared by a person skilled in the field of organic synthesis using a standard method through the following scheme:

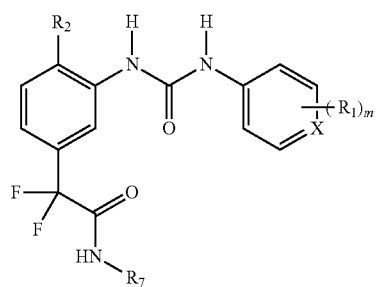

IV wherein X, $R_1$, $R_2$, $R_7$ and m are defined the same as in the compound of formula III;

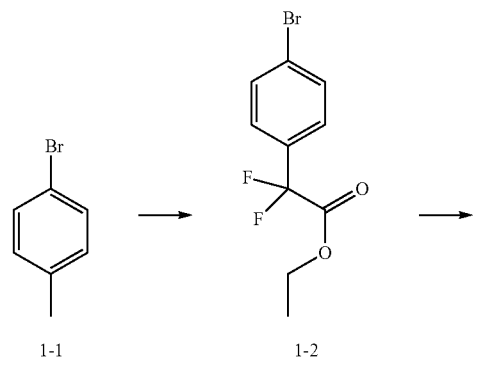

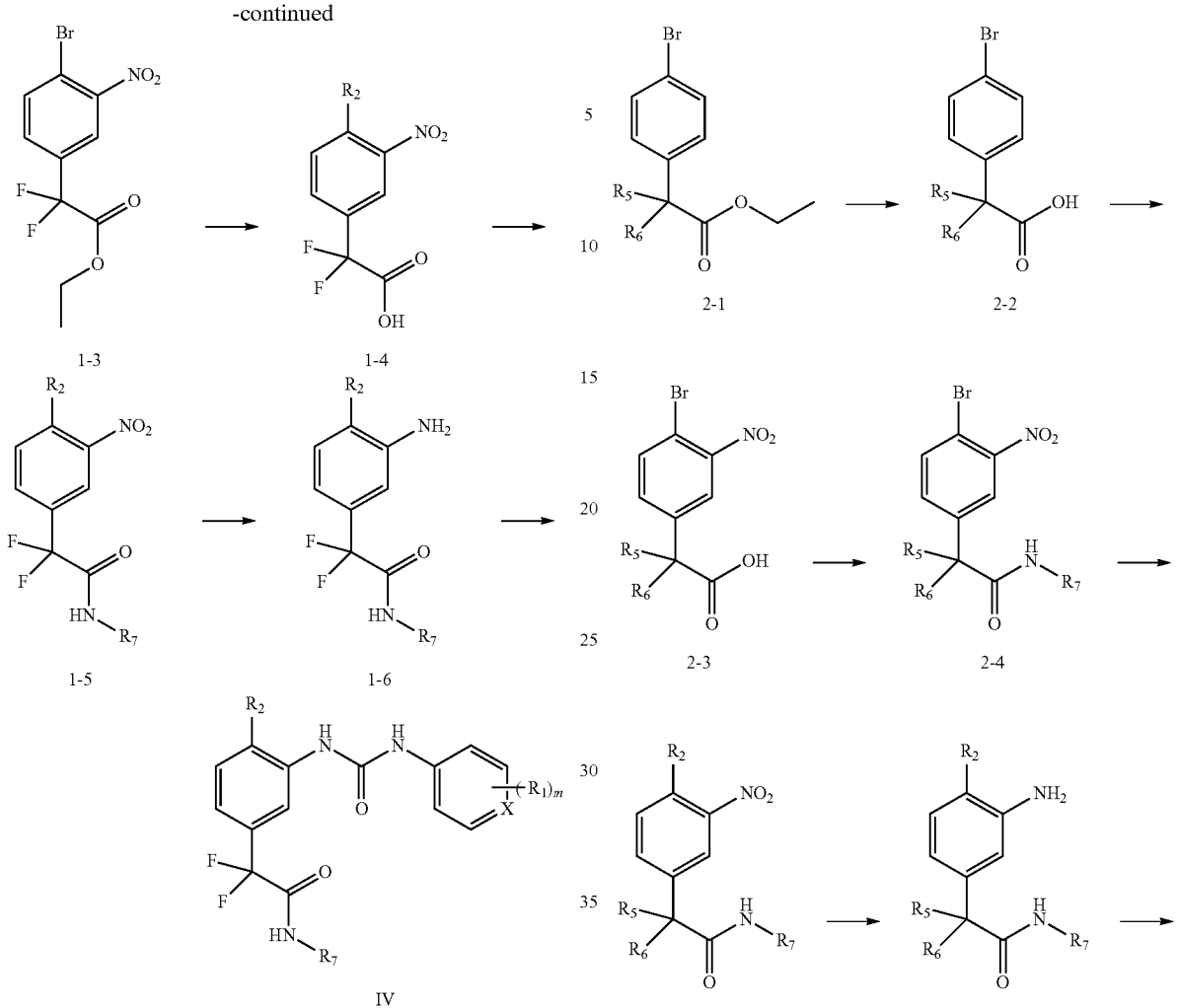

Compound 1-2 is prepared by substituting 4-bromo-iodobenzene with ethyl difluorobromoacetate, which is then nitrated to obtain compound 1-3; the bromine atom of compound 1-3 is substituted with $R_2$ group, and meanwhile the acetate thereof is hydrolyzed to obtain compound 1-4, which is then amidated to obtain compound 1-5; and compound 1-5 is reduced to obtain compound 1-6, which then reacts with a substituted isocyanate to obtain the compound of formula IV.

A compound of formula V of the present application may be prepared by a person skilled in the field of organic synthesis using a standard method through the following scheme:

wherein X, $R_1$, $R_2$, $R_5$, $R_8$, $R_7$ and m are defined the same as in the compound of formula III;

Compound 2-1 is hydrolyzed to obtain compound 2-2, which is then nitrated to obtain compound 2-3; compound 2-3 is amidated to obtain compound 2-4, the bromine atom of which is substituted with $R_2$ group to obtain compound 2-5; and compound 2-5 is reduced to obtain compound 2-6, which then reacts with a substituted isocyanate to obtain the compound of formula V.

A compound of formula VI of the present application may be prepared by a person skilled in the field of organic synthesis using a standard method through the following scheme:

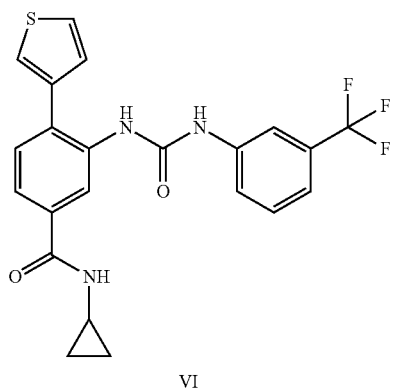

VI

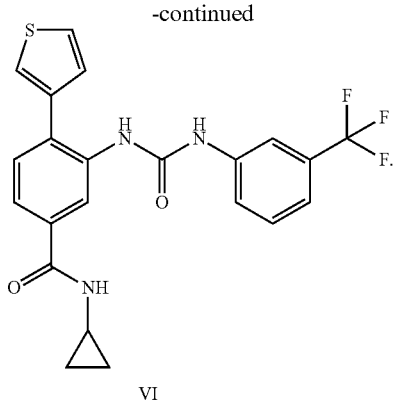

VI

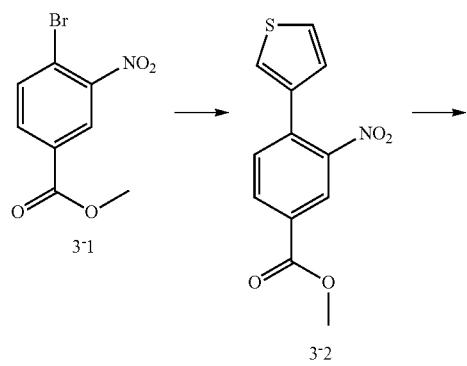

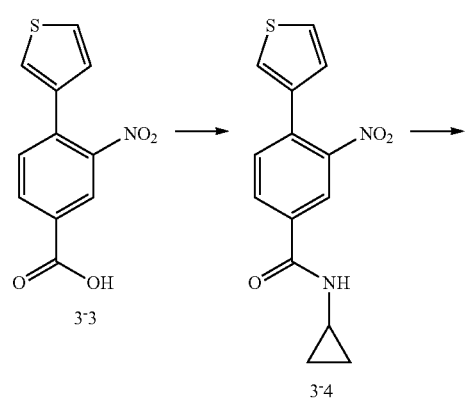

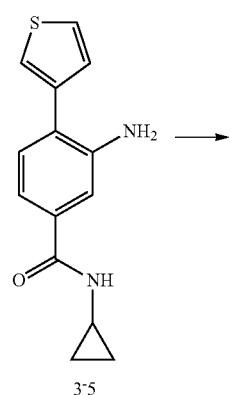

Compound 3-1 reacts with 3-thienylboric acid to obtain compound 3-2, which is then hydrolyzed to obtain compound 3-3; compound 3-3 reacts with cyclopropylamine to obtain compound 3-4, which is then reduced to obtain compound 3-5; and a urea-forming reaction occurs between compound 3-5 and 3-trifluoromethylphenyl isocyanate to obtain the compound of formula VI.

A compound of formula VII of the present application may be prepared by a person skilled in the field of organic synthesis using a standard method through the following scheme:

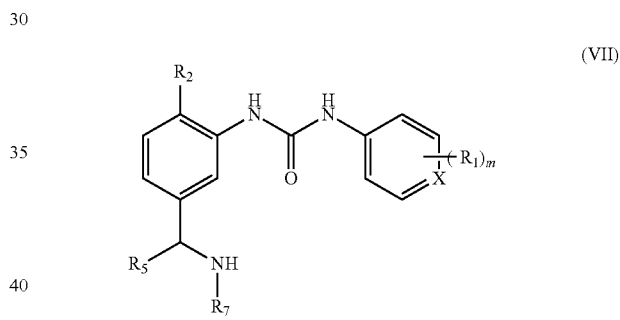

wherein X, $R_1$, $R_2$, $R_5$, $R_7$ and m are defined the same as in the compound of formula III;

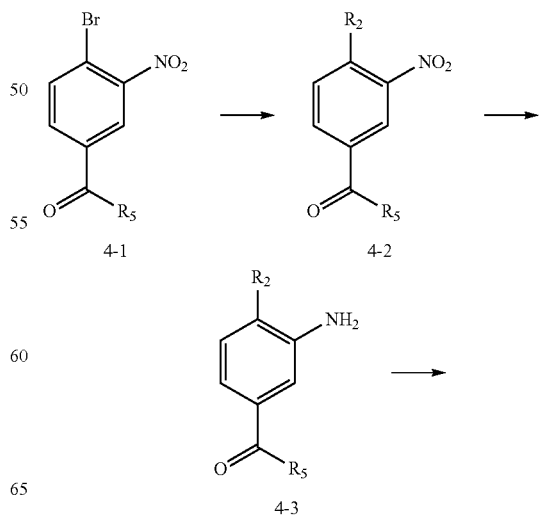

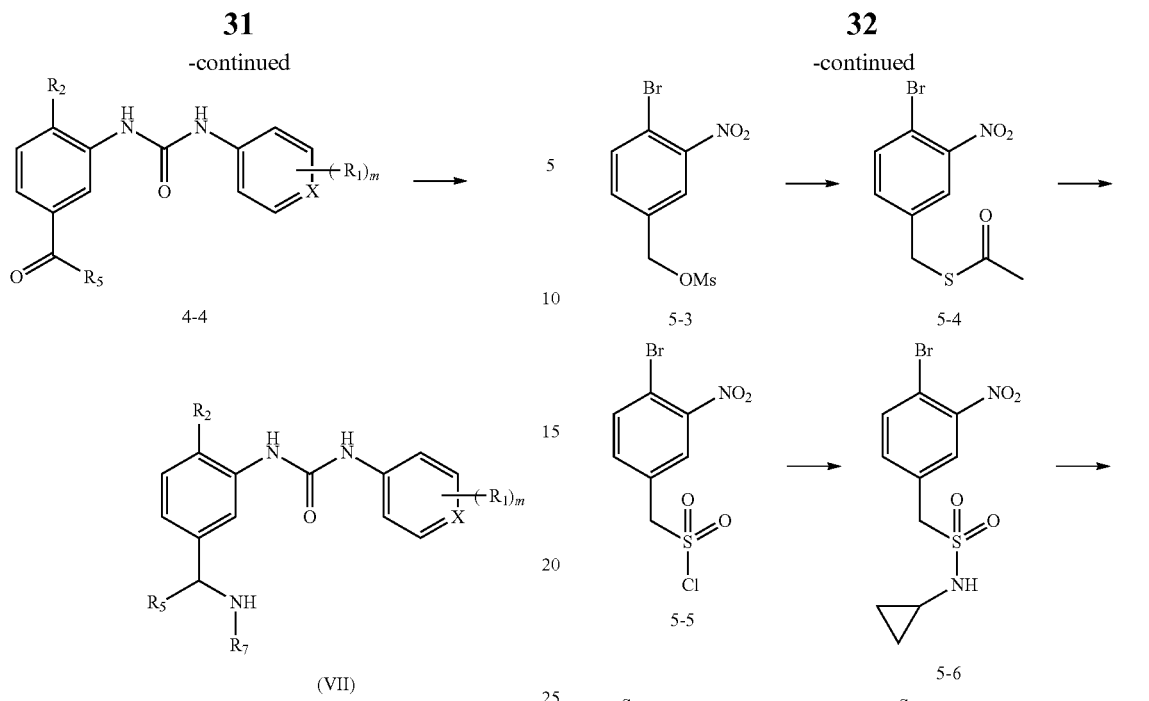

The bromine atom of compound 4-1 is substituted with R₂ group to obtain compound 4-2, which is then reduced to obtain compound 4-3; compound 4-3 reacts with a substituted isocyanate to obtain compound 4-4; and compound 4-4 reacts with an amine substituted with R₇ to obtain the compound of formula VII.

A compound of formula VIII of the present application may be prepared by a person skilled in the field of organic synthesis using a standard method through the following scheme:

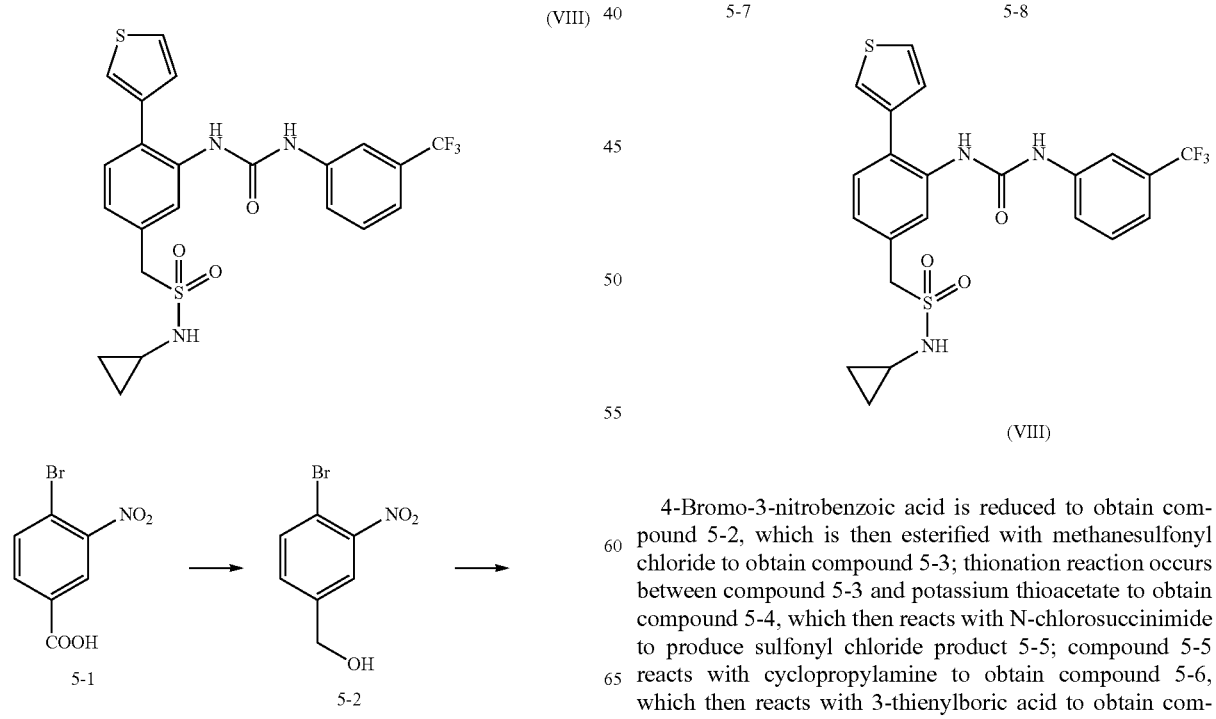

4-Bromo-3-nitrobenzoic acid is reduced to obtain compound 5-2, which is then esterified with methanesulfonyl chloride to obtain compound 5-3; thionation reaction occurs between compound 5-3 and potassium thioacetate to obtain compound 5-4, which then reacts with N-chlorosuccinimide to produce sulfonyl chloride product 5-5; compound 5-5 reacts with cyclopropylamine to obtain compound 5-6, which then reacts with 3-thienylboric acid to obtain compound 5-7; compound 5-7 is reduced to obtain compound 5-8, and a urea-forming reaction occurs between compound 5-8 and 3-trifluoromethylphenyl isocyanate to obtain the compound of formula VIII.

A compound of formula IX of the present application may be prepared by a person skilled in the field of organic synthesis using a standard method through the following scheme:

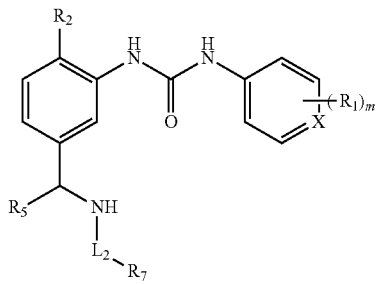

(VIII)

wherein X, $R_1$, $R_2$, $R_5$, $R_7$, $L_2$ and m are defined the same as in the compound of formula III;

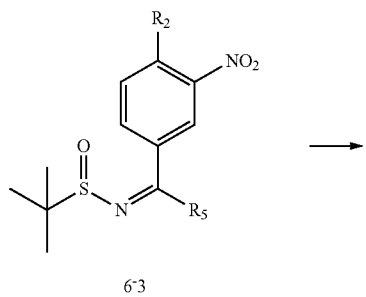

6-1

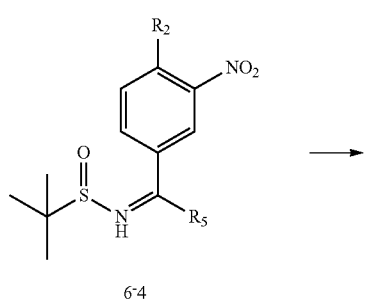

6-3

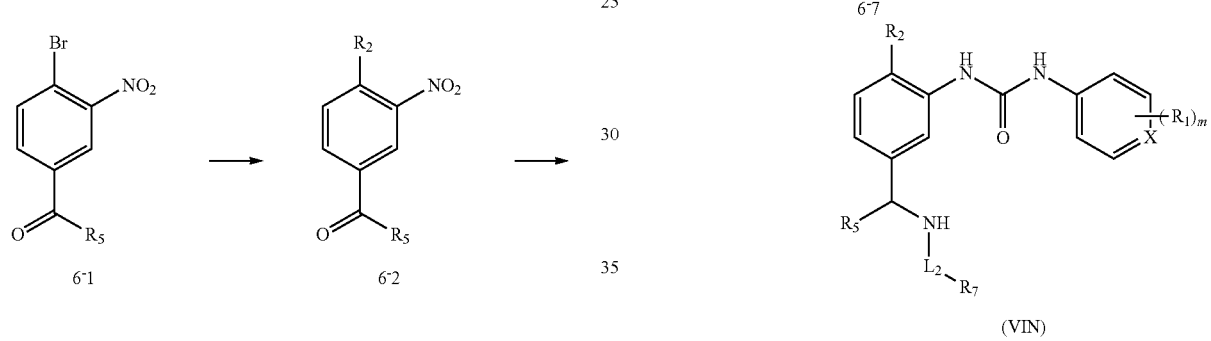

(IX)

The bromine atom of compound 6-1 is substituted with $R_2$ group to obtain compound 6-2, which then reacts with tert-butyl sulfinamide to obtain compound 6-3; the imino group of compound 6-3 is reduced to obtain compound 6-4; the sulfonamide group of compound 6-4 is hydrolyzed to obtain compound 6-5, which is then amidated to obtain compound 6-6; compound 6-6 is reduced to obtain compound 6-7, which then reacts with a substituted isocyanate to obtain the compound of formula IX.

EXAMPLES

The following specific examples are provided to enable those skilled in the art to more clearly understand and practice the invention. They should not be construed as a limitation to the scope of the invention, but as mere illustrations and typical representatives of the invention. Those skilled in the art will understand that there are other synthetic routes involved for preparing the compounds of the present application, and ones provided below are non-limiting examples.

All operations involving raw materials that are susceptible to oxidation or hydrolysis are carried out under a nitrogen protection atmosphere. Unless indicated otherwise, raw materials used in the present application are commercially available and directly used without further purification.

Column chromatography was performed using silica gel (200-300 mesh) produced by Qingdao Chemical Co., Ltd.

Thin Layer Chromatography was performed using prefabricated plates (silica gel 60 $PF_{254}$, 0.25 mm) manufactured by E. Merck. Separation of chiral compounds and measurement of enantiomeric excess (ee) were performed using the Agilent LC 1200 series (column: CHIRALPAK AD-H, Ø4.6×250 mm, 5 microns, 30° C.). NMR spectrum was performed using Varian VNMRS-400 nuclear magnetic resonance spectrometer; and LC/MS was performed using FINNIGAN Thermo LCQ Advantage MAX, Agilent LC 1200 series (column: Waters Symmetry C18, Ø4.6×50 mm, 5 micron, 35° C.), and ESI (+) ion mode.

EXPERIMENT PART

Example 1: N-cyclopropyl-2,2-difluoro-2-(4-(thiophen-3-yl)-3-(3-(3-(trifluoromethyl)phenyl) ureido) phenyl)acetamide General Synthetic Method

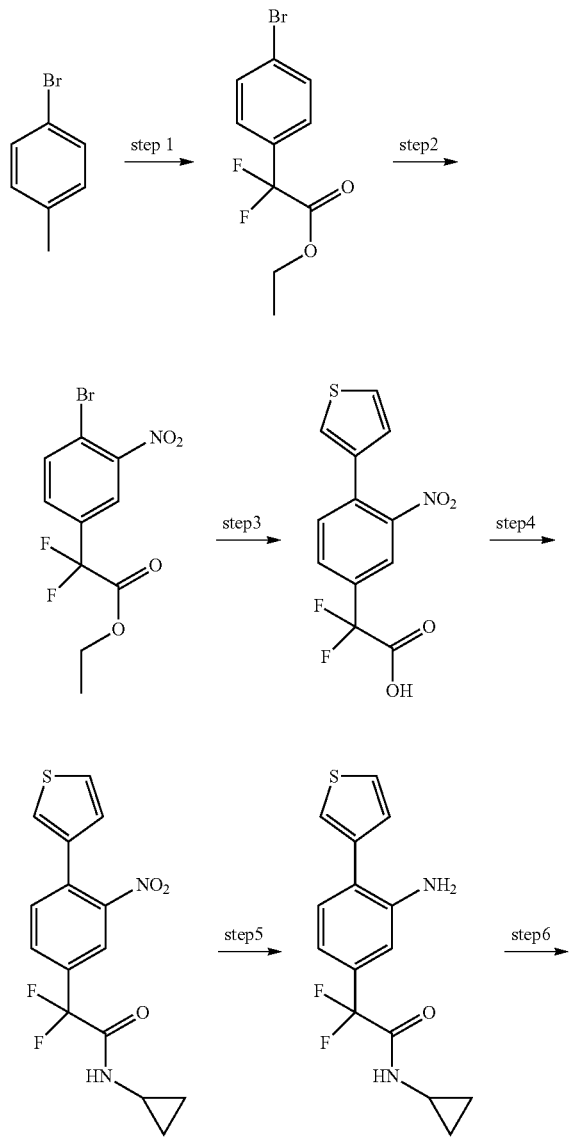

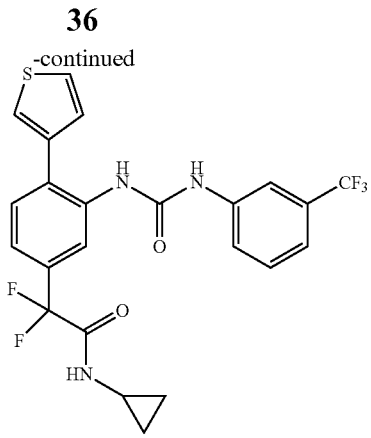

Step 1: Ethyl 2-(4-bromophenyl)-2,2-difluoroacetate

Ethyl bromodifluoroacetate (14.35 g, 70.7 mmol) was added dropwise to a mixed solution of copper powder (8.99 g, 141.5 mmol) and dimethyl sulfoxide (150 mL) under stirring, and was further stirred at room temperature for 1.5 hours after dropwise addition was complete. 4-Bromo-iodobenzene (10.0 g, 35.3 mmol) was added in portions to the mixed solution, and further reacted for 24 hours at room temperature. The reaction solution was poured into a saturated aqueous solution of ammonium chloride, and extracted with ethyl acetate (250 mL×3). The organic phase was combined, washed with a saturated saline solution (250 mL×3), and dried over anhydrous sodium sulphate. Ethyl acetate was removed by rotary evaporation of the organic phase, and the residue was purified by column chromatography on silica gel to afford ethyl 2-(4-bromophenyl)-2,2-difluoroacetate (8.0 g, yield 81.1%). $^1$H-NMR (400 MHz, $CDCl_3$): δ=7.61 (d, J=8.7 Hz, 2H), 7.49 (d, J=8.6 Hz, 2H), 4.25 (m, 2H), 1.22 (m, 3H).

Step 2: Ethyl 2-(4-bromo-3-nitrophenyl)-2,2-difluoroacetate

Fuming nitric acid (4.0 mL) was added dropwise to a solution of ethyl 2-(4-bromophenyl)-2,2-difluoroacetate (4.0 g, 14.3 mmol) in sulphuric acid (50 mL) at a temperature of 0° C., and was further reacted for 1.0 hour at a temperature of 0° C. after dropwise addition was complete. The reaction solution was poured into ice water, and extracted with ethyl acetate (100 mL×3). The organic phase was combined, washed with water (150 mL×3), and dried over anhydrous sodium sulphate. Ethyl acetate was removed by rotary evaporation of the organic phase to afford ethyl 2-(4-bromo-3-nitrophenyl)-2,2-difluoroacetate (3.9 g, yield 84.08%). $^1$H-NMR (400 MHz, DMSO-$d_6$): δ=8.27 (d, J=2.1 Hz, 1H), 8.10 (d, J=8.4 Hz, 1H), 7.81 (dd, J=8.5, 2.0 Hz, 1H), 4.31 (q, J=7.1 Hz, 2H), 1.21 (m, 3H).

Step 3: 2,2-Difluoro-2-(3-nitro-4-(thiophen-3-yl) phenyl)acetic acid

Under the protection of nitrogen gas, to a mixed solution of 1,4-dioxane (160 mL) and water (40 mL) were added ethyl 2-(-4-bromo-3-nitrophenyl)-2,2-difluoroacetate (3.9 g, 12.0 mmol), 3-thienylboric acid (2.3 g, 18.0 mmol), potassium acetate (3.5 g, 35.7 mmol) and tetrakis(triphenylphosphine)palladium (0.7 g, 0.6 mmol). The resulting mixture was reacted for 8 hours at a temperature 80° C., and then cooled to room temperature. The reaction mixture was poured into water, and extracted with ethyl acetate (100 mL×2). After discarding the organic phase, the aqueous phase was adjusted to pH 5 with diluted hydrochloric acid (2M), and extracted with ethyl acetate (100 mL×3). The organic phase was combined, and dried over anhydrous sodium sulphate. Ethyl acetate was removed by rotary evaporation of the organic phase to afford 2,2-difluoro-2-(3-nitro-4-(thiophen-3-yl)phenyl)acetic acid (3.640 g, yield 100%).

Step 4: N-cyclopropyl-2,2-difluoro-2-(3-nitro-4-(thiophen-3-yl)phenyl)acetamide

To a solution of 2,2-difluoro-2-(3-nitro-4-(thiophen-3-yl)phenyl)acetic acid (200.0 mg, 0.67 mmol), 2-(7-azabenzotriazol-1-yl)-N,N,N',N'-tetramethyluronium hexafluorophosphate (382 mg, 1.0 mmol), and diisopropylethylamine (173.2 mg, 1.34 mmol) in N,N-dimethylformamide (25 mL) was added cyclopropylamine (57.0 mg, 1.0 mmol). The resulting mixture was reacted for 3.0 hours at a temperature of 50° C., and then cooled to room temperature. The reaction mixture was poured into water, and extracted with ethyl acetate (100 mL×2). The organic phase was combined, and dried over anhydrous sodium sulphate. Ethyl acetate was removed by rotary evaporation of the organic phase, and the residue was purified by column chromatography on silica gel to afford N-cyclopropyl-2,2-difluoro-2-(3-nitro-4-(thiophen-3-yl)phenyl)acetamide (153 mg, yield 67.7%). $^1$H-NMR (400 MHz, DMSO-d$_6$): δ=9.13 (s, 1H), 8.12 (s, 1H), 7.87 (d, J=8.2 Hz, 1H), 7.83-7.72 (m, 2H), 7.68 (ddd, J=4.9, 2.9, 0.7 Hz, 1H), 7.20-7.12 (m, 1H), 2.73 (d, J=3.7 Hz, 1H), 0.67 (q, J=6.9 Hz, 2H), 0.57 (d, J=2.9 Hz, 2H).

Step 5: 2-(3-amino-4-(thiophen-3-yl)phenyl)-N-cyclopropyl-2,2-difluoroacetamide

To a mixed solution of methanol (40 mL) and water (40 mL) were added N-cyclopropyl-2,2-difluoro-2-(3-nitro-4-(thiophen-3-yl)phenyl)acetamide (153 mg, 0.45 mmol), reduced iron powder (128.4 mg, 2.3 mmol) and ammonium chloride (123.0 mg, 2.3 mmol). The resulting mixture was reacted for 0.5 hour at a temperature of 70° C., and then cooled to room temperature. After filtration, the filter cake was washed with ethyl acetate, and the filtrate was separated. The organic phase was dried over anhydrous sodium sulphate, and the solvent was removed by rotary evaporation to afford 2-(3-amino-4-(thiophen-3-yl)phenyl)-N-cyclopropyl-2,2-difluoroacetamide (140 mg, yield 100%).

Step 6: N-cyclopropyl-2,2-difluoro-2-(4-(thiophen-3-yl)-3-(3-(3-(trifluoromethyl)phenyl) ureido)phenyl)acetamide

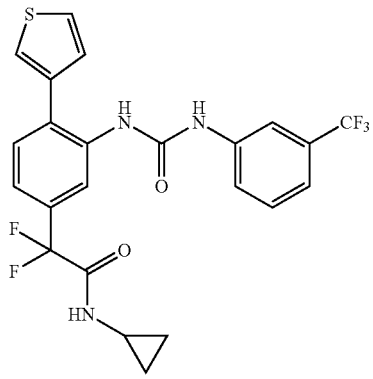

A solution of 2-(3-amino-4-(thiophen-3-yl)phenyl)-N-cyclopropyl-2,2-difluoroacetamide (50.0 mg, 0.16 mmol) and 3-(trifluoromethyl)phenyl isocyanate (35.5 mg, 0.19 mmol) in dichloromethane (50 mL) was stirred at room temperature for 12 hours. The reaction mixture was separated directly by column chromatography on silica gel to afford N-cyclopropyl-2,2-difluoro-2-(4-(thiophen-3-yl)-3-(3-(3-(trifluoromethyl)phenyl)ureido)phenyl) acetamide (68.3 mg, yield 85.01%). $^1$H-NMR (400 MHz, DMSO-d$_6$): δ=9.52 (s, 1H), 9.01 (d, J=4.3 Hz, 1H), 8.19 (s, 1H), 8.00 (d, J=8.0 Hz, 2H), 7.73 (m, 2H), 7.46 (m, 3H), 7.28 (m, 3H), 2.72 (m, 1H), 0.64 (m, 2H), 0.57 (m, 2H).

Example 2: 2,2-Difluoro-2-(4-(thiophen-3-yl)-3-(3-(3-trifluoromethyl)phenyl)ureido)phenyl)-N-(2,2,2-trifluoroethyl)acetamide

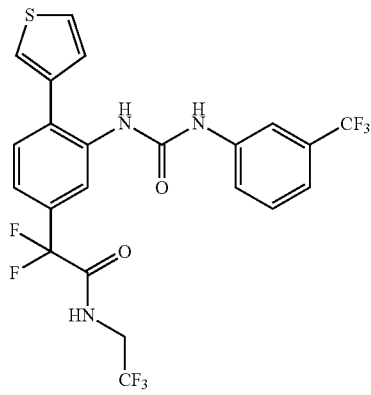

2,2-Difluoro-2-(4-(thiophen-3-yl)-3-(3-(3-(trifluoromethyl)phenyl)ureido)phenyl)-N-(2,2,2-trifluoroethyl)acetamide was prepared referring to the synthetic method in Example 1. $^1$H-NMR (400 MHz, DMSO-d$_6$): δ=9.70 (s, 1H), 9.50 (s, 1H), 8.20 (d, J=1.7 Hz, 1H), 7.97 (d, J=6.4 Hz, 2H), 7.71 (m, 2H), 7.48-7.39 (m, 3H), 7.31-7.20 (m, 3H), 3.93 (m, 2H).

Example 3: 2,2-Difluoro-N-isopropyl-2-(4-(thiophen-3-yl)-3-(3-(3-trifluoromethyl)phenyl) ureido) phenyl)acetamide

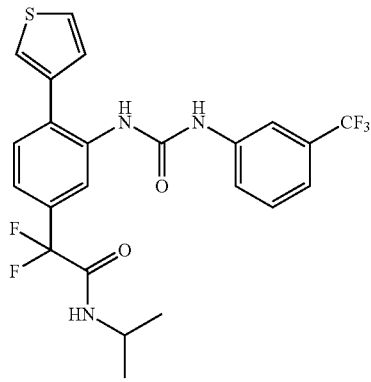

2,2-Difluoro-N-isopropyl-2-(4-(thiophen-3-yl)-3-(3-(3-trifluoromethyl)phenyl)ureido)phenyl) acetamide was prepared referring to the synthetic method in Example 1. ¹H-NMR (400 MHz, DMSO-d₆): δ=9.58 (s, 1H), 8.84 (d, J=1.9 Hz, 1H), 8.21 (s, 1H), 8.02 (d, J=5.7 Hz, 2H), 7.88-7.69 (m, 2H), 7.47 (m, 3H), 7.30 (m, 3H), 3.93 (dd, J=13.7, 6.4 Hz, 1H), 1.11 (d, J=6.6 Hz, 6H).

Example 4: N-(1-cyanocyclopropyl)-2,2-difluoro-2-(4-(thiophen-3-yl)-3-(3-(3-(trifluoromethyl) phenyl) ureido)phenyl)acetamide

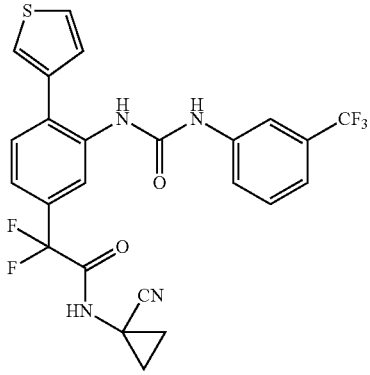 [SMILES: N#CC1(NC(=O)C(F)(F)c2ccc(-c3ccsc3)c(NC(=O)Nc3cccc(C(F)(F)F)c3)c2)CC1]

N-(1-cyanocyclopropyl)-2,2-difluoro-2-(4-(thiophen-3-yl)-3-(3-(trifluoromethyl)phenyl)ureido)phenyl)acetamide was prepared referring to the synthetic method in Example 1. ¹H-NMR (400 MHz, DMSO-d₆): δ=9.93 (s, 1H), 9.44 (s, 1H), 8.11 (d, J=1.6 Hz, 1H), 7.90 (s, 2H), 7.65 (m, 2H), 7.42-7.31 (m, 3H), 7.25-7.12 (m, 3H), 1.45 (dd, J=8.4, 5.6 Hz, 2H), 1.16 (dd, J=8.4, 5.7 Hz, 2H).

Example 5: 2,2-Difluoro-N-(oxetan-3-yl)-2-(4-(thiophen-3-yl)-3-(3-(3-(trifluoromethyl)phenyl) ureido) phenyl)acetamide

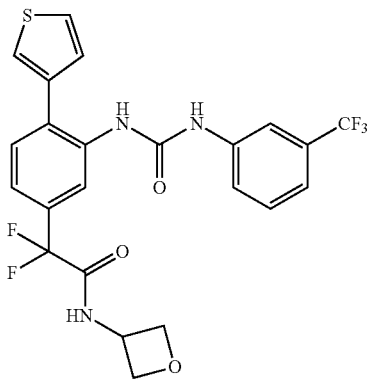 [SMILES: O=C(Nc1cccc(C(F)(F)F)c1)Nc1cc(C(F)(F)C(=O)NC2COC2)ccc1-c1ccsc1]

2,2-Difluoro-N-(oxygen-3-yl)-2-(4-(thiophen-3-yl)-3-(3-(3-(trifluoromethyl)phenyl)ureido)phenyl) acetamide was prepared referring to the synthetic method in Example 1. ¹H-NMR (400 MHz, DMSO-d₆): δ=9.73 (d, J=6.4 Hz, 1H), 9.52 (s, 1H), 8.24 (d, =1.6 Hz, 1H), 8.00 (d, =2.8 Hz, 2H), 7.75 (m, 2H), 7.46 (dd, J=16.6, 6.6 Hz, 3H), 7.34-7.26 (m, 3H), 4.84 (dt, J=13.9, 7.0 Hz, 1H), 4.69 (t, J=6.9 Hz, 2H), 4.56 (t, J=6.5 Hz, 2H).

Example 6: N-(azetidin-3-yl)-2,2-difluoro-2-(4-(thiophen-3-yl)-3-(3-(3-(trifluoromethyl)phenyl) ureido)phenyl)acetamide

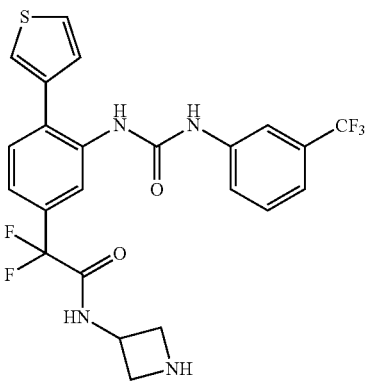 [SMILES: O=C(Nc1cccc(C(F)(F)F)c1)Nc1cc(C(F)(F)C(=O)NC2CNC2)ccc1-c1ccsc1]

N-(azetidin-3-yl)-2,2-difluoro-2-(4-(thiophen-3-yl)-3-(3-(3-(trifluoromethyl)phenyl)ureido) phenyl)acetamide was prepared referring to the synthetic method in Example 1. ¹H-NMR (400 MHz, DMSO-d₆): δ=9.73 (d, J=7.1 Hz, 1H), 9.55 (s, 1H), 8.24 (dd, J=8.0, 1.7 Hz, 1H), 8.08-7.92 (m, 2H), 7.82-7.71 (m, 2H), 7.49 (m, 3H), 7.35-7.17 (m, 3H), 4.73-4.55 (m, 1H), 3.88 (m, 2H), 3.63 (m, 2H).

Example 7: 2,2-Difluoro-N-(1-methylazetidin-3-yl)-2-(4-(thiophen-3-yl)-3-(3-(3-(trifluoromethyl)phenyl)ureido)phenyl)acetamide

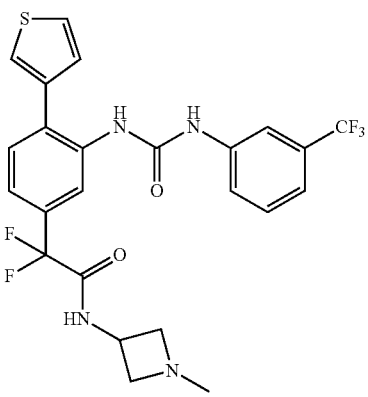 [SMILES: CN1CC(NC(=O)C(F)(F)c2ccc(-c3ccsc3)c(NC(=O)Nc3cccc(C(F)(F)F)c3)c2)C1]

2,2-Difluoro-N-(1-methylazetidin-3-yl)-2-(4-(thiophen-3-yl)-3-(3-(3-(trifluoromethyl)phenyl)ureido) phenyl)acetamide was prepared referring to the synthetic method in Example 1. ¹H-NMR (400 MHz, DMSO-d₆): δ=9.52 (s, 1H), 9.39 (d, J=6.9 Hz, 1H), 8.22 (d, J=1.7 Hz, 1H), 8.02 (s, 1H), 7.98 (s, 1H), 7.73 (m, 2H), 7.56-7.39 (m, 3H), 7.37-7.24 (m, 3H), 4.23 (m, 1H), 3.54-3.44 (m, 2H), 2.99 (t, J=7.4 Hz, 2H), 2.21 (s, 3H).

Example 8: 2,2-Difluoro-N-(2-hydroxy-2-methyl-propyl)-2-(4-(thiophen-3-yl)-3-(3-(3-(trifluoromethyl) phenyl)ureido)phenyl)acetamide

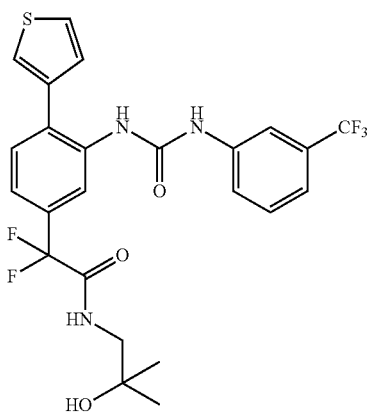 [SMILES: CC(C)(O)CNC(=O)C(F)(F)c1ccc(-c2ccsc2)c(NC(=O)Nc2cccc(C(F)(F)F)c2)c1]

2,2-Difluoro-N-(2-hydroxy-2-methylpropyl)-2-(4-(thiophen-3-yl)-3-(3-(3-(trifluoromethyl)phenyl)ureido) phenyl)acetamide was prepared referring to the synthetic method in Example 1. $^1$H-NMR (400 MHz, DMSO-d$_6$): δ=9.51 (s, 1H), 8.72 (t, J=6.1 Hz, 1H), 8.22 (s, 1H), 8.00 (d, J=8.5 Hz, 2H), 7.78-7.62 (m, 2H), 7.45 (m, 3H), 7.29 (m, 3H), 4.54 (s, 1H), 3.09 (d, J=6.1 Hz, 2H), 1.02 (s, 6H).

Example 9: N-cyclopropyl-2,2-difluoro-2-(4-(thiophen-3-yl)-3-(3-(2-(trifluoromethyl)pyridine-4-yl) ureido)phenyl)acetamide

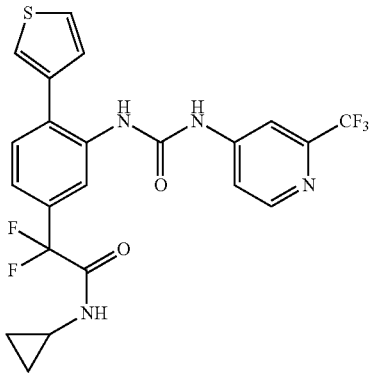 [SMILES: O=C(Nc1ccnc(C(F)(F)F)c1)Nc1cc(C(F)(F)C(=O)NC2CC2)ccc1-c1ccsc1]

N-cyclopropyl-2,2-difluoro-2-(4-(thiophen-3-yl)-3-(3-(2-(trifluoromethyl)pyridin-4-yl)ureido) phenyl)acetamide was prepared referring to the synthetic method in Example 1. $^1$H-NMR (400 MHz, DMSO-d$_6$): δ=9.87 (s, 1H), 8.97 (s, 1H), 8.37 (d, J=54.4 Hz, 1H), 8.17 (s, 1H), 8.05 (s, 1H), 7.95 (d, J=11.1 Hz, 1H), 7.67 (m, 2H), 7.39 (m, 2H), 7.23 (m, 2H), 2.65 (m, 1H), 0.54 (m, 4H).

Example 10: N-cyclopropyl-2,2-difluoro-2-(3-(3-(4-fluoro-3-(trifluoromethyl)phenyl) ureido)-4-(thiophen-3-yl)phenyl)acetamide

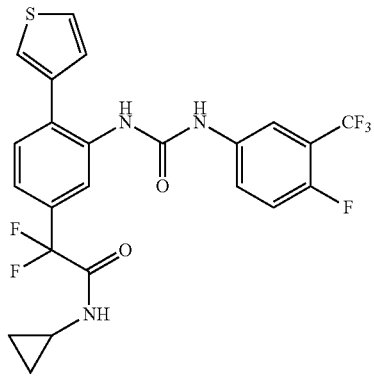 [SMILES: O=C(Nc1ccc(F)c(C(F)(F)F)c1)Nc1cc(C(F)(F)C(=O)NC2CC2)ccc1-c1ccsc1]

N-cyclopropyl-2,2-difluoro-2-(3-(3-(4-fluoro-3-(trifluoromethyl)phenyl)ureido)-4-(thiophen-3-yl) phenyl)acetamide was prepared referring to the synthetic method in Example 1. $^1$H-NMR (400 MHz, DMSO-d$_6$): δ=9.47 (s, 1H), 9.18 (s, 1H), 8.99 (d, J=4.3 Hz, 1H), 8.12 (d, J=5.5 Hz, 1H), 7.93 (m, 3H), 7.74-7.64 (m, 1H), 7.56-7.42 (m, 1H), 7.38 (m, 3H), 2.67 (m, 1H), 0.62 (m, 2H), 0.53 (m, 2H).

Example 11: N-cyclopropyl-2,2-difluoro-2-(3-(3-(3-(trifluoromethyl)phenyl)ureido)-4-(6-(trifluoromethyl)pyridin-2-yl)phenyl)acetamide

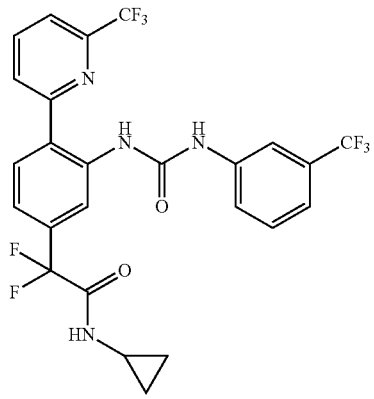 [SMILES: O=C(Nc1cccc(C(F)(F)F)c1)Nc1cc(C(F)(F)C(=O)NC2CC2)ccc1-c1cccc(C(F)(F)F)n1]

N-cyclopropyl-2,2-difluoro-2-(3-(3-(3-(trifluoromethyl) phenyl)ureido)-4-(6-(trifluoromethyl) pyridin-2-yl)phenyl) acetamide was prepared referring to the synthetic method in Example 1. $^1$H-NMR (400 MHz, CDCl$_3$): δ=12.03 (s, 1H), 8.70 (s, 1H), 8.10 (dt, J=15.7, 8.0 Hz, 2H), 7.87 (d, J=8.4 Hz, 1H), 7.81 (s, 1H), 7.75 (d, J=6.7 Hz, 1H), 7.57 (d, J=8.1 Hz, 1H), 7.50 (d, J=8.5 Hz, 1H), 7.44 (t, J=7.8 Hz, 1H), 7.33 (d, J=7.3 Hz, 1H), 6.64 (s, 1H), 6.47 (s, 1H), 2.80 (m, 1H), 0.94-0.81 (m, 2H), 0.66 (m, 2H).

Example 12: N-cyclopropyl-2,2-difluoro-2-(2-(3-(3-(trifluoromethyl)phenyl)ureido)-[1,1'-biphenyl]-4-yl)acetamide

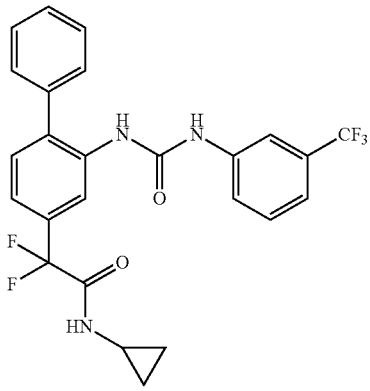 [SMILES: O=C(Nc1cccc(C(F)(F)F)c1)Nc1cc(C(F)(F)C(=O)NC2CC2)ccc1-c1ccccc1]

N-cyclopropyl-2,2-difluoro-2-(2-(3-(3-(trifluoromethyl)phenyl)ureido)-[1,1'-biphenyl]-4-yl) acetamide was prepared referring to the synthetic method in Example 1. $^1$H-NMR (400 MHz, DMSO-d$_6$): δ=9.42 (s, 1H), 9.01 (d, J=4.3 Hz, 1H), 8.19 (s, 1H), 8.00 (m, 3H), 7.73 (m, 3H), 7.46 (m, 3H), 7.28 (m, 3H), 2.72 (m, 1H), 0.58 (m, 2H), 0.50 (m, 2H).

Example 13: N-cyclopropyl-2-(4-(1,3-dimethyl-1H-pyrazol-5-yl)-3-(3-(3-(trifluoromethyl) phenyl)ureido)phenyl)-2,2-difluoroacetamide

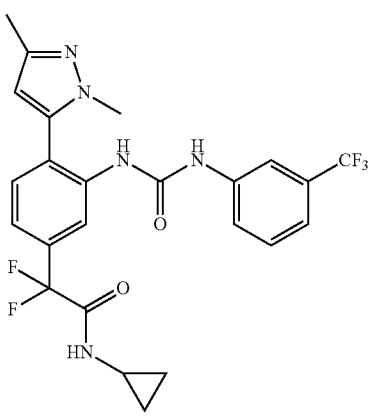 [SMILES: Cc1cc(-c2ccc(C(F)(F)C(=O)NC3CC3)cc2NC(=O)Nc2cccc(C(F)(F)F)c2)n(C)n1]

N-cyclopropyl-2-(4-(1,3-dimethyl-1H-pyrazol-5-yl)-3-(3-(3-(trifluoromethyl)phenyl)ureido) phenyl)-2,2-difluoroacetamide was prepared referring to the synthetic method in Example 1. $^1$H-NMR (400 MHz, DMSO-d$_6$): δ=9.57 (s, 1H), 8.09 (s, 1H), 7.98 (d, J=8.0 Hz, 2H), 7.73 (m, 2H), 7.46 (m, 3H), 7.28 (m, 2H), 3.80 (s, 3H), 2.72 (m, 4H), 0.59 (m, 2H), 0.47 (m, 2H).

Example 14: N-cyclopropyl-2-(4-(thiophen-3-yl)-3-(3-(3-(trifluoromethyl)phenyl)ureido)phenyl) propanamide General Synthetic Method

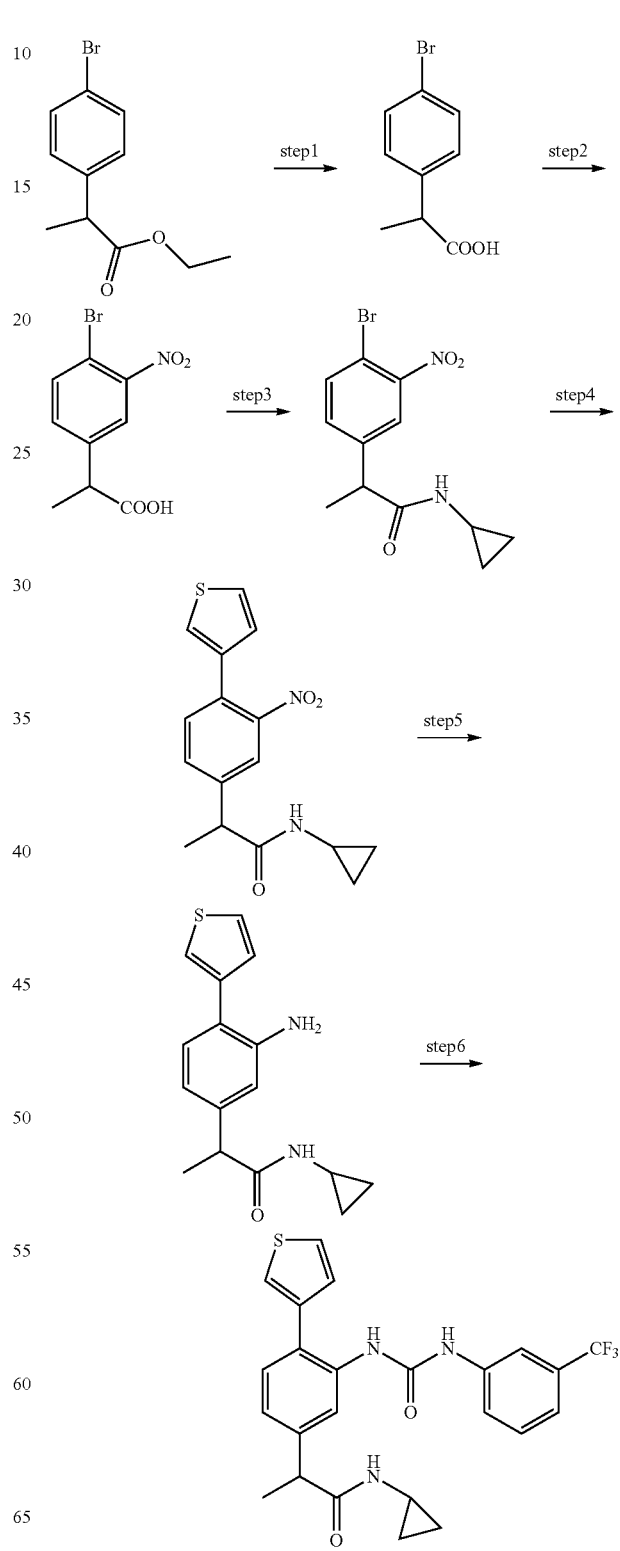

Step 1: 2-(4-bromophenyl)propanoic acid

To a mixed solution of ethyl 2-(4-bromophenyl)propanoate (3.0 g, 11.7 mmol) in tetrahydrofuran (50 mL), methanol (50 mL) and water (50 mL) was added solid lithium hydroxide monohydrate (0.56 g, 23.4 mmol). The reaction mixture was stirred at room temperature for 4 hours, and adjusted to pH 5 with 2 mol/L diluted hydrochloric acid. The organic solvent was removed by rotary evaporation. The resulting solid was filtered, washed with water, and dried to afford 2-(4-bromophenyl)propanoic acid (2.0 g, yield 74.8%).

Step 2: 2-(4-bromo-3-nitrophenyl)propanoic acid 2-(4-bromophenyl)propanoic acid (2.0 g, 8.73 mmol) was dissolved in concentrated sulphuric acid (50 mL), and cooled to a temperature of 0° C. Fuming nitric acid (2.0 mL) was slowly added dropwise to the reactant. The reaction mixture was stirred for 1 hour at a temperature of 0° C., and slowly added to ice water. The precipitated solid was filtered, and dried to afford 2-(4-bromo-3-nitrophenyl)propanoic acid (2.0 g, yield 83.6%).

Step 3: 2-(4-bromo-3-nitrophenyl)-N-cyclopropylpropanamide

To a solution of 2-(4-bromo-3-nitrophenyl)propanoic acid (1.0 g, 3.65 mmol), 2-(7-azabenzotriazol-1-yl)-N,N,N',N'-tetramethyluronium hexafluorophosphate (2.8 g, 7.3 mmol) and diisopropylethylamine (1.88 g, 14.6 mmol) in N,N-dimethylformamide (50 mL) was added cyclopropylamine (0.25 g, 4.38 mmol). The reaction mixture was reacted for 3.0 hours at a temperature of 50° C., and then cooled to room temperature. The reaction mixture was poured into water, and extracted with ethyl acetate (100 mL×2). The organic phase was combined, and dried over anhydrous sodium sulphate. Ethyl acetate was removed by rotary evaporation of the organic phase, and the residue was purified by column chromatography on silica gel to afford 2-(4-bromo-3-nitrophenyl)-N-cyclopropyl propanamide (0.6 g, yield 52.5%).

Step 4: N-cyclopropyl-2-(3-nitro-4-(thiophen-3-yl)phenyl)propanamide

Under the protection of nitrogen gas, 2-(4-bromo-3-nitrophenyl)-N-cyclopropyl propanamide (0.6 g, 1.92 mmol), 3-thienylboric acid (0.37 g, 2.88 mmol), sodium carbonate (0.61 g, 5.76 mmol) and tetrakis(triphenylphosphine)palladium (0.11 g, 0.1 mmol) were added to a mixed solution of 1,4-dioxane (100 mL) and water (25 mL). The reaction mixture was reacted for 8 hours at a temperature of 90° C., and then cooled to room temperature. The reaction mixture was poured into water, and extracted with ethyl acetate (100 mL×3). The organic phase was combined, and dried over anhydrous sodium sulphate. Ethyl acetate was removed by rotary evaporation of the organic phase, and the residue was purified by column chromatography on silica gel to afford N-cyclopropyl-2-(3-nitro-4-(thiophen-3-yl)phenyl)propanamide (0.5 g, yield 82.5%).

Step 5: 2-(3-amino-4-(thiophen-3-yl)phenyl)-N-cyclopropylpropanamide

N-cyclopropyl-2-(3-nitro-4-(thiophen-3-yl)phenyl)propanamide (0.5 g, 1.58 mmol), reduced iron powder (433.0 mg, 7.9 mmol) and ammonium chloride (440.0 mg, 7.9 mmol) were added to a mixed solution of methanol (40 mL) and water (40 mL). The reaction mixture was reacted for 0.5 hour at a temperature of 70° C., and then cooled to room temperature. After filtration, the solid was washed with ethyl acetate, and the filtrate was separated. The organic phase was dried over anhydrous sodium sulphate, and the solvent was removed by rotary evaporation of the organic phase to afford 2-(3-amino-4-(thiophen-3-yl)phenyl)-N-cyclopropylpropanamide (325.0 mg, yield 71.8%).

Step 6: N-cyclopropyl-2-(4-(thiophen-3-yl)-3-(3-(3-(trifluoromethyl)phenyl)ureido)phenyl) propanamide

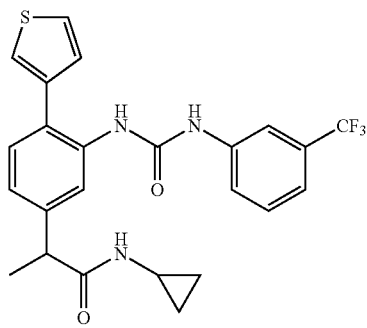 [SMILES: CC(C(=O)NC1CC1)c1ccc(-c2ccsc2)c(NC(=O)Nc2cccc(C(F)(F)F)c2)c1]

A solution of 2-(3-amino-4-(thiophen-3-yl)phenyl)-N-cyclopropylpropanamide (80.0 mg, 0.28 mmol) and 3-(trifluoromethyl)phenyl isocyanate (78.0 mg, 0.42 mmol) in dichloromethane (50 mL) was stirred at room temperature for 12 hours. The reaction mixture was purified directly by column chromatography on silica gel to afford N-cyclopropyl-2-(4-(thiophen-3-yl)-3-(3-(3-(trifluoromethyl)phenyl)ureido)phenyl)propanamide (60.0 mg, yield 45.3%). $^1$H-NMR (400 MHz, DMSO-d$_6$): δ=9.35 (s, 1H), 8.03 (d, J=4.3 Hz, 1H), 7.97 (s, 1H), 7.82-7.72 (m, 2H), 7.63 (dd, J=4.9, 2.9 Hz, 1H), 7.60-7.55 (m, 1H), 7.47-7.39 (m, 2H), 7.28-7.15 (m, 3H), 7.03 (dd, J=8.0, 1.8 Hz, 1H), 3.51-3.41 (m, 1H), 2.55 (qd, J=7.9, 4.0 Hz, 1H), 1.27 (d, J=7.0 Hz, 3H), 0.60-0.44 (m, 2H), 0.40-0.24 (m, 2H).

Example 15: N-cyclopropyl-2-methyl-2-(4-(thiophen-3-yl)-3-(3-(3-(trifluoromethyl)phenyl) ureido)phenyl)propanamide

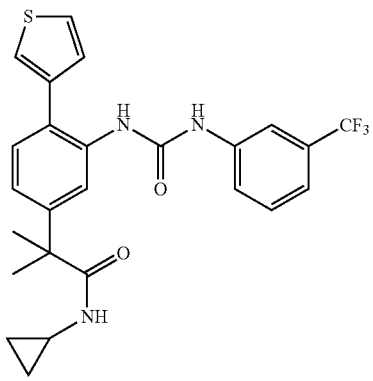 [SMILES: CC(C)(C(=O)NC1CC1)c1ccc(-c2ccsc2)c(NC(=O)Nc2cccc(C(F)(F)F)c2)c1]

N-cyclopropyl-2-methyl-2-(4-(thiophen-3-yl)-3-(3-(3-trifluoromethyl)phenyl)ureido)phenyl) propanamide was prepared referring to the synthetic method in Example 14.

¹H-NMR (400 MHz, DMSO-d₆): δ=9.34 (s, 1H), 7.95 (s, 1H), 7.84-7.71 (m, 2H), 7.64 (dd, J=4.9, 2.9 Hz, 1H), 7.58 (d, J=1.7 Hz, 1H), 7.49-7.38 (m, 2H), 7.35 (d, J=3.8 Hz, 1H), 7.22 (m, 3H), 6.99 (dd, J=8.1, 1.8 Hz, 1H), 2.56 (m, 1H), 1.45 (s, 6H), 0.58-0.45 (m, 2H), 0.43-0.35 (m, 2H).

Example 16: N-cyclopropyl-2-(4-(thiophen-3-yl)-3-(3-(3-trifluoromethyl)phenyl)ureido) phenyl)acetamide

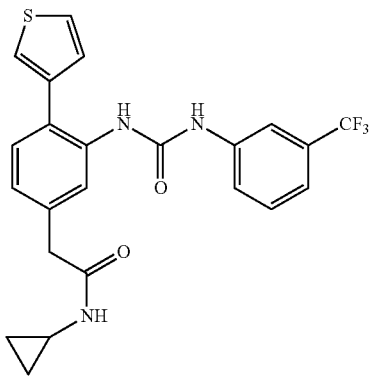 [SMILES: O=C(Cc1ccc(-c2ccsc2)c(NC(=O)Nc2cccc(C(F)(F)F)c2)c1)NC1CC1]

N-cyclopropyl-2-(4-(thiophen-3-yl)-3-(3-(3-trifluoromethyl)phenyl)ureido)phenyl)acetamide was prepared referring to the synthetic method in Example 14. ¹H-NMR (400 MHz, DMSO-d₆): δ=9.03 (s, 1H), 7.78 (d, J=4.1 Hz, 1H), 7.65 (s, 1H), 7.45 (s, 1H), 7.39 (d, J=1.5 Hz, 1H), 7.31 (dd, J=4.9, 2.9 Hz, 1H), 7.27-7.22 (m, 1H), 7.12-7.05 (m, 2H), 6.97-6.81 (m, 3H), 6.62 (dd, J=7.9, 1.7 Hz, 1H), 3.17 (s, 2H), 2.83-2.73 (m, 1H), 0.59 (m, 2H), 0.38 (m, 2H).

Example 17: N-cyclopropyl-1-(4-(thiophen-3-yl)-3-(3-(3-(trifluoromethyl)phenyl)ureido)phenyl) cyclopropanecarboxamide

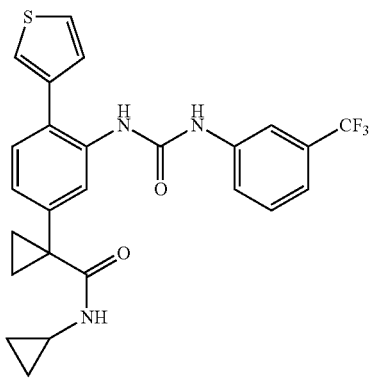 [SMILES: O=C(Nc1cccc(C(F)(F)F)c1)Nc1cc(C2(C(=O)NC3CC3)CC2)ccc1-c1ccsc1]

N-cyclopropyl-1-(4-(thiophen-3-yl)-3-(3-(3-(trifluoromethyl)phenyl)ureido)phenyl) cyclopropanecarboxamide was prepared referring to the synthetic method in Example 14. ¹H-NMR (400 MHz, DMSO-d₆): δ=9.39 (s, 1H), 8.00 (s, 1H), 7.89 (s, 1H), 7.85 (d, J=1.6 Hz, 1H), 7.71 (dd, J=5.0, 2.9 Hz, 1H), 7.67-7.64 (m, 1H), 7.50 (q=8.3 Hz, 2H), 7.28 (m, 3H), 7.06 (dd, J=7.9, 1.7 Hz, 1H), 6.97 (d, J=3.8 Hz, 1H), 2.60 (m, 1H), 1.33 (m, 2H), 0.97 (m, 2H), 0.55 (m, 2H), 0.42 (m, 2H).

Example 18: N-cyclopropyl-2-methyl-2-(3-(3-(3-oxoisoindol-5-yl)ureido)-4-(thiophen-3-yl)phenyl)propanamide

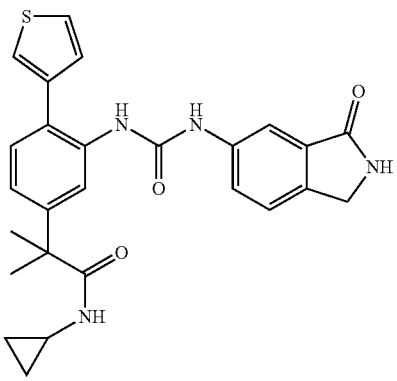 [SMILES: CC(C)(C(=O)NC1CC1)c1ccc(-c2ccsc2)c(NC(=O)Nc2ccc3c(c2)C(=O)NC3)c1]

N-cyclopropyl-2-methyl-2-(3-(3-(3-oxoisoindol-5-yl) ureido)-4-(thiophen-3-yl)phenyl)propanamide was prepared referring to the synthetic method in Example 14. ¹H-NMR (400 MHz, DMSO-d₆): δ=9.47 (s, 1H), 8.46 (s, 1H), 7.93 (s, 1H), 7.84 (d, J=1.7 Hz, 1H), 7.75 (d, J=1.8 Hz, 1H), 7.63 (dd, J=4.7, 2.5 Hz, 2H), 7.40 (m, 3H), 7.28-7.17 (m, 2H), 6.98 (dd, J=8.1, 2.0 Hz, 1H), 4.24 (s, 2H), 2.59-2.49 (m, 1H), 1.38 (s, 6H), 0.54-0.44 (m, 2H), 0.41-0.33 (m, 2H).

Example 19: N-cyclopropyl-1-(4-(thiophen-3-yl)-3-(3-(3-(trifluoromethyl)phenyl)ureido)phenyl) cyclobutanecarboxamide

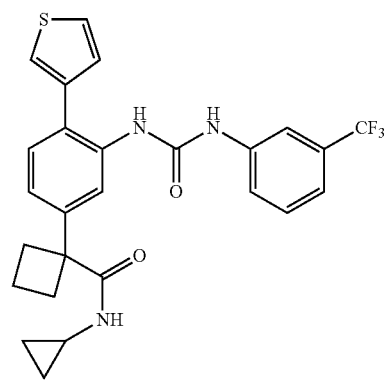 [SMILES: O=C(Nc1cccc(C(F)(F)F)c1)Nc1cc(C2(C(=O)NC3CC3)CCC2)ccc1-c1ccsc1]

N-cyclopropyl-1-(4-(thiophen-3-yl)-3-(3-(3-(trifluoromethyl)phenyl)ureido)phenyl) cyclobutanecarboxamide was prepared referring to the synthetic method in Example 14. ¹H-NMR (400 MHz, DMSO-d₆): δ=9.39 (s, 1H), 8.00 (s, 1H), 7.88-7.76 (m, 2H), 7.68 (dd, J=4.9, 2.9 Hz, 1H), 7.63-7.57 (m, 2H), 7.53-7.40 (m, 2H), 7.26 (dd, J=9.2, 4.5 Hz, 3H), 7.09 (dd, J=8.0, 1.8 Hz, 1H), 2.76-2.61 (m, 2H), 2.58 (m, 1H), 2.39-2.23 (m, 2H), 1.81-1.68 (m, 2H), 0.60-0.47 (m, 2H), 0.47-0.35 (m, 2H).

Example 20: N-cyclopropyl-2-(4-(thiophen-3-yl)-3-(3-(3-(trifluoromethyl)phenyl)ureido)phenyl) butanamide

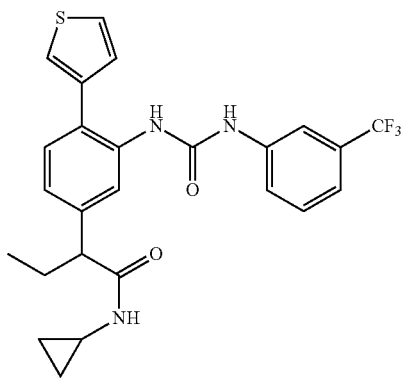 [SMILES: CCC(C(=O)NC1CC1)c1ccc(-c2ccsc2)c(NC(=O)Nc2cccc(C(F)(F)F)c2)c1]

N-cyclopropyl-2-(4-(thiophen-3-yl)-3-(3-(3-(trifluoromethyl)phenyl)ureido)phenyl) butanamide was prepared referring to the synthetic method in Example 14. $^1$H-NMR (400 MHz, DMSO-d$_6$): δ=9.41 (s, 1H), 8.12 (d, J=4.2 Hz, 1H), 8.03 (s, 1H), 7.82 (s, 2H), 7.68 (m, 1H), 7.63 (m, 1H), 7.48 (m, 2H), 7.26 (m, 3H), 7.08 (d, J=8.0 Hz, 1H), 3.23 (m, 1H), 2.59 (m, 1H), 1.61-1.94 (m, 2H), 0.82 (t, J=7.3 Hz, 3H), 0.57 (m, 2H), 0.34 (m, 2H).

Example 21: 2-Amino-N-cyclopropyl-2-(4-(thiophen-3-yl)-3-(3-(3-(trifluoromethyl)phenyl) ureido)phenyl)acetamide

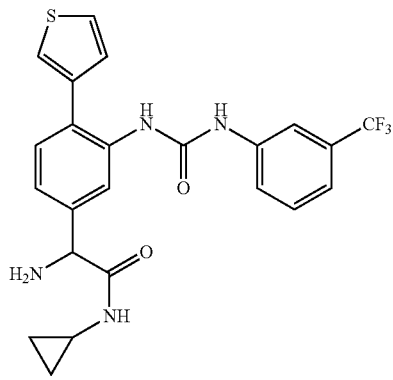

2-Amino-N-cyclopropyl-2-(4-(thiophen-3-yl)-3-(3-(3-(trifluoromethyl)phenyl)ureido)phenyl) acetamide was prepared referring to the synthetic method in Example 14. $^1$H-NMR (400 MHz, DMSO-d$_6$): δ=9.74 (s, 1H), 8.70 (m, 2H), 8.12-8.04 (m, 3H), 7.78-7.39 (m, 3H), 7.28 (m, 3H), 4.79 (d, J=5.1 Hz, 1H), 3.69 (s, 1H), 2.69 (dd, J=7.5, 3.5 Hz, 1H), 0.63 (m, 2H), 0.45 (m, 2H).

Example 22: N-cyclopropyl-4-(4-(thiophen-3-yl)-3-(3-(3-(trifluoromethyl)phenyl)ureido)phenyl) piperidine-4-carboxamide

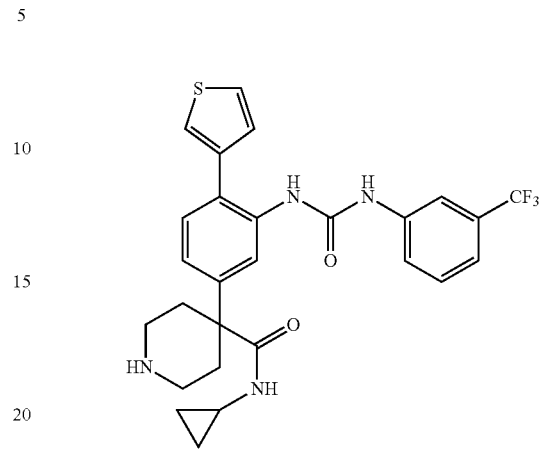

N-cyclopropyl-4-(4-(thiophen-3-yl)-3-(3-(3-(trifluoromethyl)phenyl)ureido)phenyl)piperidine-4-carboxamide was prepared referring to the synthetic method in Example 14. $^1$H-NMR (400 MHz, DMSO-d$_6$): δ=9.57 (d, J=14.3 Hz, 1H), 8.61 (s, 2H), 8.04 (d, J=8.1 Hz, 2H), 7.98 (s, 1H), 7.89 (s, 1H), 7.81 (m, 1H), 7.68 (m, 1H), 7.48 (m, 2H), 7.35-7.23 (m, 2H), 7.04 (t, J=5.9 Hz, 1H), 3.26 (m, 3H), 2.87 (m, 2H), 2.65 (m, 1H), 2.53 (m, 2H), 2.00 (m, 2H), 0.57 (m, 2H), 0.42 (m, 2H).

Example 23: N-cyclopropyl-4-(thiophen-3-yl)-3-(3-(3-(trifluoromethyl)phenyl)ureido)benzamide

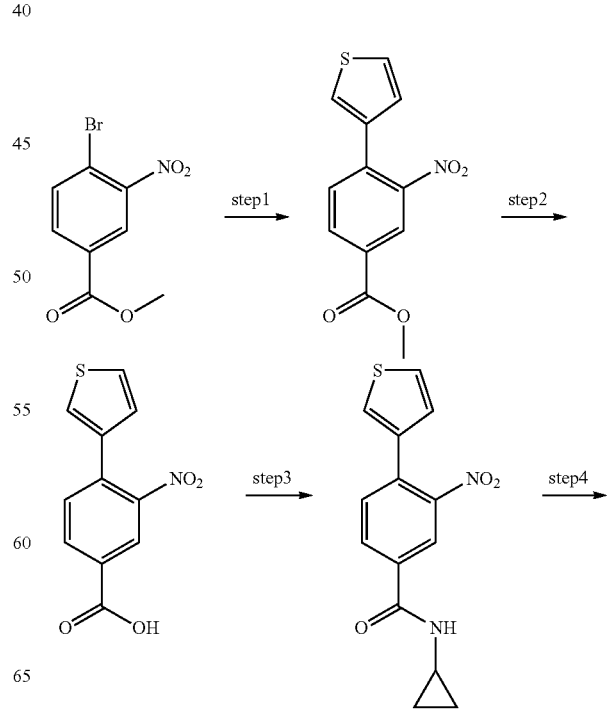

-continued

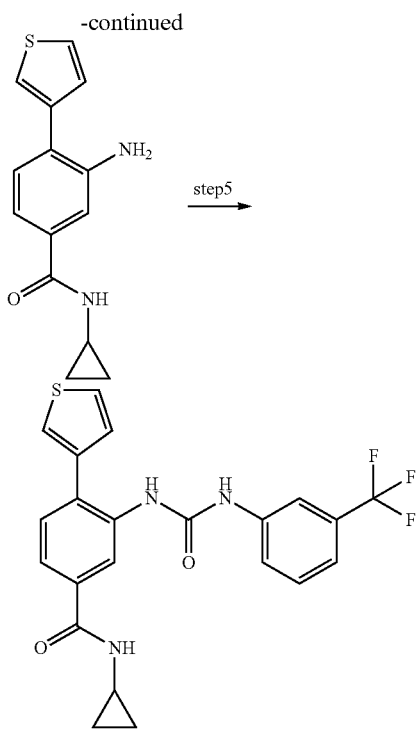

Step 1: methyl 3-nitro-4-(thiophen-3-yl)benzoate

Under the protection of nitrogen gas, methyl 4-bromo-3-nitrobenzoate (1.30 g, 5.0 mmol), 3-thienylboric acid (0.77 g, 6.0 mmol), sodium carbonate (1.06 g, 10.0 mmol) and tetrakis(triphenylphosphine)palladium (0.29 g, 0.25 mmol) were added to a mixed solution of 1,4-dioxane (160 mL) and water (40 mL). The reaction mixture was reacted for 8 hours at a temperature of 90° C., and then cooled to room temperature. The reaction mixture was poured into water, and extracted with ethyl acetate (100 mL×3). The organic phase was combined, and dried over anhydrous sodium sulphate. Ethyl acetate was removed by rotary evaporation of the organic phase, and the residue was purified by column chromatography on silica gel to afford methyl 3-nitro-4-(thiophen-3-yl)benzoate (1.12 g, yield 85.1%). $^1$H-NMR (400 MHz, DMSO-$d_6$): δ=8.39 (d, J=1.7 Hz, 1H), 8.22 (dd, J=8.1, 1.8 Hz, 1H), 7.83-7.76 (m, 2H), 7.69 (dd, J=5.0, 2.9 Hz, 1H), 7.16 (dd, J=5.0, 1.4 Hz, 1H), 3.91 (s, 3H).

Step 2: 3-nitro-4-(thiophen-3-yl)benzoic acid

To a mixed solution of methyl 3-nitro-4-(thiophen-3-yl)benzoate (496.0 mg, 1.88 mmol) in tetrahydrofuran (20 mL), methanol (20 mL) and water (20 mL) was added solid lithium hydroxide monohydrate (157.8 mg, 3.76 mmol). The reaction mixture was stirred at room temperature for 4 hours, and adjusted to pH 5 with 2 M diluted hydrochloric acid. The organic solvent was removed by rotary evaporation. The resulting solid was filtered, washed with water, and dried to afford 3-nitro-4-(thiophen-3-yl)benzoic acid (416.0 mg, yield 88.6%).

Step 3: N-cyclopropyl-3-nitro-4-(thiophen-3-yl)benzamide

To a solution of 3-nitro-4-(thiophen-3-yl)benzoic acid (416.0 mg, 1.67 mmol), 2-(7-azabenzotriazol-1-yl)-N,N,N',N'-tetramethyluronium hexafluorophosphate (1.27 g, 3.34 mmol) and diisopropylethylamine (0.86 g, 6.68 mmol) in N,N-dimethylformamide (25 mL) was added cyclopropylamine (190.7 mg, 3.34 mmol). The reaction mixture was reacted for 3 hours at a temperature of 50° C., and then cooled to room temperature. The reaction mixture was poured into water, and extracted with ethyl acetate (100 mL×2). The organic phase was combined, and dried over anhydrous sodium sulphate. Ethyl acetate was removed by rotary evaporation of the organic phase, and the residue was purified by column chromatography on silica gel to afford N-cyclopropyl-3-nitro-4-(thiophen-3-yl)benzamide (425.7 mg, yield 88.5%).

Step 4: 3-amino-N-cyclopropyl-4-(thiophen-3-yl)benzamide

N-cyclopropyl-3-nitro-4-(thiophen-3-yl)benzamide (425.7 mg, 1.48 mmol), reduced iron powder (413.3 mg, 7.4 mmol) and ammonium chloride (395.8 mg, 7.4 mmol) were added to a mixed solution of methanol (40 mL) and water (40 mL). The reaction mixture was reacted for 0.5 hour at a temperature of 70° C., and then cooled to room temperature. After filtration, the resulting solid was washed with ethyl acetate, the filtrate was separated, and the organic phase was dried over anhydrous sodium sulphate. The solvent was removed by rotary evaporation of the organic phase to afford 3-amino-N-cyclopropyl-4-(thiophen-3-yl)benzamide (364 mg, yield 95.4%).

Step 5: N-cyclopropyl-4-(thiophen-3-yl)-3-(3-(3-(trifluoromethyl)phenyl)ureido)benzamide

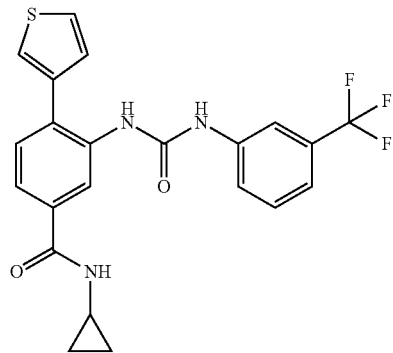

A solution of 3-amino-N-cyclopropyl-4-(thiophen-3-yl)benzamide (70.0 mg, 0.27 mmol) and 3-(trifluoromethyl)phenyl isocyanate (76.7 mg, 0.41 mmol) in dichloromethane (50 mL) was stirred at room temperature for 12 hours. The reaction mixture was purified directly by column chromatography on silica gel to afford N-cyclopropyl-4-(thiophen-3-yl)-3-(3-(3-(trifluoromethyl) phenyl)ureido)benzamide (91.0 mg, yield 75.4%). $^1$H-NMR (400 MHz, DMSO-$d_6$): δ=9.40 (s, 1H), 8.44 (d, J=4.2 Hz, 1H), 8.26 (d, J=1.7 Hz, 1H), 7.98 (m, 2H), 7.72 (m, 2H), 7.61-7.44 (m, 3H), 7.40 (d, J=8.0 Hz, 1H), 7.29 (m, 1H), 2.85 (m, 1H), 0.68 (m, 2H), 0.56 (m, 2H).

Example 24: 1-(5-(1-(cyclopropylamino)ethyl)-2-(thiophen-3-yl)phenyl)-3-(3-(trifluoromethyl) phenyl)urea General Synthetic Method

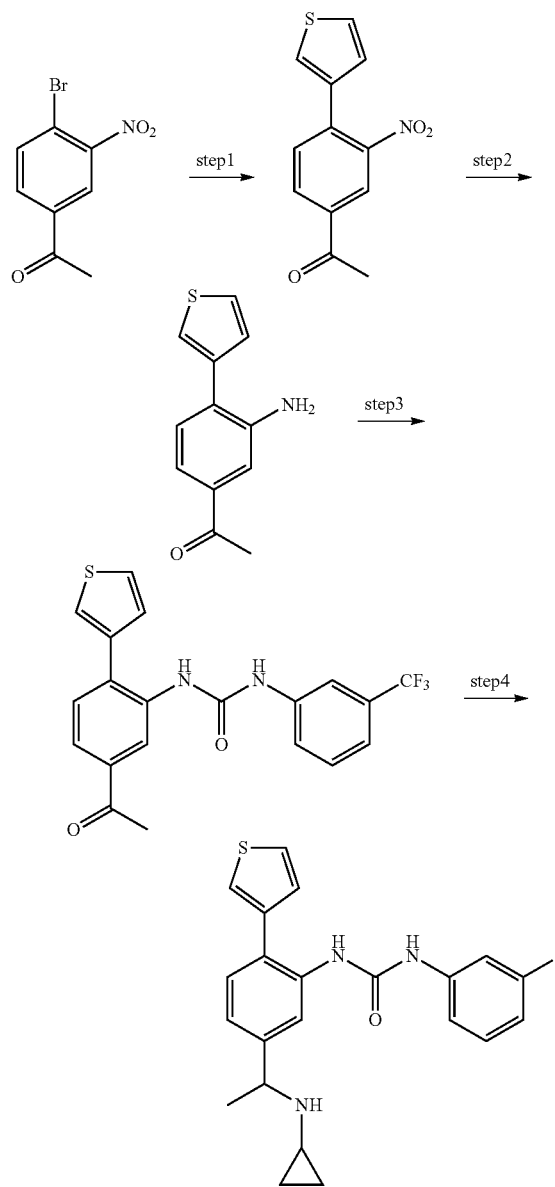

Step 1: 1-(3-nitro-4-(thiophen-3-yl)phenyl)ethanone

Under the protection of nitrogen gas, 4-bromo-3-nitrophenylethanone (500.0 mg, 2.05 mmol), 3-thienylboric acid (315.0 mg, 2.46 mmol), potassium acetate (603.0 mg, 6.15 mmol) and tetrakis(triphenylphosphine)palladium (118.0 mg, 0.1 mmol) were added to a mixed solution of 1,4-dioxane (100 mL) and water (25 mL). The reaction mixture was reacted for 8 hours at a temperature of 90° C., and then cooled to room temperature. The reaction mixture was poured into water, and extracted with ethyl acetate (100 mL×3). The organic phase was combined, and dried over anhydrous sodium sulphate. Ethyl acetate was removed by rotary evaporation of the organic phase, and the residue was purified by column chromatography on silica gel to afford 1-(3-nitro-4-(thiophen-3-yl)phenyl)ethanone (400.0 mg, yield 79.0%).

Step 2: 1-(3-amino-4-(thiophen-3-yl)phenyl)ethanone 1-(3-nitro-4-(thiophen-3-yl)phenyl)ethanone (247.0 mg, 1.0 mmol), reduced iron powder (280.0 mg, 5.0 mmol) and ammonium chloride (268.0 mg, 5.0 mmol) were added to a mixed solution of methanol (40 mL) and water (40 mL). The reaction mixture was reacted for 0.5 hour at a temperature of 70° C., and then cooled to room temperature. After filtration, the resulting solid was washed with ethyl acetate, the filtrate was separated. The organic phase was dried over anhydrous sodium sulphate. The solvent was removed by rotary evaporation of the organic phase to afford 1-(3-amino-4-(thiophen-3-yl)phenyl)ethanone (100.0 mg, yield 46.1%).

Step 3: 1-(5-acetyl-2-(thiophen-3-yl)phenyl)-3-(3-(trifluoromethyl)phenyl)urea

A solution of 1-(3-amino-4-(thiophen-3-yl)phenyl)ethanone (100.0 mg, 0.46 mmol) and 3-(trifluoromethyl)phenyl isocyanate (130.0 mg, 0.69 mmol) in dichloromethane (50 mL) was stirred at room temperature for 12 hours. The reaction mixture was purified directly by column chromatography on silica gel to afford 1-(5-acetyl-2-(thiophen-3-yl)phenyl)-3-(3-(trifluoromethyl) phenyl)urea (178.0 mg, yield 95.6%).

Step 4: 1-(5-(1-(cyclopropylamino)ethyl)-2-(thiophen-3-yl)phenyl)-3-(3-(trifluoromethyl) phenyl)urea

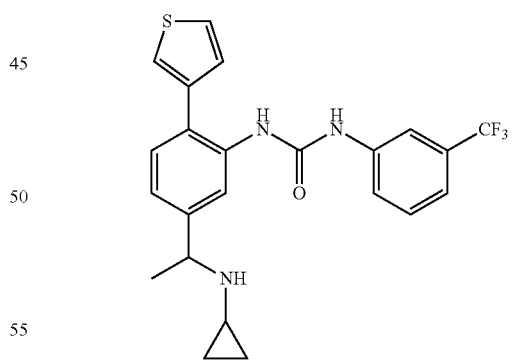

1-(5-Acetyl-2-(thiophen-3-yl)phenyl)-3-(3-(trifluoromethyl)phenyl)urea (70.0 mg, 0.173 mmol) was dissolved in 1,2-dichloroethane (50.0 mL), and then cooled to a temperature of 0° C. Cyclopropylamine (12.0 mg, 0.21 mmol) and 2 drops of acetic acid were added to the reactant, and stirred at room temperature for 10 minutes, and then sodium triacetylborohydride (73.0 mg, 0.35 mmol) was added. The reactant was stirred at room temperature overnight. After the reaction was complete, water was slowly added dropwise to quench the reaction, and the reaction mixture was extracted with dichloromethane. The organic phase was dried over anhydrous sodium sulphate, filtered, and concentrated under reduced pressure. The resulting residue was purified by column chromatography on silica gel to afford the product 1-(5-(1-(cyclopropylamino)ethyl)-2-(thiophen-3-yl)phenyl)-3-(3-(trifluoromethyl)phenyl)urea (50.0 mg, yield 64.8%). $^1$H-NMR (400 MHz, DMSO-d$_6$): δ=9.58 (s, 1H), 8.09-7.88 (m, 3H), 7.75-7.65 (m, 2H), 7.48 (t, J=6.6 Hz, 2H), 7.36 (d, J=7.8 Hz, 1H), 7.31-7.20 (m, 3H), 4.11 (m, 1H), 2.16 (m, 1H), 1.43 (s, 3H), 0.52 (m, 4H).

Example 25: 1-(5-(cyclopropylamino)methyl)-2-(thiophen-3-yl)phenyl)-3-(3-(trifluoromethyl) phenyl)urea

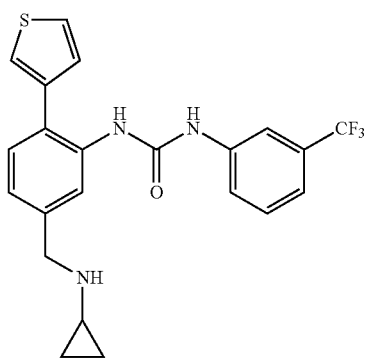

1-(5-(Cyclopropylamino)methyl)-2-(thiophen-3-yl)phenyl)-3-(3-(trifluoromethyl)phenyl)urea was prepared referring to the synthetic method in Example 24. $^1$H-NMR (400 MHz, DMSO-d$_6$): δ=9.37 (s, 1H), 7.93 (s, 1H), 7.81 (s, 1H), 7.72 (s, 1H), 7.59 (dd, J=4.9, 2.9 Hz, 1H), 7.54 (dd, J=7.5, 5.9 Hz, 1H), 7.48-7.37 (m, 2H), 7.18 (dd, J=7.9, 4.0 Hz, 3H), 7.01 (t, J=8.7 Hz, 1H), 3.65 (s, 2H), 2.08 (m, 1H), 0.35 (m, 2H), 0.29 (m, 2H).

Example 26: N-cyclopropyl-1-(4-(thiophen-3-yl)-3-(3-(3-(trifluoromethyl)phenyl)ureido)phenyl) methanesulfonamide

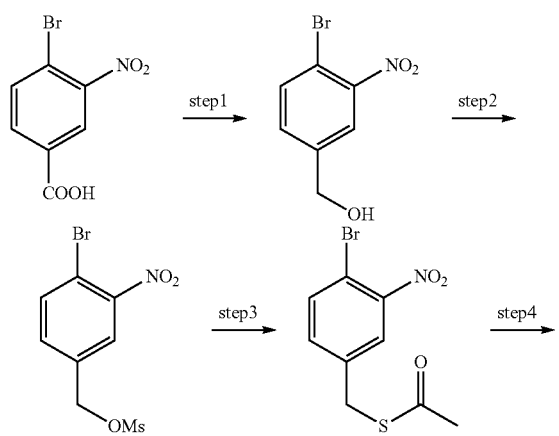

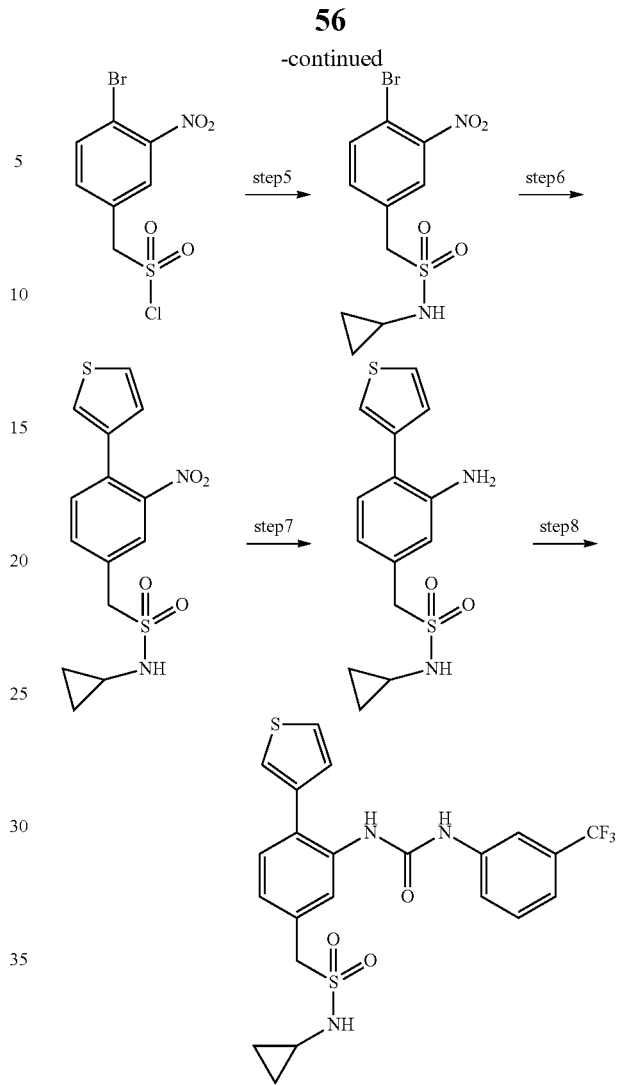

Step 1: (4-bromo-3-nitrophenyl)methanol

Under sufficient purging with nitrogen gas, the raw material 4-bromo-3-nitrobenzoic acid (1.50 g, 6.10 mmol) was dissolved in tetrahydrofuran (150 mL). A 10 M solution of borane in dimethylsulfide (0.65 mL, 6.53 mmol) was slowly added to the reactant, and then was stirred at room temperature for 48 hours. Water was added to quench the reaction, and the reaction mixture was extracted with ethyl ether. The organic phase was washed sequentially with water and saturated saline solution, dried over anhydrous sodium sulphate, filtered, and concentrated under reduced pressure to afford the product (4-bromo-3-nitrophenyl)methanol (1.40 g, yield 99.0%).

Step 2: 4-bromo-3-nitrobenzyl methanesulfonate

The raw material (4-bromo-3-nitrophenyl)methanol (1.40 g, 6.03 mmol) was dissolved in dichloromethane (150 mL), and cooled to a temperature of 0° C. Triethylamine (0.90 g, 9.05 mmol) was added, and then methanesulfonyl chloride (0.76 g, 6.63 mmol) was slowly added dropwise. After the reaction mixture was stirred at room temperature for 2 hours, water was added to quench the reaction, and a saturated aqueous solution of sodium bicarbonate was slowly added dropwise until the pH is basic. The reaction mixture was extracted with dichloromethane. The organic phase was dried over anhydrous sodium sulphate, filtered, and concentrated under reduced pressure to afford the product 4-bromo-3-nitrobenzyl methanesulfonate (1.50 g, yield 80.2%).

Step 3: benzyl 4-bromo-3-nitrothioacetate

The raw material 4-bromo-3-nitrobenzyl methanesulfonate (1.50 g, 4.84 mmol) was dissolved in dimethyl sulfoxide (100 mL), and then potassium thioacetate (0.60 g, 5.32 mmol) was added thereto. After the reaction mixture was stirred at room temperature for 16 hours, water was added to quench the reaction, and the reaction mixture was extracted with dichloromethane. The organic phase was dried over anhydrous sodium sulphate, filtered, and concentrated under reduced pressure. The resulting residue was purified by column chromatography on silica gel to afford the product benzyl 4-bromo-3-nitrothioacetate (0.90 g, yield 64.1%).

Step 4: 4-bromo-3-nitro phenylmethanesulfonyl chloride

Benzyl 4-bromo-3-nitrothioacetate (0.90 g, 3.10 mmol) was dissolved in acetonitrile (100 mL), and cooled to a temperature of 0° C. A mixed solution of N-chlorosuccimide (1.66 g, 12.4 mmol) in acetonitrile (5 mL) and hydrochloric acid (1 mL, 1 N) was slowly added dropwise thereto, and the reaction mixture was further stirred at a temperature of 0° C. for additional 1 hour. Water was added to quench the reaction, and the reaction mixture was extracted with ethyl acetate. The organic phase was dried over anhydrous sodium sulphate, filtered, and concentrated under reduced pressure to afford the product 4-bromo-3-nitrophenylmethanesulfonyl chloride (0.90 g, yield 92.2%).

Step 5: 1-(4-bromo-3-nitrophenyl)-N-cyclopropyl-methanesulfonamide

To a solution of cyclopropylamine (100.0 mg, 1.75 mmol) and pyridine (377.0 mg, 4.77 mmol) in dichloromethane (50 mL) was added the raw material 4-bromo-3-nitrophenyl-methanesulfonyl chloride (500.0 mg, 1.59 mmol) at a temperature of 0° C., and the reaction mixture was stirred at room temperature overnight. Water was added to quench the reaction, and the reaction mixture was extracted with dichloromethane. The organic phase was dried over anhydrous sodium sulphate, filtered, and concentrated under reduced pressure to afford 1-(4-bromo-3-nitrophenyl)-N-cyclopropylmethanesulfonamide (180.0 mg, yield 33.8%).

Step 6: N-cyclopropyl-1-(3-nitro-4-(thiophen-3-yl) phenyl)methanesulfonamide

Under the protection of nitrogen gas, 1-(4-bromo-3-nitrophenyl)-N-cyclopropylmethanesulfonamide (180.0 mg, 0.54 mmol), 3-thienylboric acid (82.0 mg, 0.65 mmol), potassium acetate (160.0 mg, 0.65 mmol) and tetrakis(triphenylphosphine)palladium (30.0 mg, 0.03 mmol) were added to a mixed solution of 1,4-dioxane (100 mL) and water (25 mL). The reaction mixture was reacted for 8 hours at a temperature of 90° C., and then cooled to room temperature. The reaction mixture was poured into water, and extracted with ethyl acetate (100 mL×3). The organic phase was combined, and dried over anhydrous sodium sulphate. Ethyl acetate was removed by rotary evaporation of the organic phase, and the residue was purified by column chromatography on silica gel to afford N-cyclopropyl-1-(3-nitro-4-(thiophen-3-yl)phenyl) methanesulfonamide (150.0 mg, yield 82.5%).

Step 7: 1-(3-amino-4-(thiophen-3-yl)-phenyl)-N-cyclopropyl methanesulfonamide

N-cyclopropyl-1-(3-nitro-4-(thiophen-3-yl)-phenyl) methanesulfonamide (150.0 mg, 0.44 mmol), reduced iron powder (124.0 mg, 2.22 mmol) and ammonium chloride (119.0 mg, 2.22 mmol) were added to a mixed solution of methanol (40 mL) and water (40 mL). The reaction mixture was reacted for 0.5 hour at a temperature of 70° C., and then cooled to room temperature. After filtration, the resulting solid was washed with ethyl acetate, and the filtrate was partitioned. The organic phase was dried over anhydrous sodium sulphate. The solvent was removed by rotary evaporation of the organic phase to afford 1-(3-amino-4-(thiophen-3-yl)-phenyl)-N-cyclopropylmethanesulfonamide (135.0 mg, yield 98.7%).

Step 8: N-cyclopropyl-1-(4-(thiophen-3-yl)-3-(3-(3-(trifluoromethyl)phenyl)ureido)phenyl) methanesulfonamide

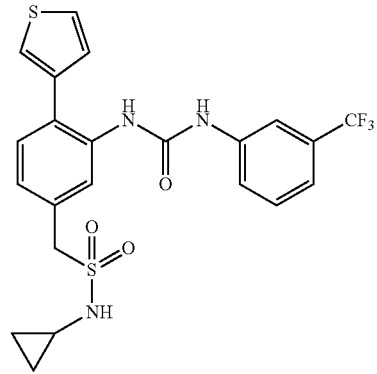

A solution of 1-(3-amino-4-(thiophen-3-yl)-phenyl)-N-cyclopropylmethanesulfonamide (60.0 mg, 0.20 mmol) and 3-(trifluoromethyl)phenyl isocyanate (55.0 mg, 0.29 mmol) in dichloromethane (50 mL) was stirred at room temperature for 12 hours. The reaction mixture was separated directly by column chromatography on silica gel to afford N-cyclopropyl-1-(4-(thiophen-3-yl)-3-(3-(3-(trifluoromethyl)phenyl) ureido)phenyl)methanesulfonamide (40.0 mg, yield 41.4%). $^1$H-NMR (400 MHz, DMSO-$d_6$): δ=9.42 (s, 1H), 8.02 (s, 1H), 7.92 (d, J=13.8 Hz, 2H), 7.70 (m, 2H), 7.49 (m, 3H), 7.33 (d, J=1.9 Hz, 1H), 7.27 (d, J=5.0 Hz, 2H), 7.13 (d, J=7.8 Hz, 1H), 4.37 (s, 2H), 2.52 (m, 1H), 0.66-0.38 (m, 4H).

Example 27: N-(1-(4-(thiophen-3-yl)-3-(3-(3-(trifluoromethyl)phenyl)ureido)phenyl)ethyl) cyclopropanecarboxamide

General Synthetic Method

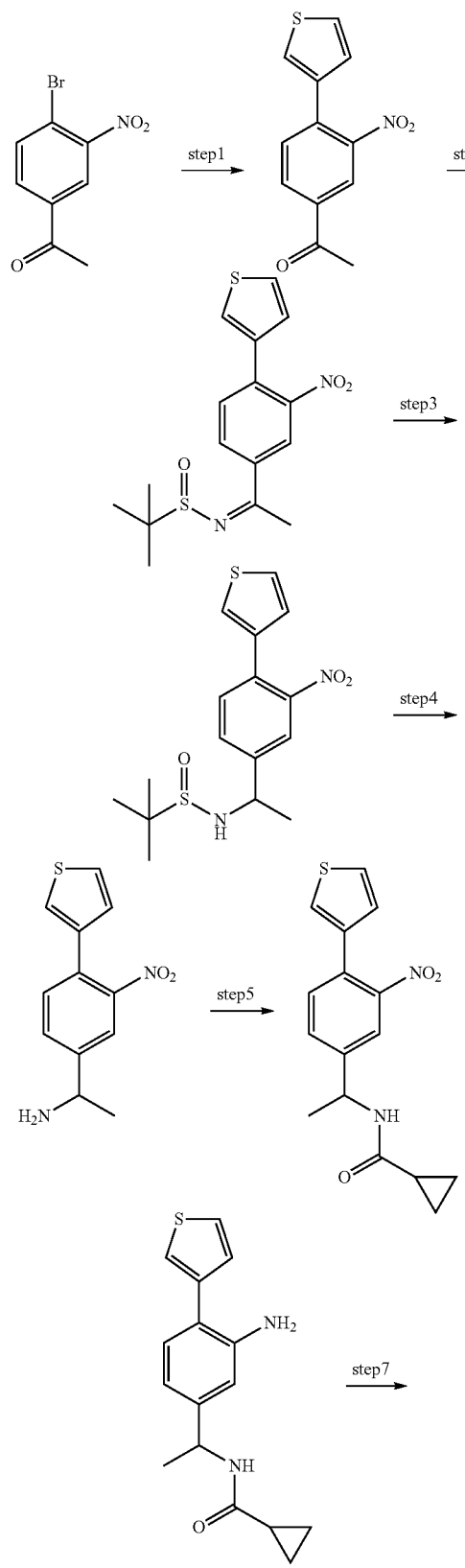

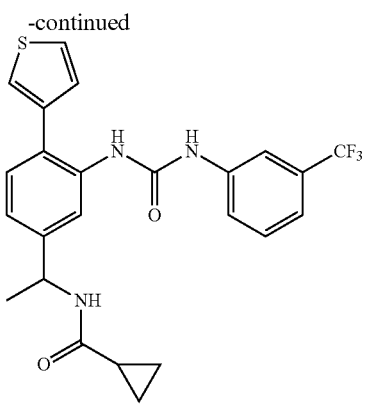

Step 1: 1-(3-nitro-4-(thiophen-3-yl)phenyl)ethanone

Under the protection of nitrogen gas, 4-bromo-3-nitrophenylethanone (3.0 g, 12.3 mmol), 3-thienylboric acid (1.9 g, 14.7 mmol), potassium acetate (3.6 g, 36.9 mmol) and tetrakis(triphenylphosphine)palladium (0.7 g, 0.6 mmol) were added to a mixed solution of 1,4-dioxane (160 mL) and water (40 mL). The reaction mixture was reacted for 8 hours at a temperature of 90° C., and then cooled to room temperature. The reaction mixture was poured into water, and extracted with ethyl acetate (150 mL×3). The organic phase was combined, and dried over anhydrous sodium sulphate. Ethyl acetate was removed by rotary evaporation of the organic phase, and the residue was purified by column chromatography on silica gel to afford 1-(3-nitro-4-(thiophen-3-yl)phenyl)ethanone (2.6 g, yield 85.5%).

Step 2: 2-methyl-N-(1-(3-nitro-4-(thiophen-3-yl)phenyl)ethylidene)propane-2-sulfinamide To a mixture of the raw materials 1-(3-nitro-4-(thiophen-3-yl)phenyl)ethanone (500 mg, 2.02 mmol), tert-butylsulfinamide (270 mg, 2.22 mmol) and tetraethyl titanate (911 mg, 4.00 mmol) was added tetrahydrofuran (100 mL). The resulting mixture was heated for 12 hours at reflux, then cooled to room temperature, and concentrated under reduced pressure. The resulting residue was purified by column chromatography on silica gel to afford 2-methyl-N-(1-(3-nitro-4-(thiophen-3-yl)phenyl)ethylidene)propane-2-sulfinamide (300 mg, yield 42.3%)

Step 3: 2-methyl-N-(1-(3-nitro-4-(thiophen-3-yl)phenyl)ethyl)propane-2-sulfinamide The raw material 2-methyl-N-(1-(3-nitro-4-(thiophen-3-yl)phenyl)ethylidene)propane-2-sulfinamide (300 mg, 0.86 mmol) was dissolved in tetrahydrofuran (100 mL), and cooled to a temperature of 0° C. Sodium borohydride (65 mg, 1.71 mmol) was added to the reactant in portions, and then the reaction mixture was warmed to room temperature and stirred for 2 hours. Saturated aqueous solution of ammonium chloride was added to quench the reaction, and the reaction mixture was extracted with ethyl acetate. The organic phase was dried over anhydrous sodium sulphate, filtered, and concentrated under reduced pressure to afford 2-methyl-N-(1-(3-nitro-4-(thiophen-3-yl)phenyl)ethyl)propane-2-sulfinamide (200 mg, yield 66.3%).

Step 4: 1-(3-nitro-4-(thiophen-3-yl)phenyl)ethylamine

2-Methyl-N-(1-(3-nitro-4-(thiophen-3-yl)phenyl)ethyl) propane-2-sulfinamide (200 mg, 0.57 mmol) was dissolved in methanol (100 mL), and a 6M aqueous solution (10 mL) of hydrochloric acid was added thereto. The reaction mixture was stirred at room temperature for 12 hours, and then concentrated under reduced pressure. The resulting residue was dissolved in water, adjusted to pH 7-8 with ammonia liquor, and extracted with ethyl acetate. The organic phase was dried over anhydrous sodium sulphate, filtered, and concentrated under reduced pressure to afford 1-(3-nitro-4-(thiophen-3-yl)phenyl)ethylamine (130 mg, yield 92.3%).

Step 5: N-(1-(3-nitro-4-(thiophen-3-yl)phenyl)ethyl) cyclopropanecarboxamide To a solution of the raw materials 1-(3-nitro-4-(thiophen-3-yl)phenyl)ethylamine (130 mg, 0.52 mmol) and triethylamine (212 mg, 2.10 mmol) in dichloromethane (50 mL) was added cyclopropanoyl chloride (64 mg, 0.62 mmol). After the reaction mixture was stirred at room temperature for 1 hour, water was added to quench the reaction, and the reaction mixture was extracted with dichloromethane. The organic phase was dried over anhydrous sodium sulphate, filtered, and concentrated under reduced pressure to afford N-(1-(3-nitro-4-(thiophen-3-yl)phenyl)ethyl)cyclopropanecarboxamide (150 mg, yield 90.6%).

Step 6: N-(1-(3-amino-4-(thiophen-3-yl)phenyl) ethyl)cyclopropanecarboxamide N-(1-(3-nitro-4-(thiophen-3-yl)phenyl)ethyl)cyclopropanecarboxamide (150.0 mg, 0.47 mmol), reduced iron powder (140 mg, 2.27 mmol) and ammonium chloride (128 mg, 2.27 mmol) were added to a mixed solution of methanol (40 mL) and water (40 mL). The reaction mixture was reacted for 0.5 hour at a temperature of 70° C., and then cooled to room temperature. After filtration, the resulting solid was washed with ethyl acetate, and the filtrate was partitioned. The organic phase was dried over anhydrous sodium sulphate, and the solvent was removed by rotary evaporation of the organic phase to afford N-(1-(3-amino-4-(thiophen-3-yl)phenyl)ethyl)cyclopropanecarboxamide (100 mg, yield 73.6%).

Step 7: N-(1-(4-(thiophen-3-yl)-3-(3-(3-(trifluoromethyl)phenyl)ureido)phenyl)ethyl) cyclopropanecarboxamide A solution of N-(1-(3-amino-4-(thiophen-3-yl)phenyl)ethyl)cyclopropanecarboxamide (100.0 mg, 0.35 mmol) and 3-(trifluoromethyl)phenyl isocyanate (98.0 mg, 0.52 mmol) in dichloromethane (50 mL) was stirred at room temperature for 12 hours. The reaction mixture was separated directly by column chromatography on silica gel to afford N-(1-(4-(thiophen-3-yl)-3-(3-(3-(trifluoromethyl) phenyl)ureido) phenyl)ethyl)cyclopropanecarboxamide (150.0 mg, yield 90.7%). $^1$H-NMR (400 MHz, DMSO-d$_6$): δ=9.39 (s, 1H), 8.54 (d, J=7.9 Hz, 1H), 8.00 (s, 1H), 7.86-7.75 (m, 2H), 7.66 (dd, J=4.9, 2.9 Hz, 1H), 7.60 (dd, J=2.8, 1.1 Hz, 1H), 7.45 (d, J=5.1 Hz, 2H), 7.28-7.18 (m, 3H), 7.03 (dd, J=7.9, 1.5 Hz, 1H), 4.87 (p, J=7.0 Hz, 1H), 1.63-1.49 (m, 1H), 1.34 (d, J=7.0 Hz, 3H), 0.73-0.45 (m, 4H).

Example 28: N-(4-(thiophen-3-yl)-3-(3-(3-(trifluoromethyl)phenyl)ureido)benzyl) cyclopropanecarboxamide

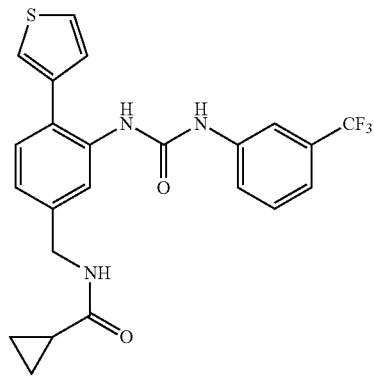

N-(4-(thiophen-3-yl)-3-(3-(3-(trifluoromethyl)phenyl) ureido)benzyl)cyclopropanecarboxamide was prepared referring to the synthetic method in Example 27. $^1$H-NMR (400 MHz, DMSO-d$_6$): J=9.35 (s, 1H), 8.57 (t, J=5.9 Hz, 1H), 7.97 (s, 1H), 7.81 (s, 1H), 7.72 (d, J=1.4 Hz, 1H), 7.64 (dd, J=4.9, 2.9 Hz, 1H), 7.57 (dd, J=2.9, 1.3 Hz, 1H), 7.47-7.38 (m, 2H), 7.22 (m, 2H), 7.19 (dd, J=4.9, 1.3 Hz, 1H), 6.97 (dd, J=7.9, 1.6 Hz, 1H), 4.22 (s, 2H), 1.64-1.48 (m, 1H), 0.75-0.53 (m, 4H).

Example 29: N-(4-(thiophen-3-yl)-3-(3-(3-(trifluoromethyl)phenyl)ureido)benzyl) cyclopropylsulfonamide

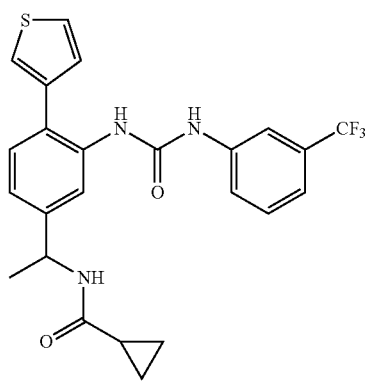

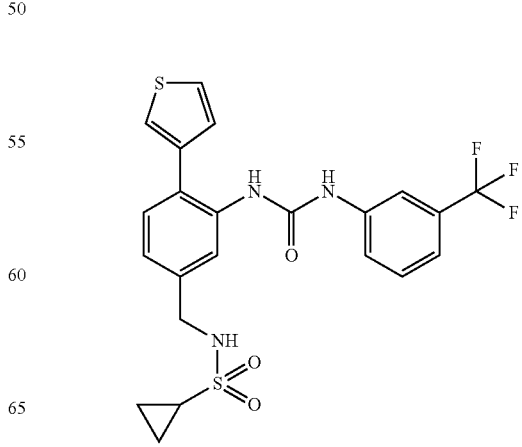

N-(4-(thiophen-3-yl)-3-(3-(3-(trifluoromethyl)phenyl)ureido)benzyl)cyclopropylsulfonamide was prepared referring to the synthetic method in Example 27. $^1$H-NMR (400 MHz, DMSO-d$_6$): J=9.40 (s, 1H), 8.01 (s, 1H), 7.87 (d, J=3.5 Hz, 2H), 7.73-7.60 (m, 3H), 7.51-7.46 (m, 2H), 7.33-7.22 (m, 3H), 7.16-7.08 (m, 1H), 4.20 (d, J=6.4 Hz, 2H), 2.61-2.49 (m, 1H), 0.91 (m, 4H).

Experimental Example 1

Determining IDH2 Inhibitory Activity

The inhibitory activity of the compounds of the present application against IDH2 (R172K, 40-end) was determined by using the following method, which was expressed as IC$_{50}$ values, i.e., the concentrations of the compounds required to achieve 50% inhibition of IDH2 activity.

Materials and Methods:

The inhibitory activity of a compound against IDH2 (R172K, 40-end) was determined by the decrease of a helper factor NADPH. The test compound was pre-incubated with an enzyme and NADPH, and then a reaction was initiated by the addition of a-KG, and performed for 120 minutes under a linear condition. Then, the reaction was terminated by the addition of diaphorase (lipoamide dehydrogenase) and the corresponding substrate resazurin. Diaphorase terminated the IDH2m reaction by decreasing the available helper factor NADPH, which oxidized NADPH to NADP, and reduced resazurin to highly fluorescent resorufin. The amount of remaining helper factor NADPH after a specific reaction time was quantified via an easily detectable fluorophore.

Specifically, 2.5 μl of a 3-fold gradient diluted test compound was added to a 384-well plate, and then 5 μl of a reaction buffer (20 mM Tris-HCl, PH7.5; 150 mM NaCl; 10 mM MgC12; 10 mM MnCl2; 0.4 mg/ml BSA and 2 mM DTT) containing 80 nM IDH2 (R172K, 40-end) and 40 μM NADPH was added. Then, the resulting test mixture was incubated for 120 minutes at a temperature of 23° C., and then 2.5 μl of the reaction buffer containing 4 mM α-KG was added to initiate the reaction. After incubating for 120 minutes at room temperature, 5 μl of a termination mixture (0.4 U/ml diaphorase and 40 μM resazurin) prepared with the reaction buffer was added to convert resazurin to resorufin to determine the remaining NADPH. After incubating for 10 minutes at a temperature of 23° C., a fluorescence value was determined through Flexstation 3 at Ex535/Em595.

The inhibitory activity of test compound against IDH2 was shown in Table 1.

TABLE 1

| Example No. | IC$_{50}$(nM) | Example No. | IC$_{50}$(nM) |
|---|---|---|---|
| 1 | 14.20 | 16 | 75.82 |
| 2 | 45.52 | 17 | 138.2 |
| 3 | 62.35 | 18 | 1231 |
| 4 | 56.51 | 19 | 87.47 |
| 5 | 29.54 | 20 | 361.8 |
| 10 | 391.4 | 21 | 622.5 |
| 13 | 105.70 | 23 | 550.6 |
| 14 | 69.93 | 24 | 312.0 |
| 15 | 65.66 | 27 | 82.89 |
| 12 | 53.75 | 28 | 55.01 |

Experimental Example 2

Measuring Pharmacokinetics Parameters

The pharmacokinetic parameters of compounds of the present application were determined by using the following method.

Healthy male adult rats (7-9 weeks old) were used in this study. Each group of animals (3 male rats) was intragastrically administered once at a single dose of 5 mg/kg with 10% DMSO+70% PEG400+20% NS as adjuvants. The animals in the intragastric administration group were fasted overnight before this study. The fasting time period was from 10 hours before administration to 4 hours after administration.

Blood samples were taken at 0.25, 0.5, 1, 2, 4, 6, 8 and 24 h after administration. The animals were anesthetized with isoflurane using an animal anesthesia machine, and then 0.3 mL whole blood samples were taken from the fundus venous plexus. The blood samples were placed in heparin anticoagulant tubes, and centrifuged for 5 min at 4° C. and 4000 rpm. The resulting plasmas were transferred to centrifuge tubes, and stored at −80° C. until analysis.

Verified LC-MS/MS method was used to analyze the plasma samples. Plasma concentration-time data of animals were analyzed using WinNonlin (Professional Edition, version 6.3; Pharsight Company) software. The non-compartmental model was introduced for concentration analysis. The pharmacokinetic parameters of the compounds were calculated, and shown in Table 3.

TABLE 3

| Example | 5 | 28 | AGI-6780 |
|---|---|---|---|
| Dose (mg/kg) | 5 | 5 | 5 |
| T$_{1/2}$ (hr) | 4.37 | 2.34 | 1.49 |
| T$_{max}$ (hr) | 0.42 | 0.33 | 2.83 |
| C$_{max}$ (ng/mL) | 494.6 | 414.1 | 191.1 |
| AUC$_{0-inf}$ (hr*ng/mL) | 858.2 | 844.5 | 559.3 |

Conclusions: the compounds in Example 5 and Example 28 had a very good metabolism in vivo and a long half-life, and furthermore, had a higher plasma concentration than an IDH2 inhibitor AG-6780 at the same dose.

What is claimed is:
1. A compound of formula I:

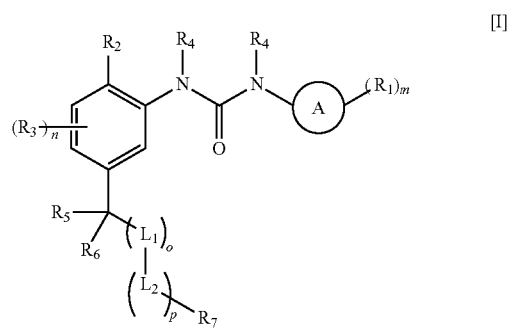

wherein:
Ring A is selected from a benzene ring or a 5- or 6-membered heteroaromatic ring containing 1 or 2 heteroatoms selected from the group consisting of N, O and S;

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of the Ring A to which they are attached, form a 5- to 7-membered cycloalkyl ring or a 5- to 7-membered heteroalicyclic ring, and a methylene of the 5- to 7-membered cycloalkyl ring or a methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

each $R_3$ is independently selected from the group consisting of hydrogen, halogen, $C_{1-3}$ haloalkyl, hydroxy, amino and $C_{1-6}$ alkyl;

each $R_4$ is independently selected from hydrogen or $C_{1-6}$ alkyl;

$R_5$ and $R_6$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or one of $R_5$ and $R_6$ is an oxygen atom of carbonyl, and the other is absent; or $R_5$ and $R_6$, together with the carbon atom to which they are attached, form a 3- to 7-membered cycloalkyl ring or a 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

$L_1$ and $L_2$ are each independently selected from the group consisting of —C(O)—, —N($R_4$)—, and —S(O)$_2$—, and $L_1$ is different from $L_2$;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl;

m and n are independently 1, 2 or 3; and o and p are each independently selected from 0 or 1, but cannot both be 0;

or a pharmaceutically acceptable salt or hydrate thereof.

2. The compound according to claim 1, wherein the compound is a compound of formula II:

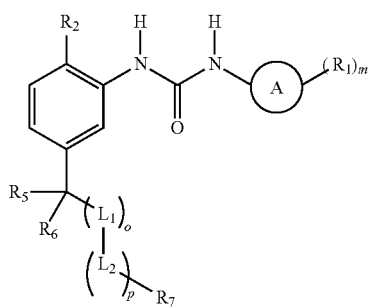

[II]

wherein:

Ring A is selected from a benzene ring or a 5- or 6-membered heteroaromatic ring containing 1 or 2 N atoms;

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of the Ring A to which they are attached, form a 5- to 7-membered cycloalkyl ring or a 5- to 7-membered heteroalicyclic ring, and a methylene of the 5- to 7-membered cycloalkyl ring or a methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

$R_5$ and $R_6$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or one of $R_5$ and $R_6$ is an oxygen atom of carbonyl, and the other is absent; or $R_5$ and $R_6$, together with the carbon atom to which they are attached, form a 3- to 7-membered cycloalkyl ring or a 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

$L_1$ and $L_2$ are each independently selected from the group consisting of —C(O)—, —N($R_4$)—, and —S(O)$_2$—; $L_1$ is different from $L_2$; and $R_4$ is selected from hydrogen or $C_{1-6}$ alkyl;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl;

m is 1, 2 or 3; and o and p are each independently selected from 0 or 1, but cannot both be 0;

or a pharmaceutically acceptable salt or hydrate thereof.

3. The compound according to claim 1, wherein the compound is a compound of formula III:

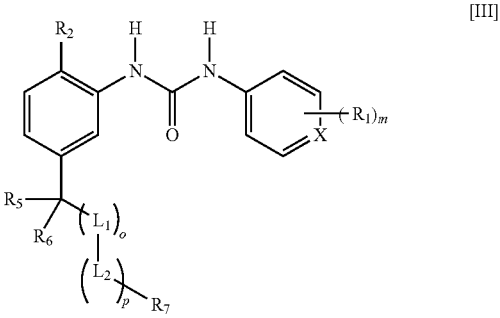

[III]

wherein:

X is selected from CH or N;

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of benzene ring or the atoms of pyridine ring to which they are attached, form a 5- to 7-membered cycloalkyl ring or a 5- to 7-membered heteroalicyclic ring, and a methylene of the 5- to 7-membered cycloalkyl ring or a methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

$R_5$ and $R_6$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or one of $R_5$ and $R_6$ is an oxygen atom of carbonyl, and the other is absent; or $R_5$ and $R_6$, together with the carbon atom to which they are attached, form a 3- to 7-membered cycloalkyl ring or a 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

$L_1$ and $L_2$ are each independently selected from the group consisting of —C(O)—, —N($R_4$)—, and —S(O)$_2$—; $L_1$ is different from $L_2$; and $R_4$ is selected from hydrogen or $C_{1-6}$ alkyl;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl;

m is 1, 2 or 3; and o and p are each independently selected from 0 or 1, but cannot both be 0;

or a pharmaceutically acceptable salt or hydrate thereof.

4. The compound according to claim 1, wherein:

the Ring A is selected from a benzene ring or a 6-membered heteroaromatic ring containing one N atom;

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of the Ring A to which they are attached, form the 5- to 7-membered cycloalkyl ring or the 5- to 7-membered heteroalicyclic ring, and the methylene of the 5- to 7-membered cycloalkyl ring or the methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

$R_5$ and $R_6$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or one of $R_5$ and $R_6$ is an oxygen atom of carbonyl, and the other is absent; or $R_5$ and $R_6$, together with the carbon atom to which they are attached, form the 3- to 7-membered cycloalkyl ring or the 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

-($L_1$)$_o$-($L_2$)$_p$- is —C(O)—N($R_4$)—, —N($R_4$)—C(O)—, —S(O)$_2$—N($R_4$)—, —N($R_4$)—S(O)$_2$—, or —N($R_4$)—, wherein each $R_4$ is selected from hydrogen or $C_{1-6}$ alkyl;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl; and m is 1, 2 or 3.

5. The compound according to claim 1, wherein:

the Ring A is selected from a benzene ring or a 6-membered heteroaromatic ring containing one N atom;

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of the Ring A to which they are attached, form the 5- to 7-membered cycloalkyl ring or the 5- to 7-membered heteroalicyclic ring, and the methylene of the 5- to 7-membered cycloalkyl ring or the methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

$R_5$ and $R_6$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or $R_5$ and $R_6$, together with the carbon atom to which they are attached, form the 3- to 7-membered cycloalkyl ring or the 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

-($L_1$)$_o$-($L_2$)$_p$- is —C(O)—N($R_4$)—, —N($R_4$)—C(O)—, or —N($R_4$)—, wherein each $R_4$ is selected from hydrogen or $C_{1-6}$ alkyl;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl; and m is 1, 2 or 3.

6. The compound according to claim 1, wherein:

the Ring A is selected from a benzene ring or a 6-membered heteroaromatic ring containing one N atom;

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of the ring A to which they are attached, form the 5- to 7-membered cycloalkyl ring or the 5- to 7-membered heteroalicyclic ring, and the methylene of the 5- to 7-membered cycloalkyl ring or the methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

$R_5$ and $R_6$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or $R_5$ and $R_6$, together with the carbon atom to which they are attached, form the 3- to 7-membered cycloalkyl ring or the 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

-($L_1$)$_o$-($L_2$)$_p$- is —C(O)—N($R_4$)—, or —N($R_4$)—C(O)—, wherein each $R_4$ is selected from hydrogen or $C_{1-6}$ alkyl;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl; and m is 1, 2 or 3.

7. The compound according to claim 1, wherein: m is 1 or 2; each $R_1$ is independently selected from the group consisting of halogen, monofluoromethyl, difluoromethyl, trifluoromethyl, monofluoroethyl, difluoroethyl, trifluoroethyl, tetrafluorethyl, pentafluorethyl, monochloromethyl, dichloromethyl and trichloromethyl; or two adjacent $R_1$ groups, together with the atoms of the Ring A to which they are attached, form the 5- to 7-membered heteroalicyclic ring, and the methylene of the 5- to 7-membered heteroalicyclic ring may optionally further form one carbonyl; preferably, m is 1 or 2; each $R_1$ is independently selected from fluoro or trifluoromethyl; or two adjacent $R_1$ groups, together with the atoms of the Ring A to which they are attached, form the 5-membered nitrogen-containing heteroalicyclic ring, and the methylene of the 5-membered nitrogen-containing heteroalicyclic ring may optionally form one carbonyl.

8. The compound according to claim 3, wherein:

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of the benzene ring or the atoms of the pyridine ring to which they are attached, form the 5- to 7-membered cycloalkyl ring or the 5- to 7-membered heteroalicyclic ring, and the methylene of the 5- to 7-membered cycloalkyl ring or the methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

$R_5$ and $R_6$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or one of $R_5$ and $R_6$ is an oxygen atom of carbonyl, and the other is absent; or $R_5$ and $R_6$, together with the carbon atom to which they are attached, form the 3- to 7-membered cycloalkyl ring or the 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

-$(L_1)_o$-$(L_2)_p$- is —C(O)—N($R_4$)—, —N($R_4$)—C(O)—, —S(O)$_2$—N($R_4$)—, —N($R_4$)—S(O)$_2$—, or —N($R_4$)—, wherein each $R_4$ is selected from hydrogen or $C_{1-6}$ alkyl;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl; and m is 1, 2 or 3.

9. The compound according to claim 3, wherein:

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of the benzene ring or the atoms of the pyridine ring to which they are attached, form the 5- to 7-membered cycloalkyl ring or the 5- to 7-membered heteroalicyclic ring, and the methylene of the 5- to 7-membered cycloalkyl ring or the methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

$R_5$ and $R_6$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or $R_5$ and $R_6$, together with the carbon atom to which they are attached, form the 3- to 7-membered cycloalkyl ring or the 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

-$(L_1)_o$-$(L_2)_p$- is —C(O)—N($R_4$)—, —N($R_4$)—C(O)—, or —N($R_4$)—, wherein each $R_4$ is selected from hydrogen or $C_{1-6}$ alkyl;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl; and m is 1, 2 or 3.

10. The compound according to claim 3, wherein:

each $R_1$ is independently selected from the group consisting of halogen, $C_{1-3}$ haloalkyl, carboxy, amino, $C_{1-6}$ alkyl, $C_{3-6}$ cycloalkyl and $C_{3-6}$ heteroalicyclyl; or two adjacent $R_1$ groups, together with the atoms of the benzene ring or the atoms of the pyridine ring to which they are attached, form the 5- to 7-membered cycloalkyl ring or the 5- to 7-membered heteroalicyclic ring, and the methylene of the 5- to 7-membered cycloalkyl ring or the methylene of the 5- to 7-membered heteroalicyclic ring may optionally further form one or two carbonyl groups;

$R_2$ is selected from phenyl or 5- or 6-membered heteroaryl containing 1 or 2 heteroatoms selected from the group consisting of N, O and S, and may be optionally substituted with one or more $R_8$;

$R_5$ and $R_6$ are each independently selected from the group consisting of hydrogen, halogen, hydroxy, amino, $C_{1-6}$ alkyl, $C_{2-6}$ alkenyl, $C_{3-6}$ cycloalkyl and $C_{3-6}$ heteroalicyclyl; or $R_5$ and $R_6$, together with the carbon atom to which they are attached, form the 3- to 7-membered cycloalkyl ring or the 3- to 7-membered heteroalicyclic ring, and the 3- to 7-membered cycloalkyl ring or the 3- to 7-membered heteroalicyclic ring may be further optionally substituted with $C_{1-6}$ alkyl, halogen, hydroxy or amino;

-$(L_1)_o$-$(L_2)_p$- is —C(O)—N($R_4$)—, or —N($R_4$)—C(O)—, wherein each $R_4$ is selected from hydrogen or $C_{1-6}$ alkyl;

$R_7$ is selected from the group consisting of $C_{1-6}$ alkyl, $C_{3-6}$ cycloalkyl and $C_{3-6}$ heteroalicyclyl, and may be optionally substituted with one or more $R_9$;

each $R_8$ and each $R_9$ are independently selected from the group consisting of halogen, hydroxy, amino, cyano, $C_{1-3}$ haloalkyl, $C_{1-6}$ alkyl and $C_{3-6}$ heteroalicyclyl; and m is 1, 2 or 3.

11. The compound according to claim 3, wherein: m is 1 or 2; and each $R_1$ is independently selected from the group consisting of halogen, monofluoromethyl, difluoromethyl, trifluoromethyl, monofluoroethyl, difluoroethyl, trifluoroethyl, tetrafluorethyl, pentafluorethyl, monochloromethyl, dichloromethyl and trichloromethyl; or two adjacent $R_1$ groups, together with the atoms of the benzene ring or the atoms of the pyridine ring to which they are attached, form the 5- to 7-membered heteroalicyclic ring, and the methylene of the 5- to 7-membered heteroalicyclic ring may optionally further form one carbonyl; preferably, m is 1 or 2; and each $R_1$ is independently selected from fluoro or trifluoromethyl; or two adjacent $R_1$ groups, together with the atoms of the benzene ring or the atoms of the pyridine ring to which they are attached, form the 5-membered nitrogen-containing heteroalicyclic ring, and the methylene of the 5-membered nitrogen-containing heteroalicyclic ring may optionally form one carbonyl.

12. The compound according to claim 1, wherein: $R_2$ is selected from the group consisting of phenyl, furyl, thienyl, pyrrolyl, pyrazolyl, imidazolyl, pyridyl, pyrimidyl, pyridazinyl, pyrazinyl, thiazolyl, isothiazolyl, oxazolyl, isooxazolyl, tetrazolyl and triazinyl, and may be optionally substituted with one or more $R_8$; and each $R_8$ is independently selected from $C_{1-3}$ haloalkyl or $C_{1-6}$ alkyl; preferably, $R_2$ is selected from the group consisting of phenyl, thienyl, pyrazolyl and pyridinyl, and may be optionally substituted with one or more $R_8$; and each $R_8$ is independently selected from trifluoromethyl or methyl.

13. The compound according to claim 1, wherein $R_5$ and $R_6$ are each independently selected from the group consisting of hydrogen, fluoro, chloro, bromo, amino, methyl, ethyl, propyl and isopropyl, or $R_5$ and $R_6$, together with the carbon atom to which they are attached, form cyclopropane, cyclobutane, cyclopentane, cyclohexane, piperidine or pyrrolidine; preferably, $R_5$ and $R_6$ are each independently selected from the group consisting of hydrogen, fluoro, amino, methyl and ethyl, or $R_5$ and $R_6$, together with the carbon atom to which they are attached, form cyclopropane, cyclobutane or piperidine.

14. The compound according to claim 1, wherein: $-(L_1)_o-(L_2)_p-$ is —C(O)—NH—, or —NH—C(O)—.

15. The compound according to claim 1, wherein: $R_7$ is selected from the group consisting of methyl, ethyl, propyl, butyl, pentyl, cyclopropyl, cyclobutyl, cyclopentyl, cyclohexyl and $C_{3-6}$ heteroalicyclyl containing one heteroatom selected from O or N, and may be optionally substituted with one or more $R_9$; each $R_9$ is independently selected from the group consisting of halogen, hydroxy, cyano and $C_{1-6}$ alkyl; preferably, $R_7$ is selected from the group consisting of ethyl, propyl, butyl, pentyl, cyclopropyl, cyclobutyl, oxetanyl and azetidinyl, and may be optionally substituted with 1 to 3 $R_9$; and each $R_9$ is independently selected from the group consisting of fluoro, hydroxy, cyano and methyl.

16. The compound according to claim 1, wherein the compound is selected from the group consisting of

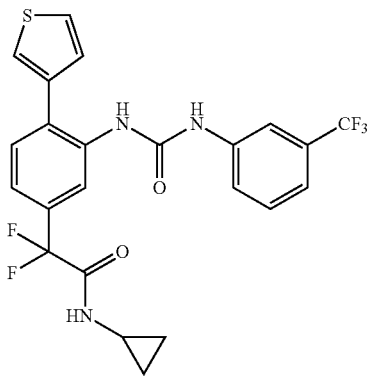

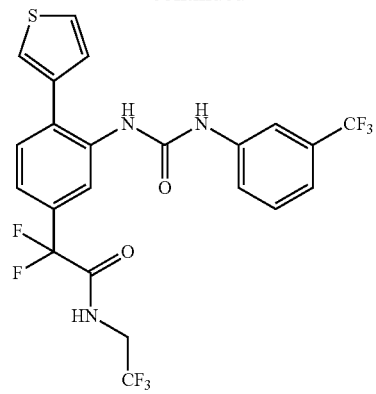

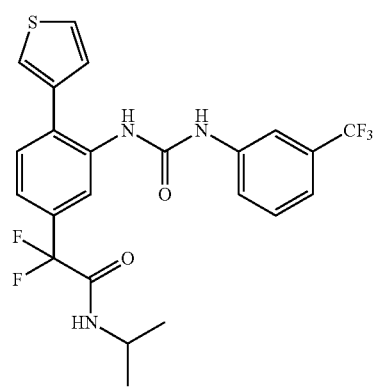

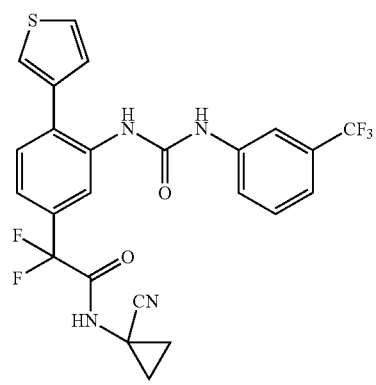

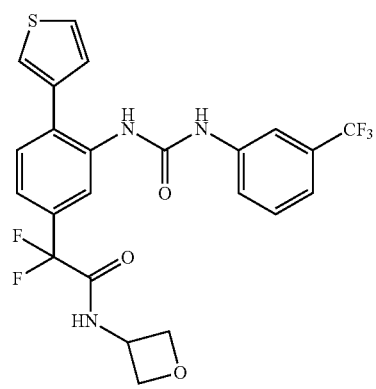

73
-continued
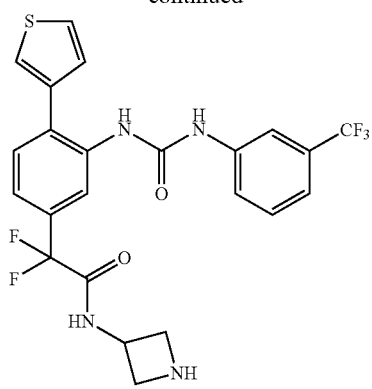
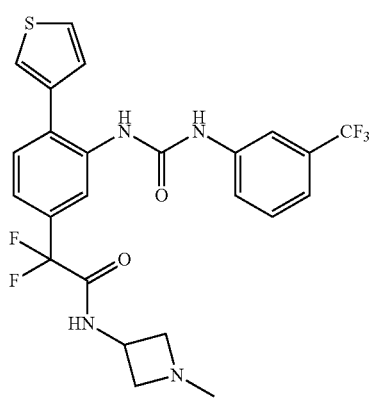
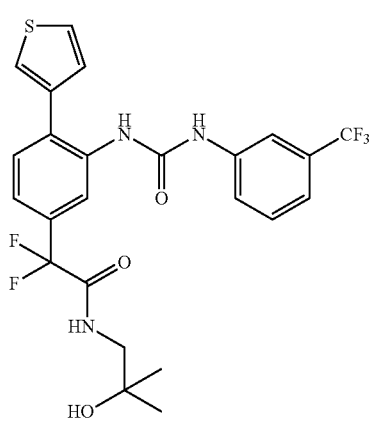
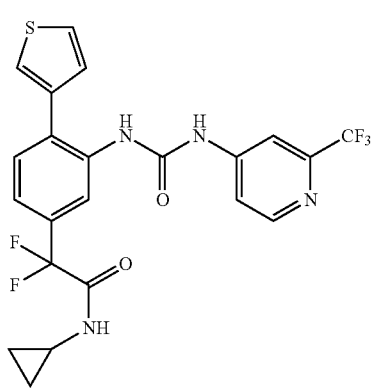
74
-continued
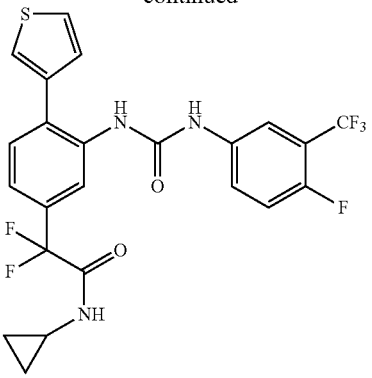
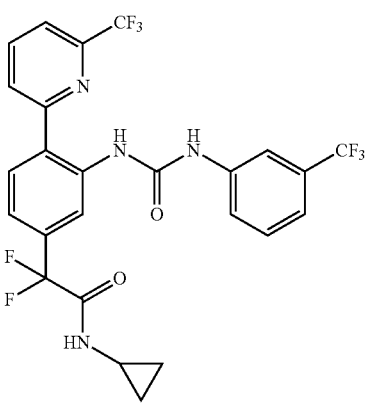
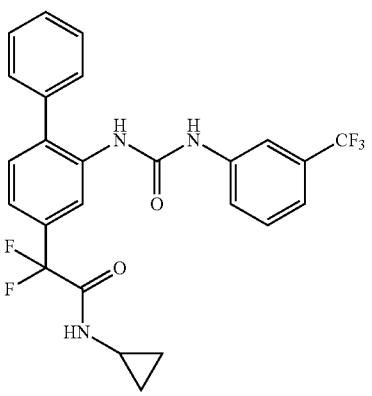
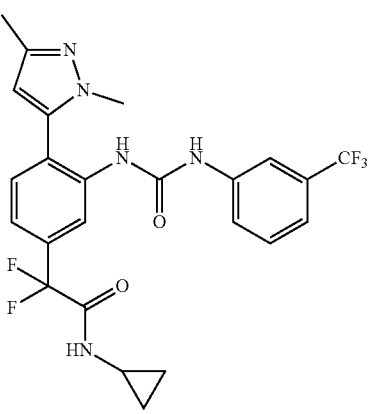

75
-continued
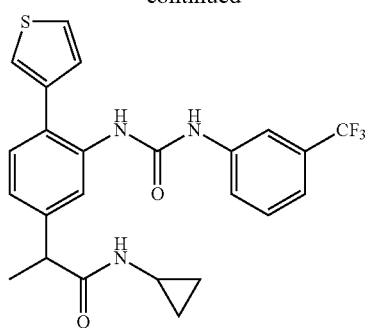
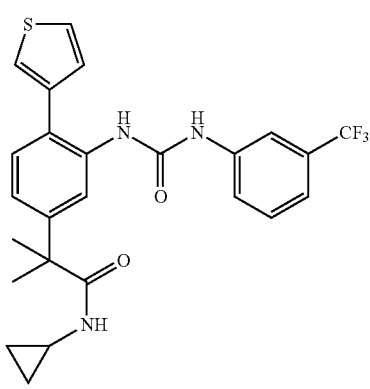
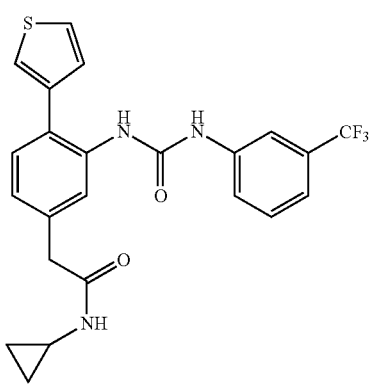
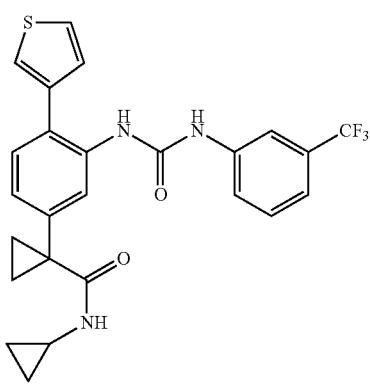
76
-continued
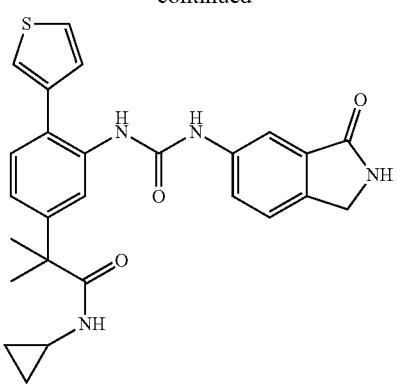
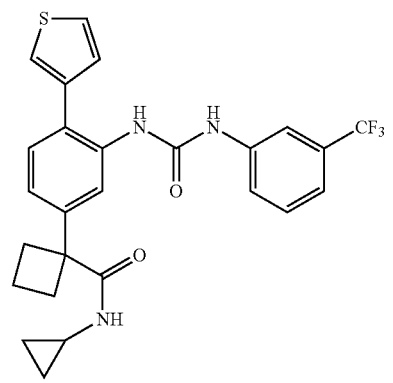
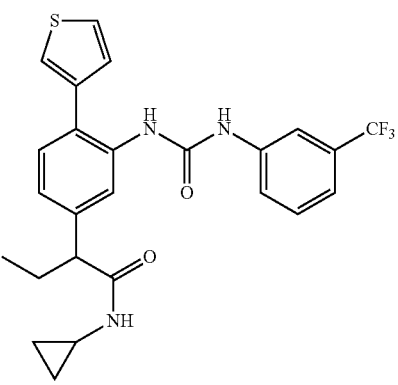
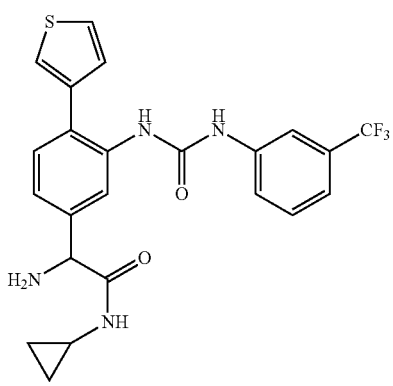 [SMILES: NC(C(=O)NC1CC1)c1ccc(-c2ccsc2)c(NC(=O)Nc2cccc(C(F)(F)F)c2)c1]

-continued
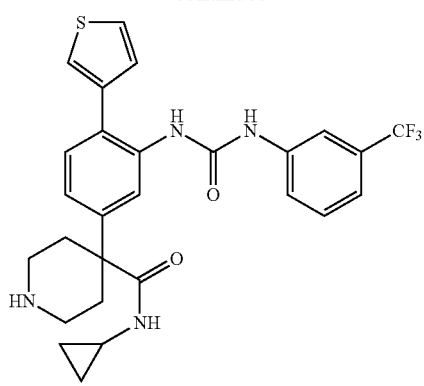 [SMILES: O=C(Nc1cccc(C(F)(F)F)c1)Nc1cc(C2(C(=O)NC3CC3)CCNCC2)ccc1-c1ccsc1]
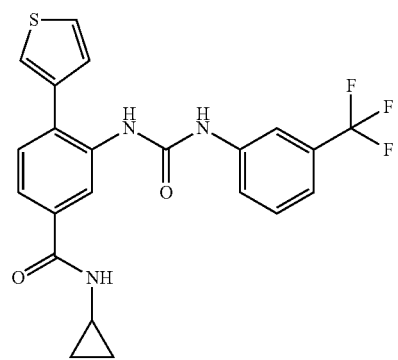 [SMILES: O=C(Nc1cccc(C(F)(F)F)c1)Nc1cc(C(=O)NC2CC2)ccc1-c1ccsc1]
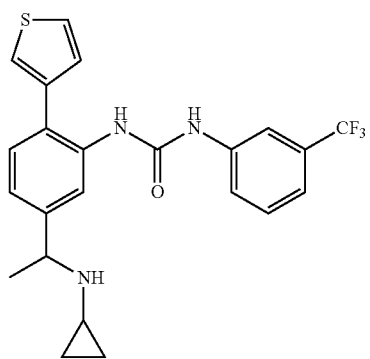 [SMILES: CC(NC1CC1)c1ccc(-c2ccsc2)c(NC(=O)Nc2cccc(C(F)(F)F)c2)c1]
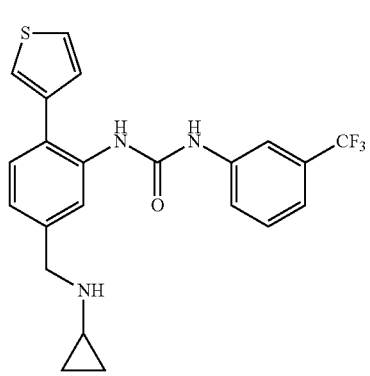 [SMILES: O=C(Nc1cccc(C(F)(F)F)c1)Nc1cc(CNC2CC2)ccc1-c1ccsc1]
-continued
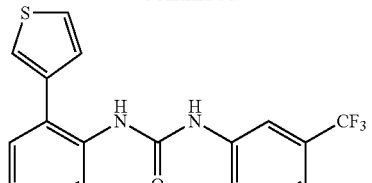
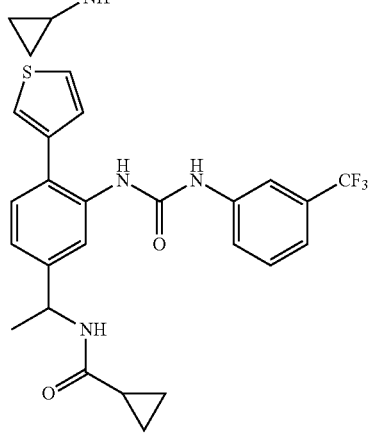
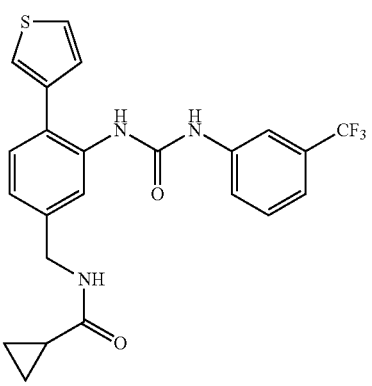 [SMILES: O=C(Nc1cccc(C(F)(F)F)c1)Nc1cc(CNC(=O)C2CC2)ccc1-c1ccsc1]
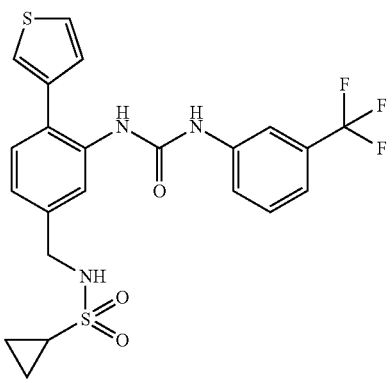 [SMILES: O=C(Nc1cccc(C(F)(F)F)c1)Nc1cc(CNS(=O)(=O)C2CC2)ccc1-c1ccsc1]
or pharmaceutically acceptable salts or hydrates thereof.
17. A pharmaceutical composition, comprising the compound of claim 1, or a pharmaceutically acceptable salt or hydrate thereof, and one or more pharmaceutically acceptable carriers or excipients.

18. A method for treating IDH2 mutation-induced cancers, comprising administering to a subject in need thereof the compound of claim 1, or a pharmaceutically acceptable salt or hydrate thereof.

19. The method according to claim 18, wherein the IDH2 mutation is an IDH2/R140Q mutation or an IDH2/R172K mutation.

20. The method according to claim 18, wherein the IDH2 mutation-induced cancers are selected from the group consisting of glioblastoma, myelodysplastic syndrome, myeloproliferative neoplasm, acute myelogenous leukemia, sarcoma, melanoma, non-small cell lung cancer, chondrosarcoma, bile duct cancer, and angioimmunoblastic non-Hodgkin's lymphoma.

* * * * *